(12) United States Patent
Joseph et al.

(10) Patent No.: US 9,814,413 B2
(45) Date of Patent: Nov. 14, 2017

(54) LONG-TERM IMPLANTABLE MONITORING SYSTEM AND METHODS OF USE

(71) Applicant: Thomas Jefferson University, Philadelphia, PA (US)

(72) Inventors: Jeffrey I Joseph, Penn Valley, PA (US); Amanda L Joseph, Penn Valley, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 0 days.

(21) Appl. No.: 14/808,331

(22) Filed: Jul. 24, 2015

(65) Prior Publication Data

US 2016/0022180 A1   Jan. 28, 2016

Related U.S. Application Data

(60) Provisional application No. 62/028,463, filed on Jul. 24, 2014.

(51) Int. Cl.
*A61B 5/00* (2006.01)
*A61B 5/145* (2006.01)
(Continued)

(52) U.S. Cl.
CPC ........ *A61B 5/14528* (2013.01); *A61B 5/1473* (2013.01); *A61B 5/14532* (2013.01); *A61B 5/6876* (2013.01); *A61M 5/1723* (2013.01); *A61M 27/002* (2013.01); *A61B 5/0031* (2013.01); *A61B 5/1451* (2013.01); *A61B 5/1459* (2013.01); *A61B 5/1495* (2013.01); *A61B 5/14552* (2013.01); *A61B 5/14556* (2013.01); *A61B 5/6852* (2013.01); *A61B 5/7282* (2013.01); *A61B 5/742* (2013.01); *A61B 5/746* (2013.01); *A61B 2560/0214* (2013.01); *A61M 5/14* (2013.01); *A61M 2205/0244* (2013.01); *A61M 2205/04* (2013.01)

(58) Field of Classification Search
CPC . A61B 5/14532; A61B 5/1455; A61B 5/1495; A61B 5/1459; A61B 5/14546; A61B 5/14525; A61B 5/14528; A61B 5/686
See application file for complete search history.

(56) References Cited

U.S. PATENT DOCUMENTS 4,265,249 A * 5/1981 Schindler ............... A61B 5/145
600/573
4,703,756 A   11/1987 Gough et al.
(Continued)

FOREIGN PATENT DOCUMENTS

EP        2004241 B1    8/2013

*Primary Examiner* — Eric Winakur
(74) *Attorney, Agent, or Firm* — Cozen O'Connor

(57) ABSTRACT

Methods and systems include a long-term implantable ultra-filtrate monitoring system that uses micro-porous membranes to produce an ultra-filtrate of tissue interstitial fluid or blood plasma. The ultra-filtrate is transported through a sensor to detect a level of analyte in the ultra-filtrate. The long-term implantable fluid monitoring system thus includes a first porous catheter, a second porous catheter, a sensor configured to measure an amount of analyte in fluid, and a pump configured to move fluid through the first porous catheter to the sensor and from the sensor through the second porous catheter.

18 Claims, 40 Drawing Sheets

(51) Int. Cl.
  *A61B 5/1473* (2006.01)
  *A61M 5/172* (2006.01)
  *A61M 27/00* (2006.01)
  *A61B 5/1455* (2006.01)
  *A61B 5/1459* (2006.01)
  *A61B 5/1495* (2006.01)
  *A61M 5/14* (2006.01)

(56) References Cited

U.S. PATENT DOCUMENTS

| | | | |
|---|---|---|---|
| 4,759,371 A * | 7/1988 | Franetzki | A61B 5/14528 600/373 |
| 4,777,953 A | 10/1988 | Ash et al. | |
| 4,854,322 A | 8/1989 | Ash et al. | |
| 5,002,054 A * | 3/1991 | Ash | A61B 5/14528 600/347 |
| 5,869,774 A | 2/1999 | Backlund et al. | |
| 5,879,367 A | 3/1999 | Latterell et al. | |
| 5,919,369 A | 7/1999 | Ash | |
| 5,925,018 A | 7/1999 | Ungerstedt | |
| 5,947,953 A | 9/1999 | Ash et al. | |
| 5,995,860 A | 11/1999 | Sun et al. | |
| 6,030,358 A | 2/2000 | Odland | |
| 6,042,561 A | 3/2000 | Ash et al. | |
| 6,049,727 A | 4/2000 | Crothall | |
| 6,102,872 A | 8/2000 | Doneen et al. | |
| 6,122,536 A | 9/2000 | Sun et al. | |
| 6,304,766 B1 | 10/2001 | Colvin | |
| 6,459,917 B1 * | 10/2002 | Gowda | A61B 5/1411 600/345 |
| 6,471,689 B1 * | 10/2002 | Joseph | A61L 29/04 424/424 |
| 6,537,241 B1 | 3/2003 | Odland | |
| 6,618,603 B2 | 9/2003 | Varalli et al. | |
| 6,702,857 B2 | 3/2004 | Brauker et al. | |
| 6,770,030 B1 | 8/2004 | Schaupp et al. | |
| 6,800,451 B2 | 10/2004 | Daniloff et al. | |
| 6,805,683 B1 | 10/2004 | Johansson | |
| 6,862,534 B2 | 3/2005 | Sterling et al. | |
| 6,929,618 B1 | 8/2005 | Johansson | |
| 6,940,590 B2 | 9/2005 | Colvin, Jr. et al. | |
| 6,989,891 B2 | 1/2006 | Braig et al. | |
| 7,009,180 B2 | 3/2006 | Sterling et al. | |
| 7,022,071 B2 | 4/2006 | Schaupp et al. | |
| 7,078,554 B2 | 7/2006 | Daniloff et al. | |
| 7,157,723 B2 | 1/2007 | Colvin et al. | |
| 7,235,350 B2 | 6/2007 | Schulman et al. | |
| 7,248,912 B2 | 7/2007 | Gough et al. | |
| 7,336,984 B2 | 2/2008 | Gough et al. | |
| 7,364,592 B2 | 4/2008 | Carr-Brendel et al. | |
| 7,415,299 B2 * | 8/2008 | Zimmermann | A61B 5/14514 210/321.75 |
| 7,593,108 B2 | 9/2009 | Sterling et al. | |
| 7,613,491 B2 | 11/2009 | Boock et al. | |
| 7,717,871 B2 | 5/2010 | Odland | |
| 7,722,537 B2 | 5/2010 | Sterling et al. | |
| 7,800,078 B2 | 9/2010 | Colvin et al. | |
| 7,822,450 B2 | 10/2010 | Colvin et al. | |
| 7,871,456 B2 | 1/2011 | Gough et al. | |
| 7,894,870 B1 | 2/2011 | Lucisano et al. | |
| 7,935,092 B1 | 5/2011 | Odland et al. | |
| 7,939,332 B2 | 5/2011 | Colvin, Jr. | |
| 7,951,357 B2 | 5/2011 | Gross et al. | |
| 8,073,548 B2 | 12/2011 | Colvin et al. | |
| 8,143,068 B2 | 3/2012 | Colvin, Jr. et al. | |
| 8,229,546 B2 | 7/2012 | Falken et al. | |
| 8,273,228 B2 | 9/2012 | Dall'Oglio et al. | |
| 8,303,533 B2 | 11/2012 | Regittnig et al. | |
| 8,318,193 B2 | 11/2012 | Ratner et al. | |
| 8,415,184 B2 | 4/2013 | Colvin et al. | |
| 8,502,167 B2 | 8/2013 | Colvin, Jr. et al. | |
| 8,535,537 B2 | 9/2013 | Feichtner et al. | |
| 8,604,810 B2 | 12/2013 | Sheppard, Jr. | |
| 8,608,922 B2 | 12/2013 | Papadimitrakopoulos et al. | |
| 8,647,393 B2 | 2/2014 | Marshall et al. | |
| 2004/0124147 A1 | 7/2004 | Fissell et al. | |
| 2006/0122536 A1 | 6/2006 | Haar et al. | |
| 2006/0213836 A1 * | 9/2006 | Fissell | A61M 1/3489 210/645 |
| 2007/0060834 A1 | 3/2007 | Odland et al. | |
| 2009/0152200 A1 * | 6/2009 | Lannoy | A61M 1/34 210/647 |
| 2010/0114002 A1 * | 5/2010 | O'Mahony | A61B 5/1427 604/6.09 |
| 2010/0160749 A1 | 6/2010 | Gross et al. | |
| 2010/0303772 A1 | 12/2010 | McMillan et al. | |
| 2011/0049040 A1 | 3/2011 | O'Connell et al. | |
| 2012/0046651 A1 | 2/2012 | Beyer et al. | |
| 2012/0265034 A1 | 10/2012 | Wisniewski et al. | |
| 2012/0265118 A1 * | 10/2012 | Solomon | A61M 1/1678 604/6.09 |
| 2013/0126349 A1 | 5/2013 | Zhang | |
| 2014/0335343 A1 * | 11/2014 | Brauker | A61B 5/14532 428/221 |

* cited by examiner

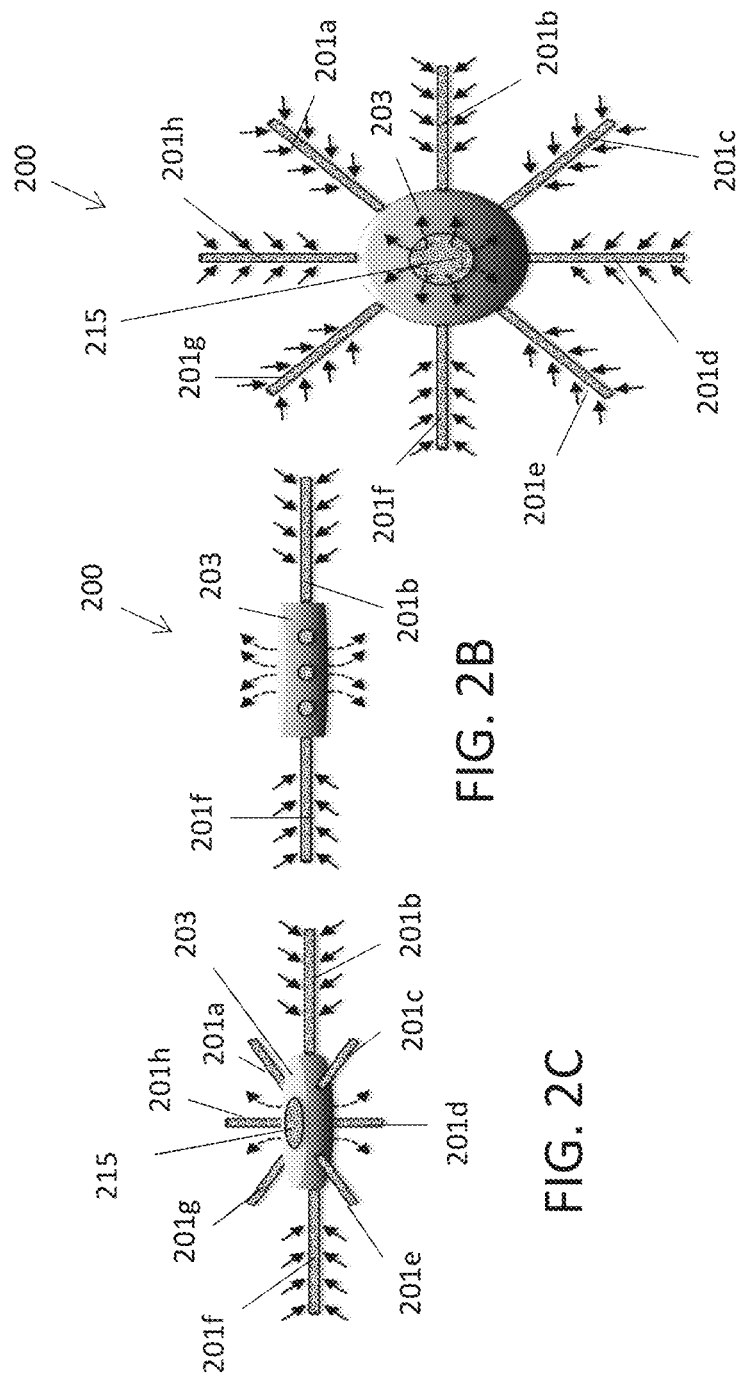

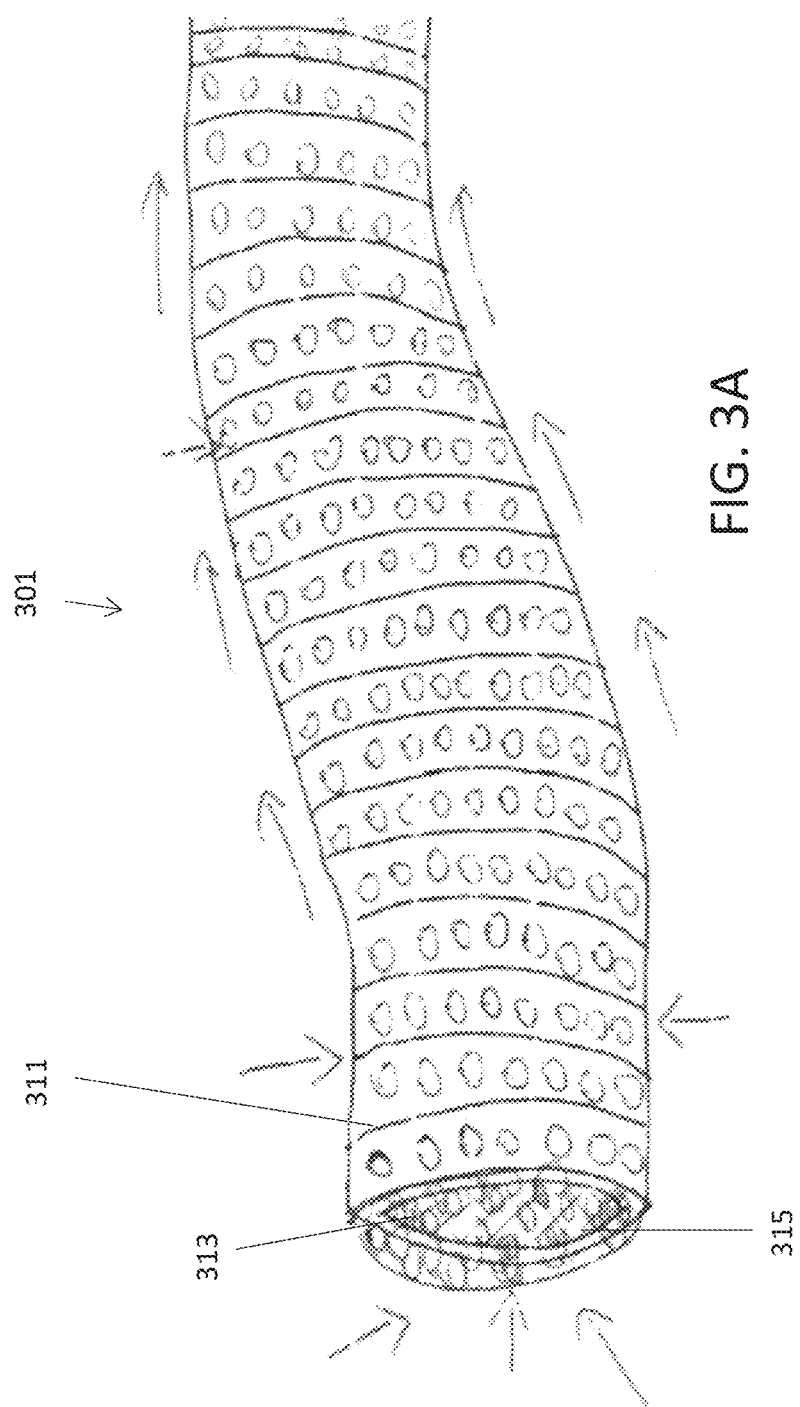

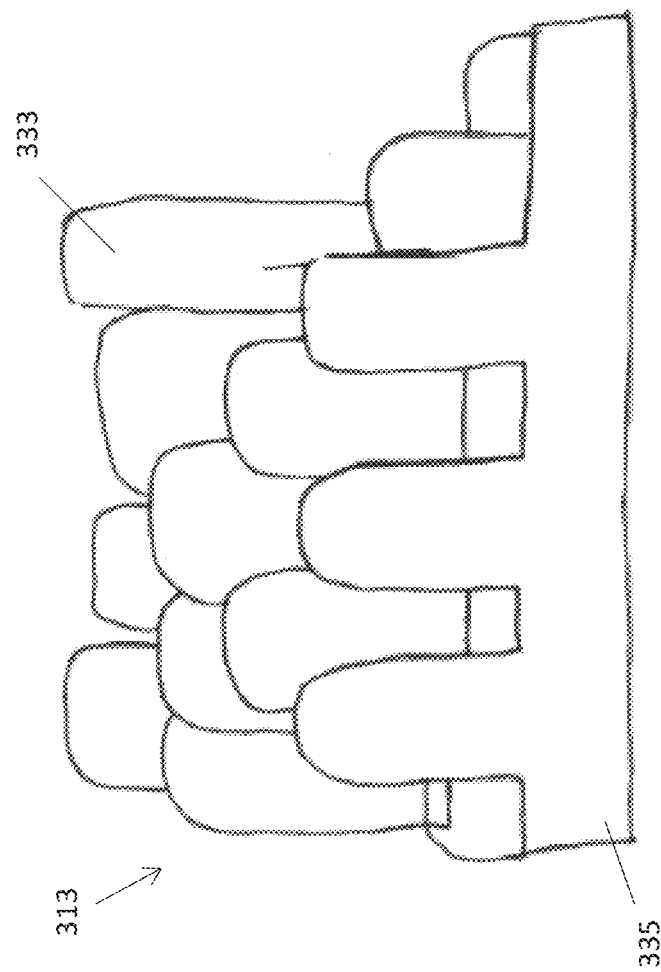

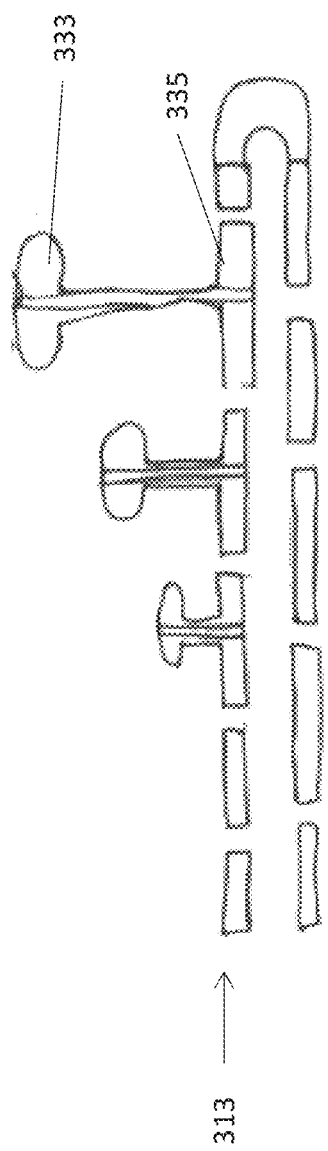

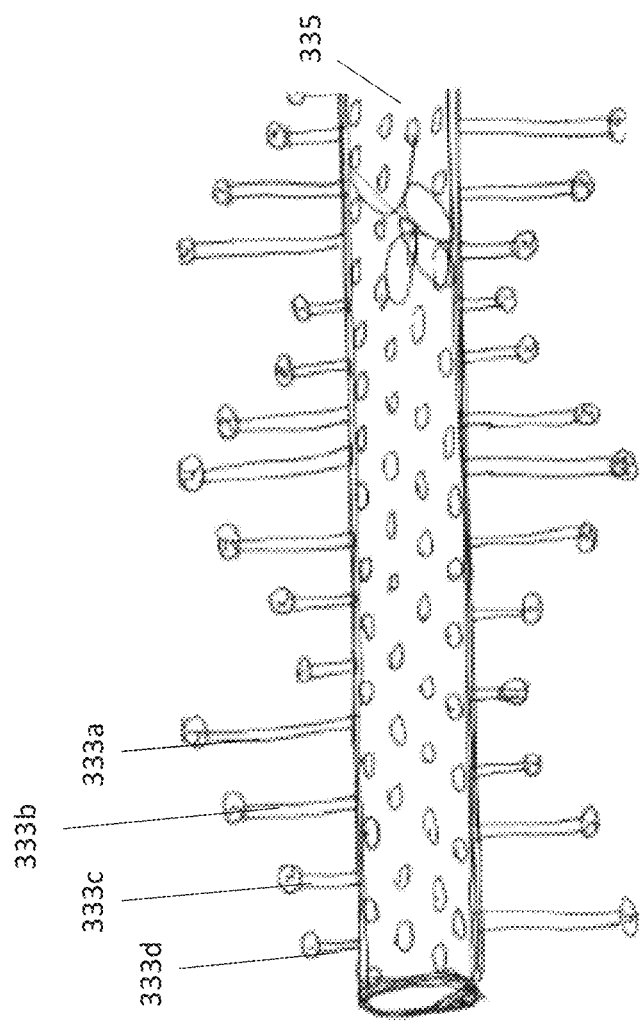

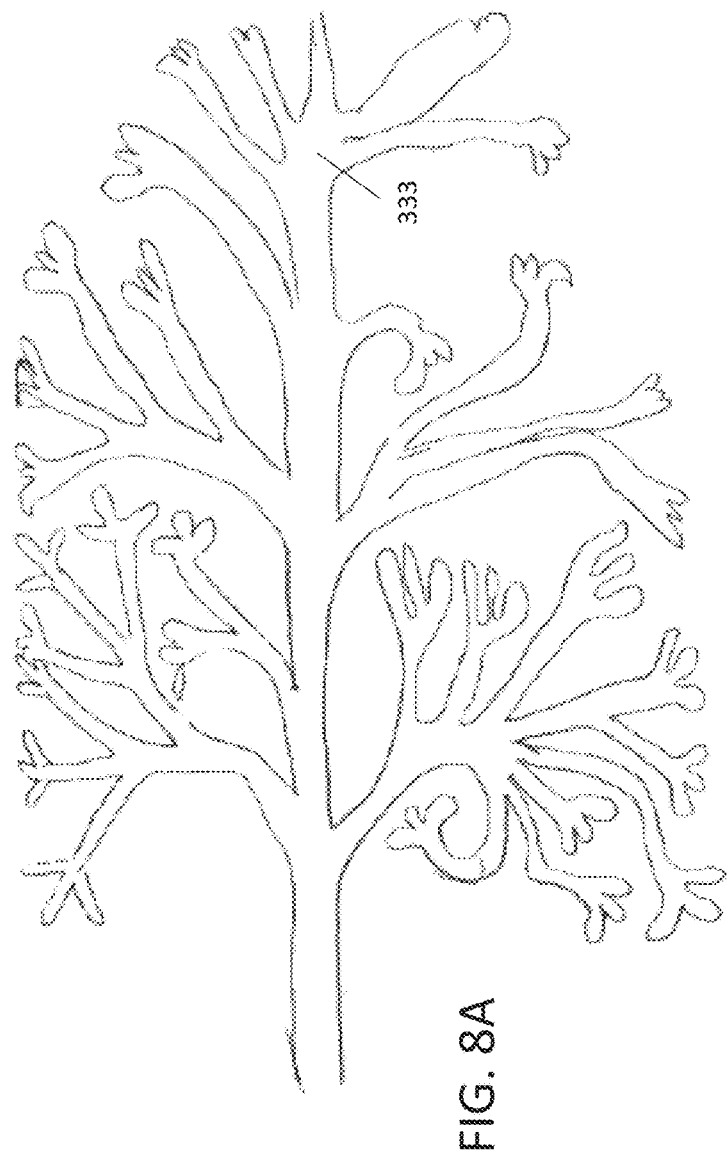
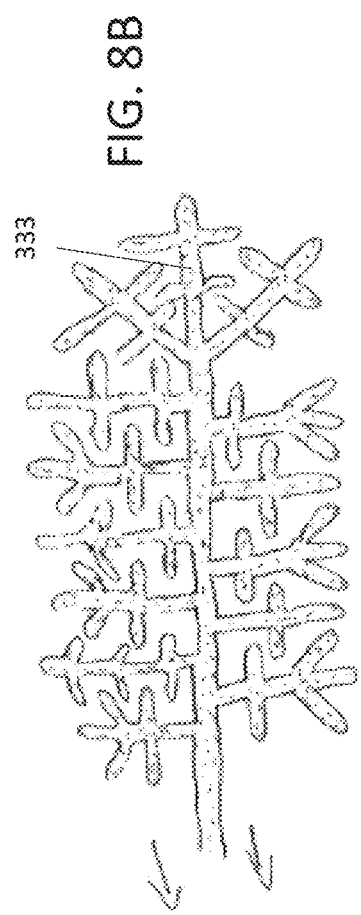
FIG. 8A
FIG. 8B

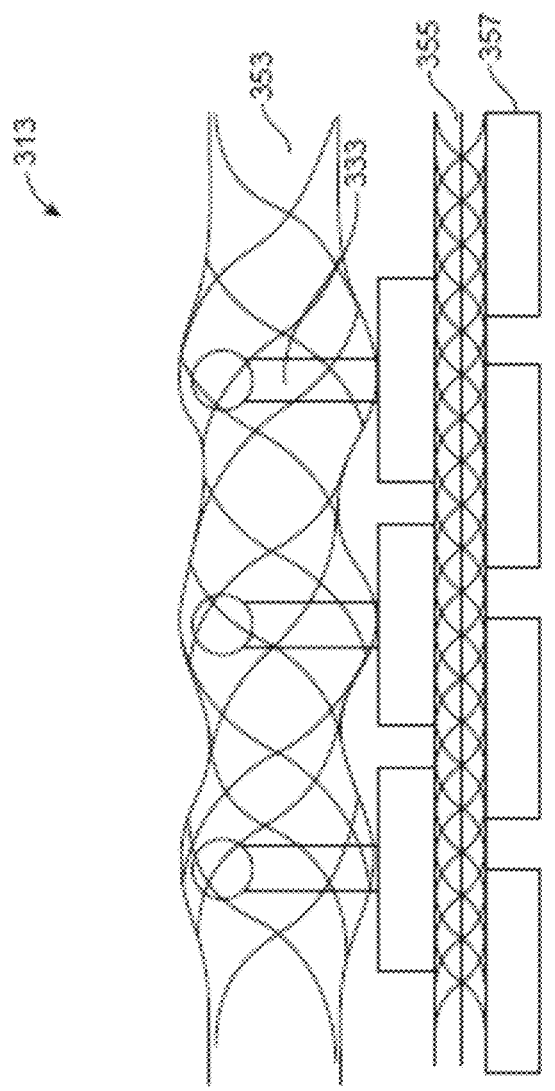

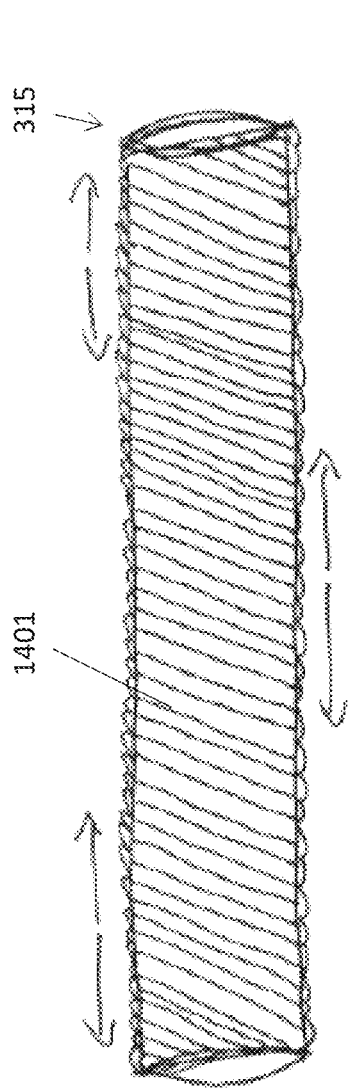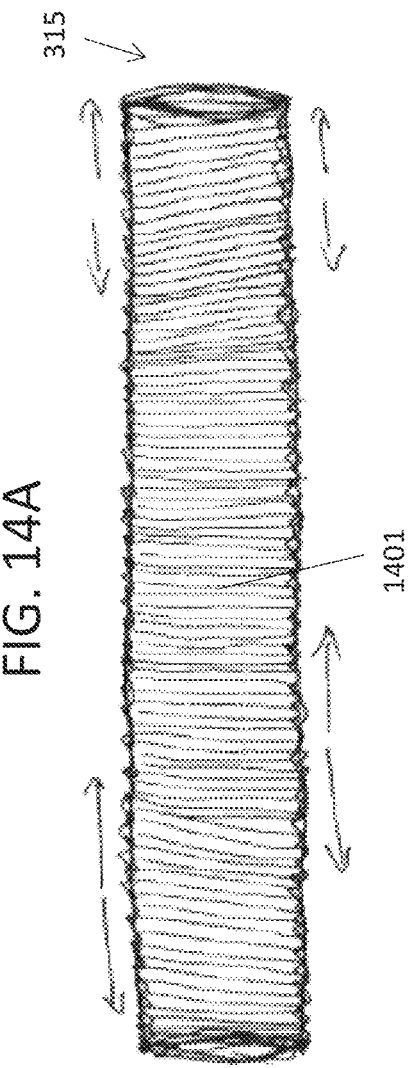
FIG. 14A
FIG. 14B

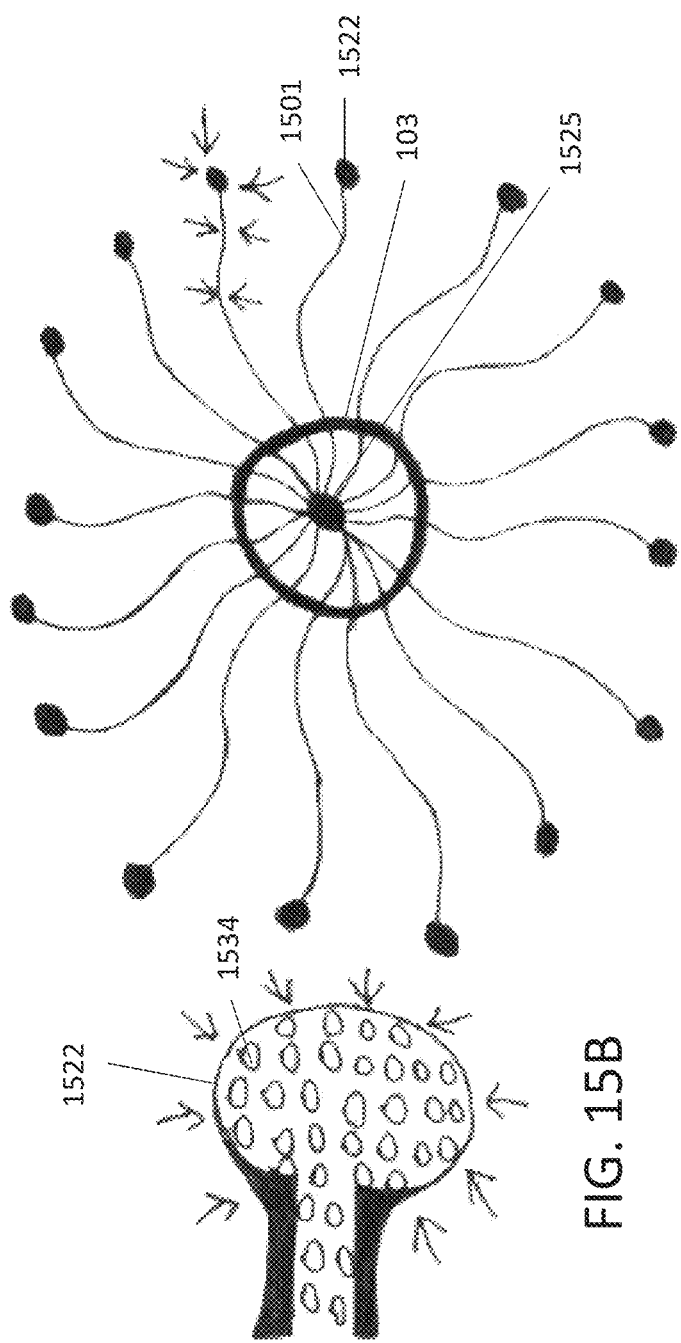

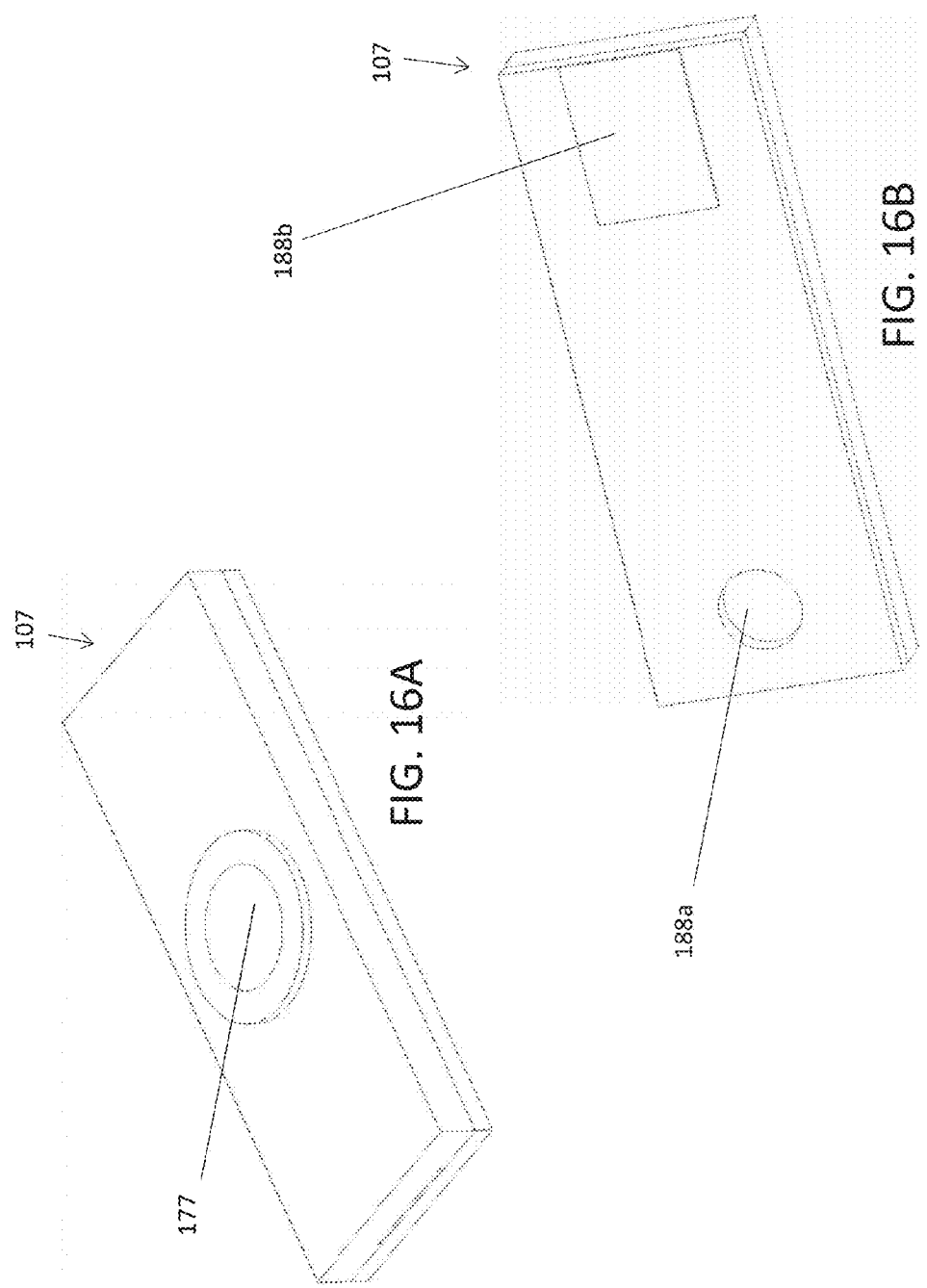

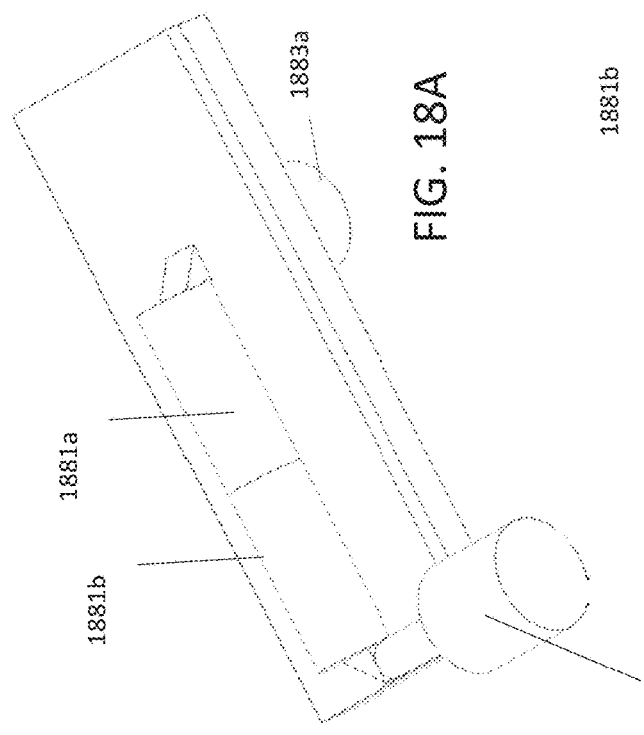
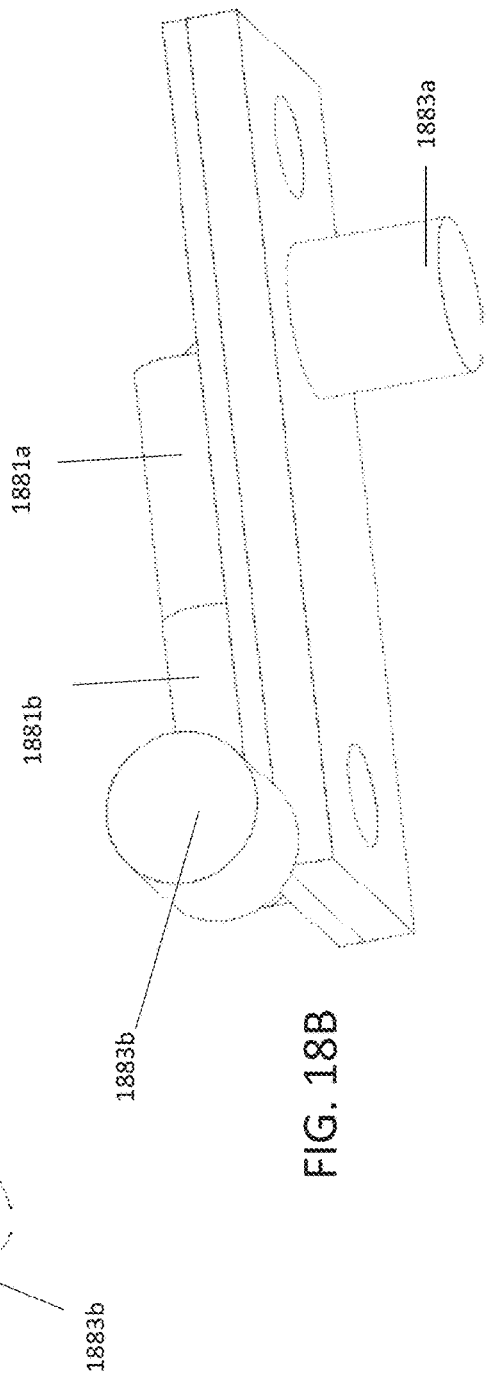
FIG. 18A
FIG. 18B

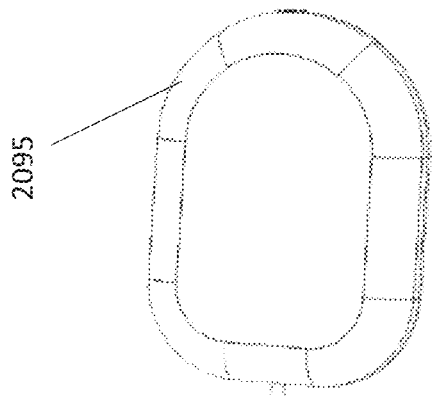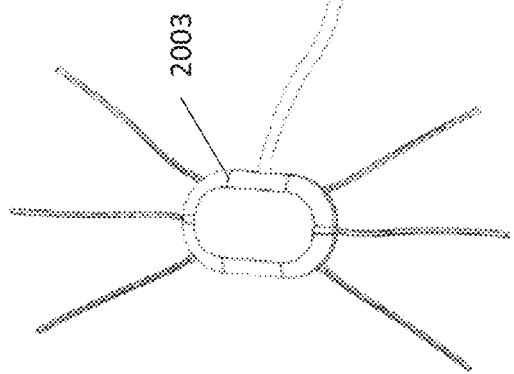
FIG. 20

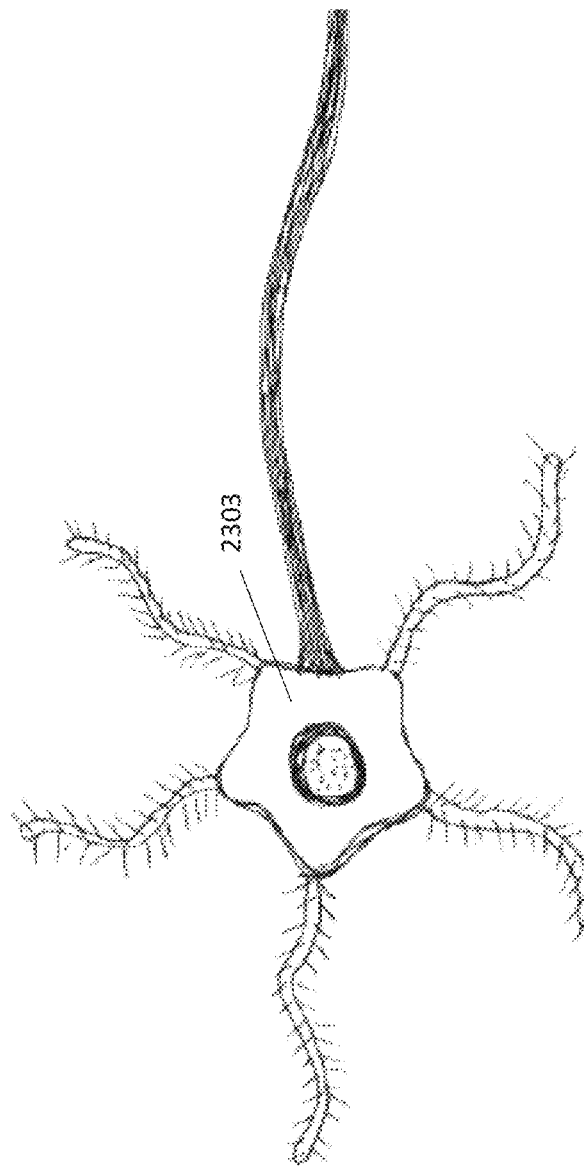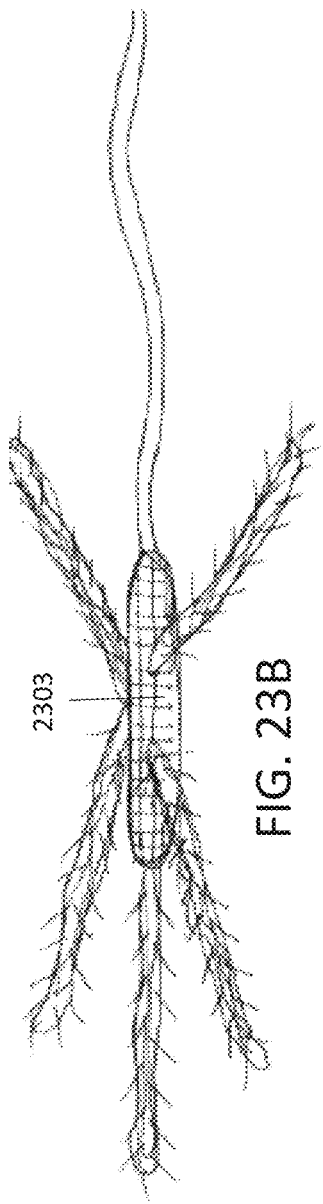
FIG. 23A
FIG. 23B

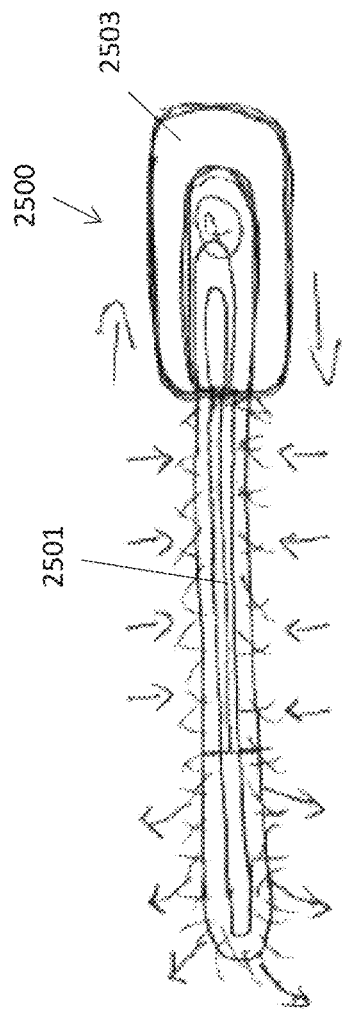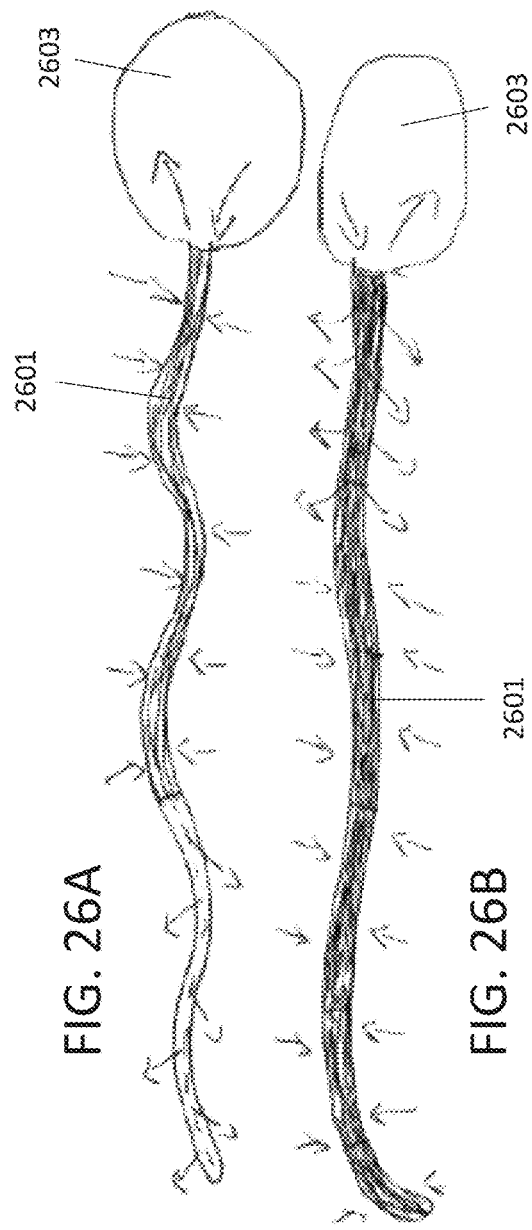
FIG. 25
FIG. 26A
FIG. 26B

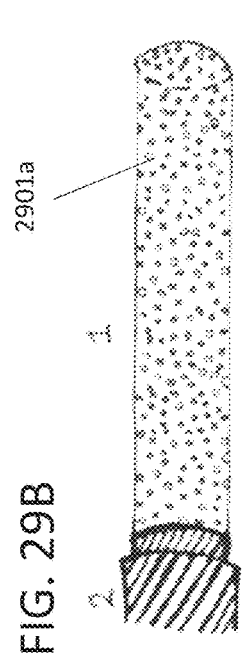
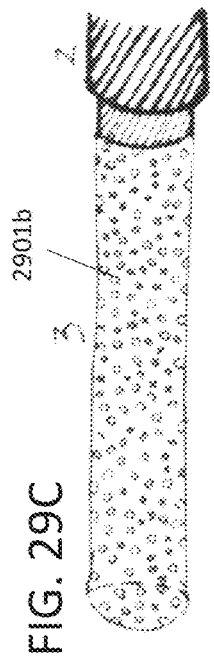
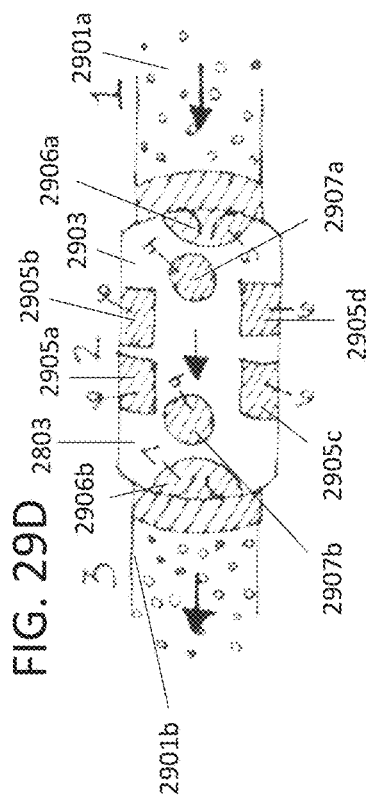
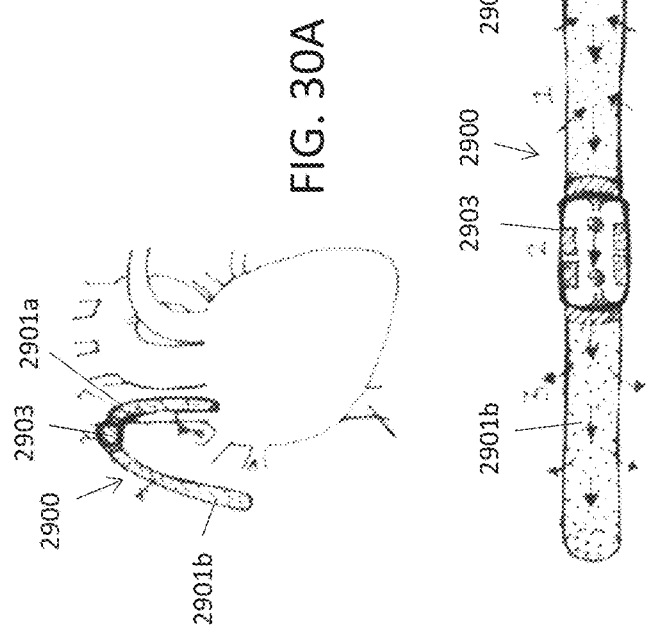
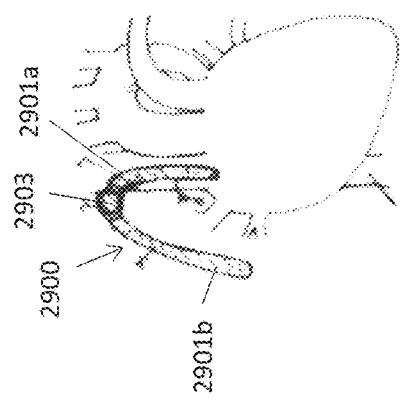
FIG. 29B
FIG. 29C
FIG. 29D
FIG. 30A
FIG. 29A

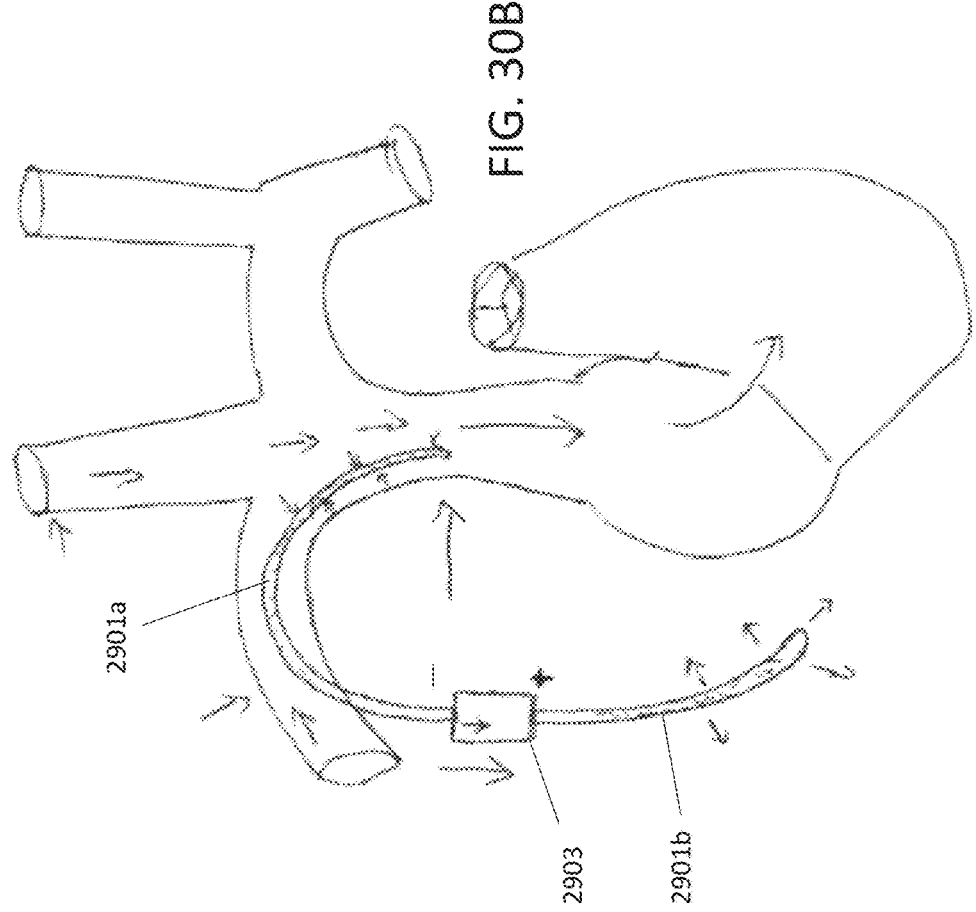

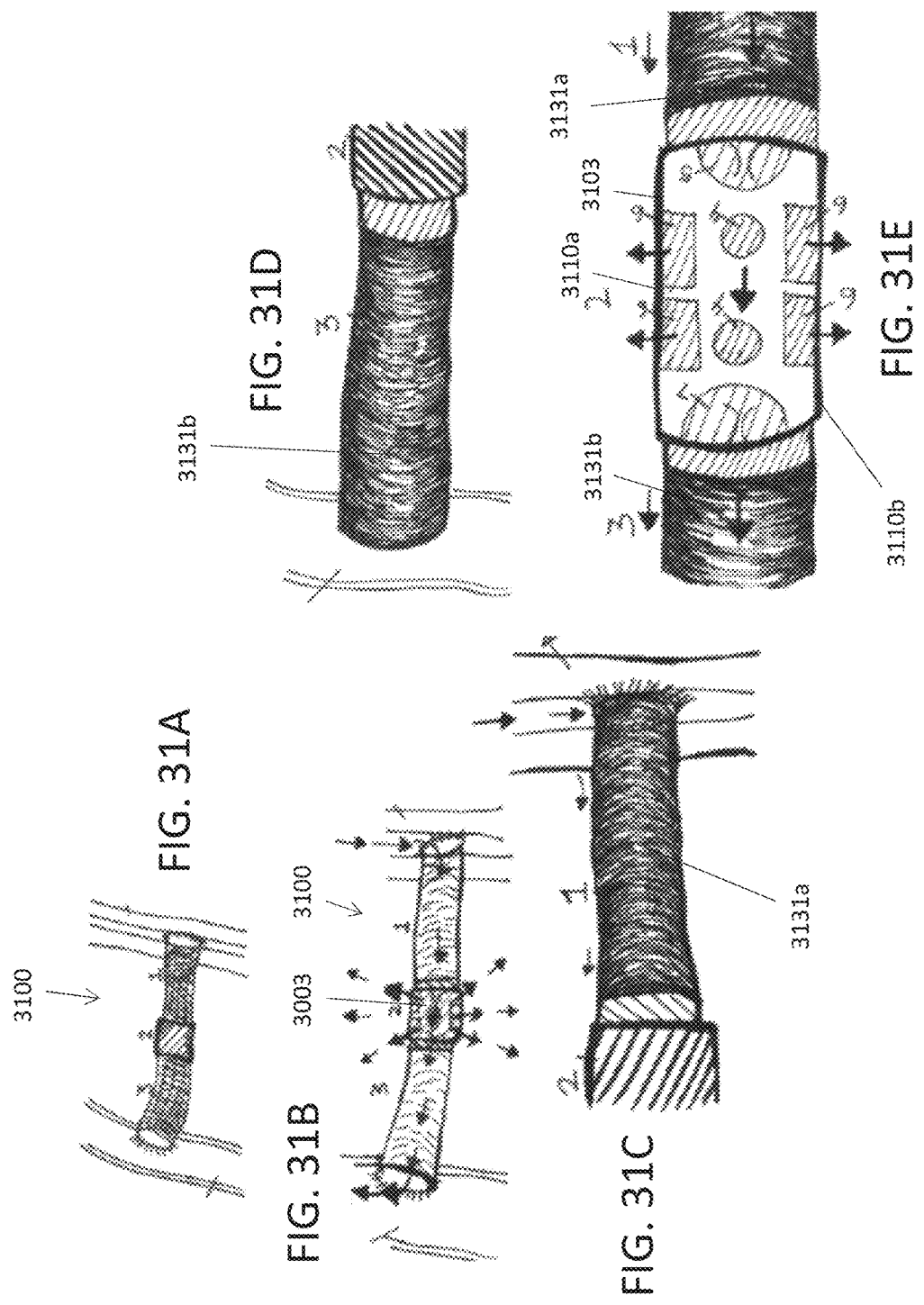

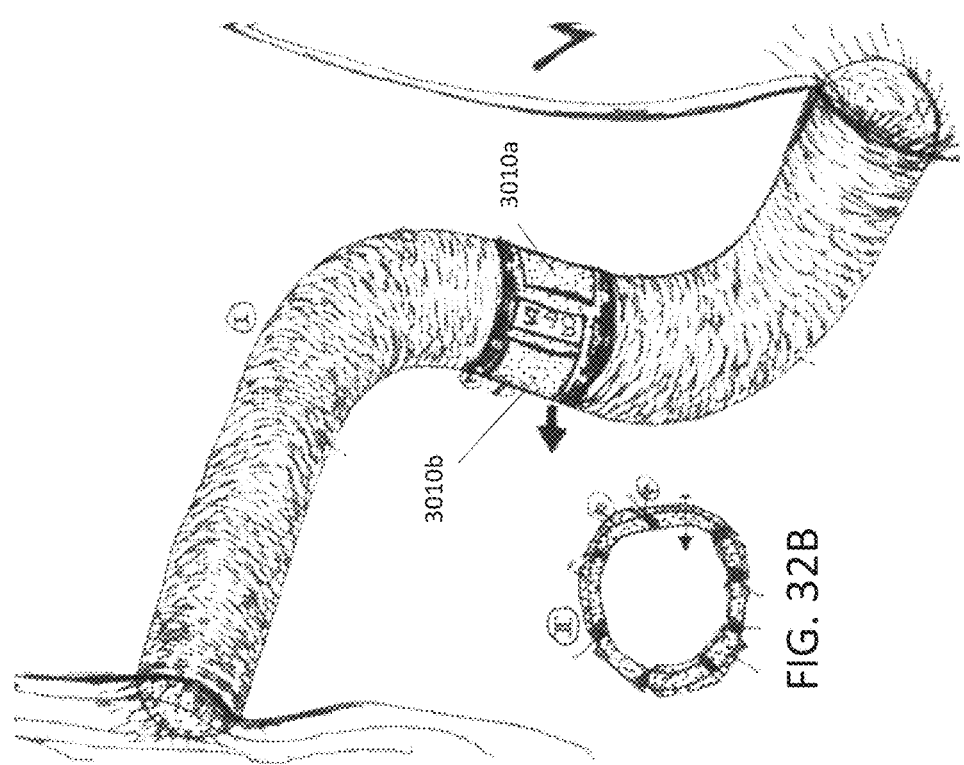

LONG-TERM IMPLANTABLE MONITORING SYSTEM AND METHODS OF USE

CROSS-REFERENCE TO RELATED APPLICATIONS

This application claims priority to U.S. Provisional Application No. 62/028,463, titled "LONG-TERM IMPLANTABLE MONITORING SYSTEM & METHODS OF USE", filed Jul. 24, 2014, the entirety of which is incorporated by reference herein.

BACKGROUND

Approximately 1.2 million people in the United States have type 1 diabetes (T1DM) and require insulin for survival. Half of these patients use an insulin pump, a subcutaneous insulin infusion (CSII) catheter, and rapid acting insulin to manage their diabetes. The other half of the patients inject insulin into their subcutaneous tissue 3 to 4 times per day (multiple dose injection therapy or MDI) using a syringe with a small gauge needle or an insulin pen. Most patients with type 1 diabetes SMBG (self-monitor blood glucose) multiple times per day using a glucose meter and test strips.

Although another 24 to 28 million people in the USA have type 2 diabetes (T2DM), only 2.5 million are currently being managed with insulin. The majority of patients with type 2 diabetes who manage with insulin conduct SMBG two or more times per day. Some patients with type 2 diabetes managed with diet, exercise, and oral medication SMBG daily. Further, the prevalence of type 2 diabetes is projected to increase to more than 60 million people by 2050 due to the epidemic of obesity, metabolic syndrome, and pre-diabetes in children and adolescence in the U.S. The number of people in the world with type 2 diabetes is expected to exceed 300 million by the year 2020. Patients with poorly controlled BG levels for months to years are at increased risk for MI, CHF, stroke, blindness, kidney failure, infection, limb amputation, and premature death. Aggressive BG control with insulin and oral hypoglycemia medications in elderly patients with type 2 diabetes has been associated with an increased risk for hypoglycemia and premature death. More than 50% of the T2DM patient managed with insulin could benefit from real-time CGM with alerts and alarms for hyperglycemia and hypoglycemia. Elderly patients with T2DM may have difficulty utilizing current subcutaneous tissue CGM glucose sensors that require self-insertion every 5 to 7 days and frequent SMBG prior to insulin dose adjustments.

Outcome studies have clearly demonstrated the clinical benefit of controlling the blood glucose (BG) concentration as close to normal for age throughout a person's lifetime. Even modest improvements in BG control lead to a marked reduction in the incidence of blindness, kidney failure, heart failure, neuropathy, and limb amputation due to microvascular disease. The combination of BG control, blood pressure control, and lipid lowering therapy leads to a marked reduction in the incidence of ischemic heart disease, myocardial infarction, peripheral vascular disease, and ischemic stroke due to macro-vascular disease.

Many people with T1DM are able to control their BG in the near-normal range using multiple dose injection (MDI) therapy or insulin pump therapy with rapid acting insulin delivered through a continuous subcutaneous insulin infusion (CSII) catheter. Safe and effective insulin therapy requires frequent BG monitoring to maintain the BG concentration in the desired range because human metabolism changes minute by minute due to the consumption of food (meal size, composition, and time of day), exercise (type, intensity and duration), illness, sleep, medications, and the complex interaction of hormones, cytokines, growth factors, and the brain/autonomic nervous system. Despite education and motivation, the majority of people with type 1 diabetes commonly experience clinically significant episodes of hyperglycemia, hypoglycemia, and glycemic variability.

A growing number of people with T1DM use the real-time glucose information from a subcutaneous tissue continuous glucose monitoring system (CGMS) to manage their blood glucose. After insertion into the subcutaneous tissue, the continuous glucose monitor (CGM or glucose sensor) measures and displays the interstitial fluid glucose concentration (mg/dL or mmol/L) once per minute for 5 to 7 days. People with T1DM can use the glucose trend information (direction and rate of change) and alarms to significantly improve their time in the desired target BG range (for example 90 to 140 mg/dl) and minimize the incidence and duration of hypoglycemia (for example <70 mg/dl). However, many children and adults do not utilize this new technology because the glucose sensors do not produce a measurement accurate enough to eliminate the need for a confirmatory fingerstick blood glucose measurement (SMBG) prior to making an adjustment in insulin therapy. Many glucose sensors do not correlate closely with BG measurements due to an unstable sensor-tissue interface, errors in calibration, variable time-lag, and sensor instability due to movement and bio-fouling.

Despite these limitations, CGM systems have been integrated with insulin pumps and control algorithms (closed-loop and semi-closed loop) to automatically adjust insulin delivery as part of an Artificial Pancreas (AP) System. Clinical research studies are currently evaluating the safety and efficacy of using real-time subcutaneous tissue CGM trend data to frequently adjust the subcutaneous tissue infusion of rapid acting insulin. The Medtronic Diabetes Revel System that integrates a real-time CGM with an insulin pump and a control algorithm recently received FDA approval for suspending the infusion of insulin for 2 hours at night when the CGM detects hypoglycemia.

Three continuous glucose monitoring systems are CE Mark approved in Europe as a tool for the management of type 1 diabetes in adults and children (Medtronic Diabetes, Abbott Diagnostics, and DexCom Inc.). The DexCom and Medtronic CGM glucose sensor have FDA approval for commercial sale in the U.S. The commercial CGMs are labeled as adjunctive devices that use the glucose trend information (direction and rate of change) to alert the patient of impending hyperglycemia and hypoglycemia. A reference blood glucose measurement is required multiple times per day to determine the appropriate doses of insulin and to calibrate the CGM sensor.

The CGM sensors have miniature flexible electrodes that are inserted through the skin into the subcutaneous adipose tissue every 5 to 7 days. The concentration of tissue fluid glucose is measured every 1 to 5 minutes using an enzyme-based electrochemical sensor that oxidizes glucose to hydrogen peroxide and extra electrons. The change in electric current is proportional to the change in the glucose concentration within the local environment around the sensor's electrodes. All CGM sensors require an initial calibration and frequent re-calibration (every 6 to 12 hours) over the 5 to 7 day life of the sensor using a reference blood glucose measurement.

CGM sensors commonly loose sensitivity and drift after implantation into the subcutaneous tissue due to the acute inflammatory response to injury. The environment surrounding the sensor's electrodes is filled with edema fluid, plasma proteins, thrombus, platelets, lysed cells, macrophages, and neutrophils. Many commercial CGM sensors do not correlate with the blood glucose concentration for several hours after implantation (run-in time 2 to 8 hours). Many commercial CGM sensors do not correlate with the blood glucose concentration during their entire 5 to 7 day lifetime due to ongoing changes in the tissue environment surrounding the sensor electrodes. The skin insertion site and subcutaneous tissue sensor site may develop an infection or more significant immune response if worn for more than 5 to 7 days. The adhesive tape used to hold the sensor to the skin commonly causes skin irritation and inflammation.

Several companies are trying to develop long-term implantable ISF or blood glucose monitoring systems. One company is developing a differential oxygen electrochemical CGM with telemetry for long-term implantation within the subcutaneous tissue of the abdomen. The CGM is designed to measure the concentration of subcutaneous tissue oxygen and glucose once per minutes for more than one year. The technology requires glucose and oxygen molecules to diffuse from the subcutaneous tissue through a fibrous capsule and porous membrane to interact with oxygen electrodes and oxygen electrodes covered with glucose-oxidase enzyme. The glucose responsive signal is subtracted from the oxygen signal to measure the glucose concentration. Accuracy, stability, longevity, and time-lag are adversely affected by slow and variable simple diffusion through the tissue, fibrous capsule, and membrane to the working electrode(s). This CGM may fail prematurely due to thickening and loss of capillaries within the fibrous capsule and chemical degradation of the enzymes/electrodes.

Another company is developing a CGM for long-term implantation within the subcutaneous tissue that monitors the concentration of ISF glucose using a glucose sensitive chemical (boronic acid) and fluorescent chemicals. The technology requires glucose molecules to diffuse from the subcutaneous tissue through a fibrous capsule and porous membrane to interact with the CGM chemicals. An external electronic/optical module is adhered to the skin to intermittently power the implanted glucose sensor and receive an output signal that correlates with a change in the intensity of florescence. Accuracy, stability, longevity, and time-lag are adversely affected by slow and variable simple diffusion of glucose molecules through the tissue, fibrous capsule, and membrane to the boronic acid. This CGM fails prematurely due to thickening and loss of capillaries within the fibrous capsule, degradation of the boronic acid, and photo-bleaching of the fluorescent chemicals.

A third company is developing a CGM for long-term implantation within the subcutaneous tissue that monitors the concentration of ISF glucose using glucose-sensitive fluorescent chemicals within a hydrogel. The hydrogel is designed to enhance the ingrowth and maintenance of vascular tissue. This technology requires glucose molecules to diffuse from the subcutaneous tissue through the hydrogel to interact with the fluorescent chemicals. An external electronic/optical module is adhered to the skin to intermittently send energy into the fluorescent chemicals and receive an output signal that correlates with a change in the intensity of florescence. Accuracy, stability, longevity, and time-lag are adversely affected by slow and variable simple diffusion of glucose molecules through the tissue and hydrogel. This CGM fails prematurely due to thickening and loss of capillaries within the hydrogel, degradation of the hydrogel, and photo-bleaching of the fluorescent chemicals.

Ultra-filtration is a commonly used clinical technique whereby the large molecules responsible for poor vascular sensor performance are excluded from the sample matrix. Ultrafiltration is accomplished by commercial membranes which are similar to those used for hemodialysis and hemo-filtration. Current commercial membranes designed for short-term hemodialysis, hemo-filtration, and ultra-filtration have a relatively large and heterogeneous porous structure. Many of these membranes perform well for short periods of time, but may develop an obstructed fluid flow pathway due to the adhesion of protein, cells, platelets, and thrombus. For example, a wide variety of membranes (polysulfone, polyacrylonitrile (PAN), poly methyl-methacrylate, poly ethersulfone, polyamide, ethyl-vinyl alcohol, polycarbonate, HEMA (hydroxyl methylmethacrylate), PMMA (polymethylmethacrylate), PHEMA (polyhydroxymethyl methacrylate), MM (methyl methacrylate), PE (polyethylene), HDE (high density polyethylene), PEG (polyethylene glycol), Sulfobetaine (polySB), silicone, PVC (poly vinyl chloride), PV (polyvinyl alcohol), PP (polypropylene), PEEK, polyamide (Nylon), cellulose diacetate, mixed-ester cellulose, PTFE (polytetrafluoroethylene-Teflon), acrylic copolymer; nanometer sized carbon nanotubes and polymer fibers (spun or weaved into an interconnecting mat-like structure), Dacron, PGA (polyglycolic acid), collagen (types I, III, IV, or V), elastin, fibrin, fibronectin, laminin, hyuronic acid, thrombin, and synthetic basement membrane (Matrigel) have been developed to facilitate a rapid rate of water flow/flux and the passage of small and large molecules (molecular cut-off 20,000 to <50,000 MW or Daltons) for short-term hemodialysis, hemo-filtration, and ultra-filtration.

Ultra-filtration is currently being used in clinical medicine during cardiopulmonary bypass and in volume overloaded ICU patients with renal disease to remove excess water from the body. The patient's blood is anti-coagulated with heparin and transported around the outside of the porous hollow fibers using the patient's arterial blood pressure or an external pump to produce flow. A small amount of vacuum can be applied to the inside of the porous membrane fibers to enhance ultra-filtrate formation. The anti-coagulated blood is returned to the patient's artery or vein. Sieving coefficient is calculated as the ratio of the concentration of the solute in the ultra-filtrate (glucose and water) to that in the incoming plasma (glucose and water). All of the commercial porous membranes have a sieving coefficient of 1 for glucose, which means all of the glucose molecules pass completely into the ultra-filtrate.

Many of these porous membranes have been commercialized for clinical use. However, none of the commercial porous membranes have been optimized for long-term implantation in the subcutaneous tissue or the bloodstream for the production of ultra-filtrate from tissue fluid or plasma with a small molecular weight cut-off.

No company, however, has been able to develop and commercialize a long-term glucose monitoring system, despite years of research and development. A long-term glucose monitoring system, such as one including a porous membrane for creation of an ultrafiltrate, is desired that overcomes some or all of the above challenges/obstacles.

SUMMARY

Described herein are long-term implantable analyte monitoring systems.

An exemplary embodiment described herein includes a long-term implantable ultra-filtrate monitoring system that uses micro-porous membranes to produce an ultra-filtrate of interstitial fluid or blood plasma. The ultra-filtrate is transported through a flow-through sensor that can accurately and continuously monitor the chemical concentration and/or physical composition of the ultra-filtrate solution [glucose, insulin, c-peptide, lactate, pyruvate, glycerol, beta-hydroxy butyrate, aceto-acetic acid, acetone, fatty acids, triglycerides, cholesterol, electrolytes, BUN, creatinine, liver enzymes (LDH, SGOT), pH, oxygen, carbon dioxide, bicarbonate, osmolarity, markers of tissue ischemia/infarction (CPK, troponin), tumor markers fordysplasia and neoplasia, hormones, markers of inflammation, growth factors, cytokines, drug levels, vitamin levels]. The ultra-filtrate is then transported through a second porous membrane to enter the subcutaneous tissue for absorption into the capillary and lymphatic vessels. Exemplary embodiments may use a micro-processor controlled pump system, such as MEMS pumps and pressure transducers, to control the flow of fluid through the micro-porous membrane.

Thus, the long-term implantable device continuously produces an ultra-filtrate of tissue fluid or plasma, transports the ultra-filtrate through a sensor, and then transports the ultra-filtrate into adjacent subcutaneous tissue for absorption. The system uses a battery powered pump(s), pressure transducer(s), and porous membranes to produce "Starling Forces" that mimic the structure and function of the kidney's glomerulus and/or capillary endothelial cells and basement membrane.

A controlled hydrostatic pressure differential is used to actively move fluid from the interstitial tissue or plasma through the porous membrane's channels into the lumen of the implanted CGM. A controlled hydrostatic pressure differential is then used to actively move fluid through the flow-through sensor at a slow and steady rate (0.5 to 20 microliters/minute). A controlled hydrostatic pressure differential is then used to actively move the ultra-filtrate fluid from the CGM lumen through the channels of a second porous membrane to be absorbed into adjacent capillaries and lymph vessels. In contrast to all other long-term implantable CGM under development, some embodiments disclosed herein actively move fluid containing small molecules (water, sodium, chloride, and glucose) from one location to another location in the body, through a flow-through sensor.

Embodiments described herein may be used, for example, in a long-term implantable interstitial fluid glucose monitoring system. For example, the long-term implantable interstitial fluid glucose monitoring system may include a catheter with a macro and micro-porous structure for subcutaneous tissue implantation. An exemplary embodiment of a macro/micro porous structure comprises a multi-layered membrane. An outermost porous structure may be designed to promote and maintain the ingrowth of vascular tissue long-term, and prevent or reduce the formation of a fibrous capsule. A middle porous structure may be used as a filter that continuously produces an ultra-filtrate from tissue fluid. Pore or channel size, shape, thickness, length, density, electric charge, and surface chemistry can be varied and controlled to produce an ultra-filtrate with the optimal chemical and physical properties for long-term monitoring of any analyte, including glucose. An inner structure may be designed for mechanical support, so that the lumen does not collapse due to negative internal pressure or external compression. The catheter construction, materials, and surface coatings may be configured to maintain an open interconnecting pore structure long-term, that simulates the structure and function of a kidney glomerulus and/or capillary endothelial cells/basement membrane. The porous structure can be designed as a highly flexible catheter, sphere, oval, or rounded disc. The flexible catheter can have a three-dimensional branching micro-fluidic system with villi, micro-villi, and a distal tip sphere with pores/channels that greatly increase the surface area in contact with vascular tissue for enhanced fluid movement. The described structures can be combined, separated, duplicated, removed, and/or reordered depending on the desired application and characteristics.

Embodiments described herein may be used, for example, in a long-term implantable ultra-filtrate monitoring system that measures blood plasma analytes such as glucose. For example, the long-term implantable blood glucose monitoring system may include a micro-porous structure within the catheter body for insertion within a large blood vessel such as the superior vena cava. The outermost porous structure may be designed to be highly hemocompatible with a surface chemistry that minimizes the adhesion of platelets, plasma proteins, fibrin, and vessel wall tissue. The middle porous structure may comprise the micro-porous structure used as a filter that continuously produces an ultra-filtrate of plasma. Pore size, shape, thickness, density, electric charge, and surface chemistry can be varied to produce an ultra-filtrate of plasma with the optimal chemical and physical properties for long-term monitoring of glucose. The inner porous structure may be designed for mechanical support, so that the catheter lumen does not collapse due to negative internal pressure. The described structures can be combined, separated, duplicated, removed, and/or reordered depending on the desired application and characteristics.

Embodiments described herein may be used, for example, in a long-term implantable vascular shunt ultra-filtrate monitoring system. For example, the long-term implantable vascular shunt glucose monitoring system may comprise a vascular graft configured to be anastomosed between two arteries or an artery and a vein by a surgeon. The ultra-filtrate forming micro-porous membrane structure may be built into the wall of a synthetic vascular graft (for example Dacron, polyurethane, or ePTFE). The outmost layer of the porous membrane may be configured through composition, surface coating, thickness, pore size, degree of porosity, and/or electric charge to be highly hemocompatible and minimize the adhesion of platelets, plasma proteins, and fibrin. Hydrostatic pressure within the vascular graft lumen (mean blood pressure) may be used to drive the continuous formation and flow of ultra-filtrate through the porous membranes and sensor into adjacent subcutaneous tissue. The hydrostatic pressure differential (blood pressure–tissue fluid pressure) will cause water, sodium, chloride, glucose, and other small molecules (ultra-filtrate) to actively move from the plasma into the adjacent subcutaneous tissue (without the need for a battery powered fluid pump). Ultra-filtrate may then be rapidly absorbed into the capillaries and lymph vessels of adjacent subcutaneous tissue.

Embodiments of the present system may therefore include a long-term implantable glucose (analyte) monitoring system. In an exemplary embodiment, the present system may continuously and reliable produce an ultra-filtrate of plasma or interstitial fluid for more than one year (e.g., 3 to 6 years). The clear ultra-filtrate produced through exemplary membranes may contain water, glucose, electrolytes, and other small molecules, but in some embodiments do not have cells and/or large molecules/compounds that may affect the performance of an optical, enzyme, or fluorescence analyte or glucose sensor. Exemplary embodiments include small dead-space of the flow-through sensor to minimize lag-time. Beneficial to the long-term performance of the implantable monitoring system is the multi-layer porous membrane that produces a characteristic and stable ultra-filtrate from blood plasma or ISF for many years. Beneficial to the reliable and stable production of ultra-filtrate is the real-time monitoring and control of the micro-fluids system. The control algorithm may be designed to maintain a continuous forward flow of ultra-filtrate by adjusting the pressure differentials ($P1>P2>P3>P4$) across the porous membrane(s) and sensor compartments. The pumps and valves can reverse the hydrostatic pressure differential and thus reverse the flow of ultra-filtrate ($P4>P3>P2>P1$). Regular reversal of flow (left to right, then right to left) through the porous membranes may be used to minimize biofouling (physical obstruction) of the membrane's channels and pores. Mechanical vibration may also be used to minimize biofouling (physical obstruction) of the membranes channels and pores.

An exemplary product may consist of an implantable monitoring system and an external electronics module. The implanted monitoring system an external electronics module may communicate in both directions via RF telemetry. The external module can be a smart watch, a smart cell phone, an automobile electronics module, or an iPad with a large color display and an integrated glucose meter to facilitate re-calibration. The external module may have programmable alerts and alarms for any significant change in ultra-filtrate chemistry or composition (for example hyperglycemia, hypoglycemia, and rapid rate of glucose change).

In general, in one embodiment, a long-term implantable fluid monitoring system includes a first porous catheter, a second porous catheter, a sensor configured to measure an amount of analyte in fluid, and a pump configured to move fluid through the first porous catheter to the sensor and from the sensor through the second porous catheter.

This and other embodiments can include one or more of the following features. The first porous catheter can include a multi-layer wall including an outer layer, a middle layer, and an inner layer. The outer layer can have larger pores than the middle layer. The inner layer can be configured to provide structural support. The pump can be a microelectromechanical pump or a nanoelectromechanical pump.

The system can further include a controller and at least one pressure sensor. The controller can be configured to regulate the pump based upon readings from the at least one pressure sensor to maintain a constant flow of fluid through the sensor. The sensor can be an optical sensor. The sensor can be a differential oxygen sensor, an enzyme sensor, an electrochemical sensor, a fluorescence sensor, or a physical change sensor. The first porous catheter can be configured to produce an ultra-filtrate from body fluid, and the sensor can be configured to measure an amount of analyte in the ultra-filtrate. The analyte can be glucose. The system can further include an external display configured to display the amount of analyte in the fluid. The system can further include a communications module configured to communicate the amount of analyte in the fluid to a central monitoring station. The system can further include an implantable battery configured to provide power to the pump. The system can further include an alarm mechanism configured to alert for hyperglycemia based upon the measured analyte level, hypoglycemia based upon the measured analyte level, or a rapid rate of change in analyte level. The system can further include a controller configured to determine an optimal infusion dose of insulin or glucagon based upon the measured analyte level.

In general, in one embodiment, a method of measuring a level of analyte in body fluid includes: (1) implanting a monitoring system into a body of a patient; (2) creating an ultra-filtrate from a body fluid using the implanted monitoring system; (3) measuring an amount of analyte in the ultra-filtrate with a sensor of the implanted monitoring system; and (4) returning the ultra-filtrate to the body.

This and other embodiments can include one or more of the following features. The method can further include calibrating the monitoring system based upon an external measurement of the analyte. The implanting step can include implanting into subcutaneous vascular tissue of an abdomen, chest wall, thigh, or mesentery of a bowel between the visceral and parietal peritoneal membrane. The implanting step can include implanting at least a portion of the system into a blood vessel (e.g., vein). The implanting step can include implanting a porous catheter in a vein and a central module connected to the porous catheter in subcutaneous tissue. The implanting step can include implanting between a vein and an artery as a vascular shunt. Creating an ultra-filtrate can include creating an ultra-filtrate with a multi-layer porous membrane. The sensor can be an optical sensor. The method can further include creating a pressure differential to pull the ultra-filtrate into the sensor and return the ultra-filtrate to the body. The method can further include maintaining a constant pressure differential despite dynamic changes in hydrostatic pressure or oncotic pressure. A rate of creating the ultra-filtrate can be between about 1 to >10 µL/min, and in certain embodiments, between about 1-2 µL/min. The method can further include displaying the measured amount of analyte. The method can further include activating an alarm for hyperglycemia based upon the amount of analyte, hypoglycemia based upon the amount of analyte, or a rapid rate of change in the amount of analyte. The analyte can be glucose. The body fluid can be interstitial fluid. The body fluid can be blood.

In general, in one embodiment, an implantable fluid monitoring system includes a porous catheter. The porous catheter includes a first, second, and third layer, and a sensor. The first layer includes a plurality of first pores. The second layer includes a plurality of second pores and a plurality of microneedles. The second pores are smaller than the first pores, and the plurality of microneedles extend into the first layer by a plurality of different amounts. The third layer is configured to provide structural support to the catheter. The sensor is configured to measure an amount of analyte in fluid that is transferred through the porous catheter to the sensor.

This and other embodiments can include one or more of the following features. The system can further include a pump configured to move fluid through the porous catheter and into the sensor. The pump can be a microelectromechanical pump or a nanoelectromechanical pump. The sensor can be an optical sensor. The sensor can be a differential oxygen sensor, an enzyme sensor, an electrochemical sensor, a fluorescence sensor, or a physical change sensor. The porous catheter can be configured to produce an ultra-filtrate from body fluid, and the sensor can be configured to measure an amount of analyte in the ultra-filtrate. The analyte can be glucose. The system can further include an external display configured to display the amount of analyte in the fluid. The system can further include a communications module configured to communicate the amount of analyte in the fluid to a remote monitoring station.

In general, in one embodiment, a method of measuring a level of analyte in body fluid includes: (1) implanting a monitoring system into a body of a patient, the monitoring system including a porous catheter having a plurality of different layers therein; (2) allowing tissue to grow into an outer layer of the porous membrane; (3) pulling fluid through the porous catheter and into a sensor to create an ultra-filtrate; and (4) measuring an amount of analyte in the ultra-filtrate with the sensor.

In general, in one embodiment, a method of measuring an amount of analyte in a body fluid includes: (1) inserting a first portion of an implantable monitoring system into the lumen of a blood vessel and a second portion of the implantable monitoring system into adjacent subcutaneous tissue of a patient; (2) forming an ultra-filtrate from blood within the blood vessel; (3) detecting analyte levels of the ultra-filtrate; and (4) returning the ultra-filtrate into the adjacent subcutaneous vascular tissue.

In general, in one embodiment, a long-term implantable vascular shunt monitoring system includes a vascular graft and a micro-porous membrane attached to the vascular graft. The vascular graft is configured to be anastomosed to artery-vein or artery-artery. The micro-porous membrane is configured to form an ultra-filtrate of blood plasma from fluid passed through the micro-porous membrane.

In general, in one embodiment, a method of measuring blood analyte levels includes: (1) inserting an implantable vascular shunt monitoring system into a patient between two arteries or from an artery to vein; (2) forming an ultra-filtrate from blood flowing through the monitoring system; and (3) detecting a level of analyte in the ultra-filtrate using the monitoring system.

The implants described herein can be implanted into any vascular tissue, such as into the subcutaneous tissue of an abdomen, flank, chest wall, back, or thigh, into muscle tissue, into the mesentery of the bowel, or between the visceral and parietal peritoneal membranes.

BRIEF DESCRIPTION OF THE DRAWINGS

FIGS. 2A-2C shows another embodiment of an exemplary implantable glucose monitor.

FIG. 3A shows a porous catheter of an implantable glucose monitor.

FIG. 5A shows a middle layer of a porous catheter with microfluidic microneedles extending therefrom.

FIG. 5B shows a middle layer of a porous catheter with microneedles of varying lengths extending therefrom.

FIG. 7 shows a portion of a middle layer of a porous catheter with microneedles of different lengths extending therefrom in a pattern.

FIGS. 8A and 8B show branching microneedles for use in a middle layer of a porous catheter.

FIGS. 10A and 10B show a middle layer of a porous catheter with three sub-layers.

FIGS. 14A and 14B show an inner layer of a porous catheter that is configured as an extendable coil.

FIG. 15A shows an implantable glucose monitoring device with a plurality of catheters extending therefrom where the catheters having porous bulbs at the distal ends thereof. FIG. 15B shows a close-up of a porous bulb.

FIGS. 16A and 16B show an exemplary pump assembly for use with a glucose monitoring system.

FIGS. 18A and 18B show an exemplary optical sensor for a glucose monitoring system.

FIG. 20 shows another embodiment of a glucose monitoring implant having a central module and an external module.

FIGS. 23A-23B show another shape of a central module of a glucose monitoring system.

FIG. 25 shows another embodiment of a glucose monitoring system with a single catheter.

FIGS. 26A-B show another embodiment of a glucose monitoring system with a single catheter.

FIGS. 29A-D show an exemplary blood glucose monitor.

FIGS. 30A-30B show use of an exemplary implanted blood glucose monitor.

FIGS. 31A-31E show an exemplary vascular shunt glucose monitor.

FIGS. 32A and 32B show another embodiment of a vascular shunt glucose monitor.

DETAILED DESCRIPTION

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

As used herein, the term "about" means within 10% of a stated number.

The implantable glucose monitoring system described herein can advantageously consistently monitor analyte levels, such as glucose levels, in real-time over a long implantation period (e.g., between 3 and 30 years, greater than 3 years, greater than 5 years, or greater than 10 years).

Figure 1:
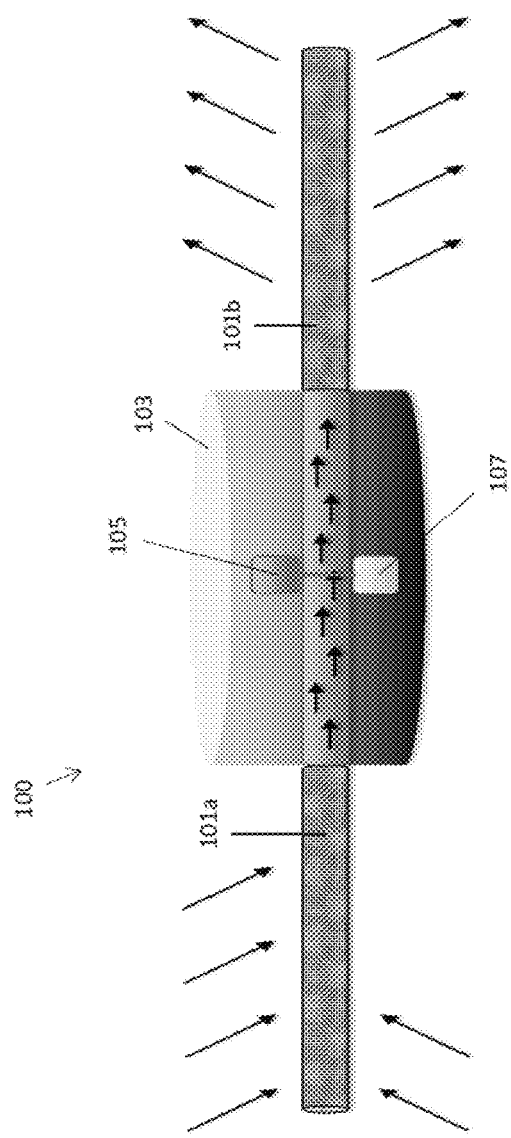
FIG. 1 shows an exemplary implantable glucose monitor.

Referring to FIG. 1, an exemplary flow-through glucose-monitoring implant 100 includes a plurality of porous catheters 101a, b attached to a central module 103. The central module 103 can include a flow-through sensor 105, such as an optical sensor, and a pump 107, such as a miniature or microelectromechanical (MEMS) pump, therein. As shown by the arrows in FIG. 1, the pump 107 can be configured to move fluid (e.g., interstitial fluid, blood) from the implantation site into the porous catheter 101a, through the sensor 105, out through the porous catheter 101b, and back into the implantation site. The implant 100 can be used to filter interstitial fluid or plasma into an ultra-filtrate and measure the amount of analyte, such as glucose, in the ultra-filtrate. Thus, some or all of the implant 100 (e.g., at least the porous catheters 101a, b) can be in direct contact with interstitial fluid or blood when implanted.

Referring to FIGS. 2A-2C, an implant 200 can include a plurality of different catheters 201a-h extending radially from a central module 203. In this embodiment, the catheters 201a-h can take fluid in along the longitudinal length of the catheter while the central module 203 can be configured to return the ultra-filtrate or its byproducts to the body through a membrane 215 thereon. Although radial inlet micro-porous catheters 201a-h are shown in FIG. 2 as providing the inlet of fluid while a central membrane provides the outlet, any combination of one or more membranes or catheters may be used as inlet and/or outlet conduits.

The porous catheters 101, 201 described herein can include an ultra-filtration membrane (e.g., in the wall of the catheter) to pass fluid and produce a clear ultra-filtrate of interstitial fluid or blood. Exemplary embodiments of the ultra-filtrate monitoring system include mechanisms for ultra-filtrate formation. The structure and function of the micro-porous membrane is designed to mimic the structure and function of the kidney's glomerulus and/or a fenestrated capillary membrane (e.g., through pore size, pore structure, pore surface area, pore surface chemistry, pore electric charge, pore density, membrane thickness and resistance). Solutes and water can thus move from the interstitial fluid or blood plasma through the membrane pores/channels into the catheter lumen by convective forces, enhanced by a small, medium, or large pressure differential created by a pump. A larger pressure differential will move an ultra-filtrate through the membrane's pores/channels at a faster rate compared to a smaller pressure differential.

Figure 3B:
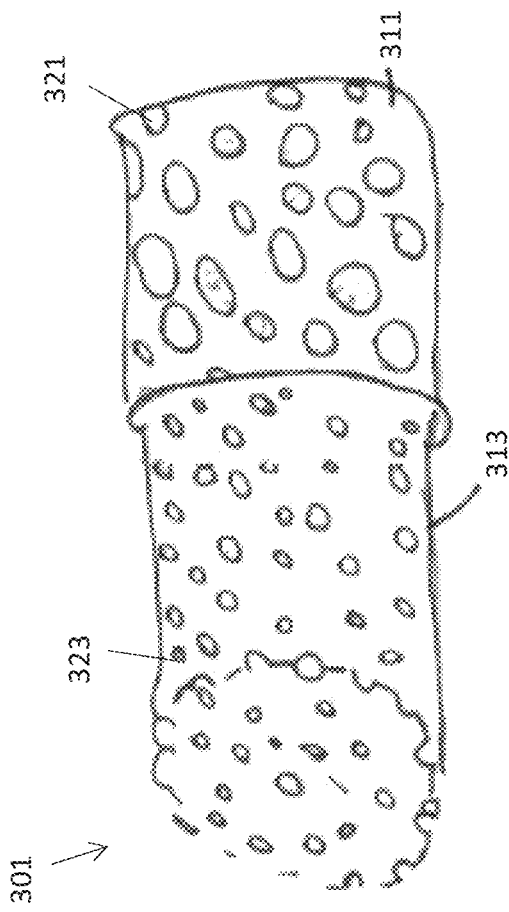
FIG. 3B shows an outer and middle layer of a catheter of an implantable glucose monitor.

The catheter used for the implants described herein can include a micro-porous structure or membrane along at least a portion of the catheter to produce an ultra-filtrate from the received fluid. Referring to FIG. 3A, a catheter 301, which can be used with any of the implants described herein, can be soft and highly flexible (like limp spaghetti) so that the catheters and/or surrounding vascular subcutaneous tissue move as a single unit during ambulation and exercise. As shown in FIGS. 3A and 3B, the catheter 301 can further include three different layers, including an outer layer 311, a middle layer 313, and an inner layer 315, as discussed further below. The outer layer 311 can be configured to interface with adjacent vascular connective tissue or with flowing blood. The middle layer 313 can be configured to produce the ultra-filtrate. The inner layer 315 can provide structural support.

The catheter 301 can be a porous hemodialysis, hemofiltration, or ultrafiltration catheter. In some embodiments, the catheter 301 can be manufactured of cellulose, polyacrylonitrile (PAN), poly methyl-methacrylate, ethyl-vinyl alcohol, and polysulfone, polypropylene, polycarbonate. In other embodiments, the catheter 301 can be manufactured of HEMA (hydroxyl methylmethacrylate), PMMA (polymethylmethacrylate), PHEMA (polyhydroxymethyl methacrylate), MM (methyl methacrylate), PE (polyethylene), HDE (high density polyethylene), PEG (polyethylene glycol), Sulfobetaine (polySB), polycarbonate, silicone, PVC (poly vinyl chloride), PV (polyvinyl alcohol), PP (polypropylene), PEEK, polyamide (Nylon), cellulose diacetate, mixed-ester cellulose, PTFE (polytetrafluoroethylene-Teflon), acrylic copolymer; nanometer sized carbon nanotubes and polymer fibers (spun or weaved into an interconnecting mat-like structure), Dacron, PGA (polyglycolic acid), carbon nanotubes, carbon nanotubes mixed with silicone and other polymers, graphene, collagen (types I, III, IV, or V), elastin, fibrin, fibronectin, laminin, hyuronic acid, thrombin, and synthetic basement membrane (Matrigel).

The catheter 301 can be designed to permit the passage of only low-molecular weight solutes (<5,000 Daltons). In an exemplary embodiment, molecules smaller than 60,000 MW or Daltons (water, electrolytes, glucose, uric acid, creatinine, blood urea nitrogen, and ammonia) will easily pass through exemplary embodiments of the micro-porous catheter to enter the sensor region. In some embodiments for glucose measurement, proteins and other large molecules will not pass through the membrane's pores/channels. Cells and platelets will not pass through the membrane; due to their larger size and negative charge. Of note, glucose has a molecular weight of 180 mw (180 g/mol=180 Da) and a molecular diameter of 7.5 angstroms (7.5 Å=0.75 nm (nanometers)=0.00075 um (micrometers)=7×10−10 m (meters). Water has a molecular weight of 18 mw (18 g/mol=18 Da) and a molecular diameter around 2.75 Å (0.275 nm=0.000275 µm). Exemplary embodiments of a micro-porous membrane comprise a porous membrane with a small pore size (for example, 5 to 10 nanometers), such that the flux of water and glucose is not significantly affected. Water, glucose, and other small molecules will freely and actively move from the subcutaneous tissue's ISF through the porous membranes into the lumen of the sensor based upon a hydrostatic pressure differential, such as a pressure differential produced by a battery powered pump.

Referring to FIG. 3B, the outer layer 311 for the long-term implantable subcutaneous tissue analyte sensor can include a plurality of interconnecting pores or channels 321. The pores 321 can be, for example, between 10 and 200 micrometers in diameter and have a density of 5 to 100 pores per square millimeter of surface area. For example, the outer layer 311 can have a pore 321 diameter of 30 to 40 µm to optimize the ingrowth and maintenance of vascular tissue with a high density of capillary vessels and minimize the formation of fibrous tissue.

Exemplary embodiments of the outer layer 311 designed for vascular tissue implantation can have a large interconnecting pore structure, a thickness of 20 to 200 micrometers, and a Bulk's modulus and Young's modulus similar to adjacent soft tissue (for example, a Young's Modulus of 0.01 to 1.0 giga-pascals or 1,450 to 50,000 pounds/square inch and Bulk's Modulus 2.2 to $3.0 \times 10^9$ Pa or N/m²). In some embodiments, the outer layer 311 can be constructed of soft and hydrophilic biomaterials, such as the hydrogels HEMA (hydroxyl-methyl-methacrylate), PMMA (poly-methyl-methacrylate), PHEMA (poly-hydroxy-methyl-methacrylate), and MM (methyl-methacrylate), polymers (ePTFE, Dacron, poly-glycolic acid) and the natural materials collagen (types I, III, IV, or V), elastin, fibronectin, laminin, hyuronic acid, fibrin, thrombin, and the synthetic basement membrane material Matrigel. The outer layer 311 can also be constructed of carbon nanotubes and/or polymer fibers (1 to 100 nm diameter) that can be spun or weaved into an interconnecting mat-like structure. The nano-fibers can be spun into a structure with open spaces that produce a large surface area for the ingrowth and adhesion of cells, connective tissue and extra-cellular matrix (ECM). Thus, the space between the nano-fibers can become filled with vascular tissue containing arterioles, capillaries, venuoles, and lymph vessels.

Figure 4A:
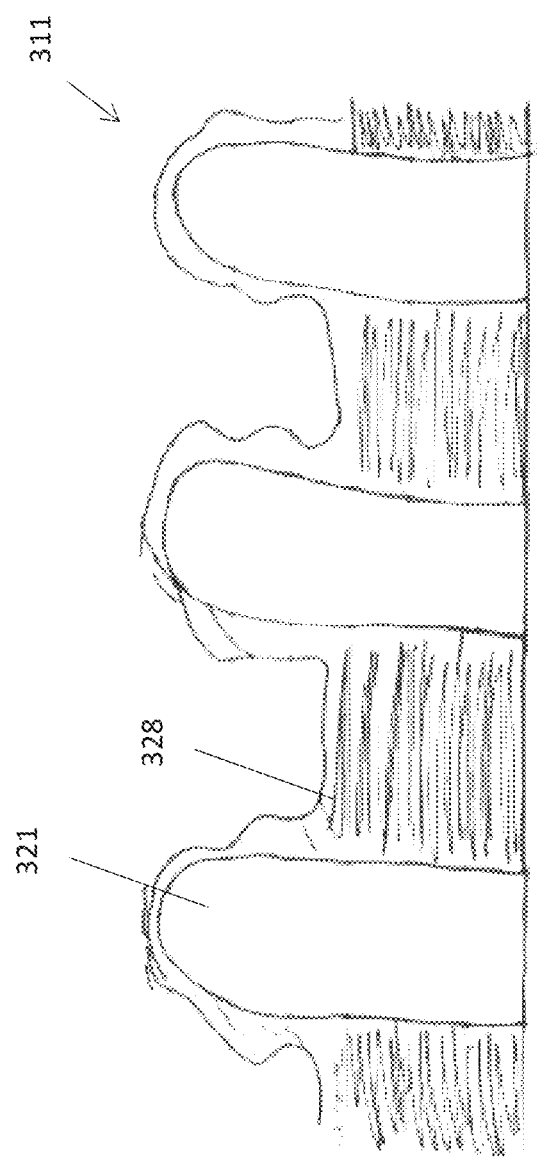
FIG. 4A shows a porous outer layer of a catheter with biomaterial filling the pores to increase biocompatability.

Referring to FIG. 4A, in some embodiments of the outer layer 311 can be filled with a biomaterial 328 to promote biocompatability. For example, the outer layer can be surface coated with drugs and/or growth factors (for example vascular endothelial growth factor (VEGF), platelet-derived growth factor (PDGF), fibroblast growth factor (BFGF), and insulin-like growth factor 1 that increase the ingrowth and maintenance of vascular tissue containing a high density of arterioles, capillaries, and venuoles). In some embodiments, the biomaterial 328 can be functionalized with peptides (RGD, YISGR, PDSGR, REDV), receptors, growth factors, and immune modulators that enhance the adhesion and ingrowth of vascular tissue and extracellular matrix (arterioles, capillaries, venuoles, lymphatics, adipose cells, collagen, elastin, and hyuronic acid).

Figure 4B:
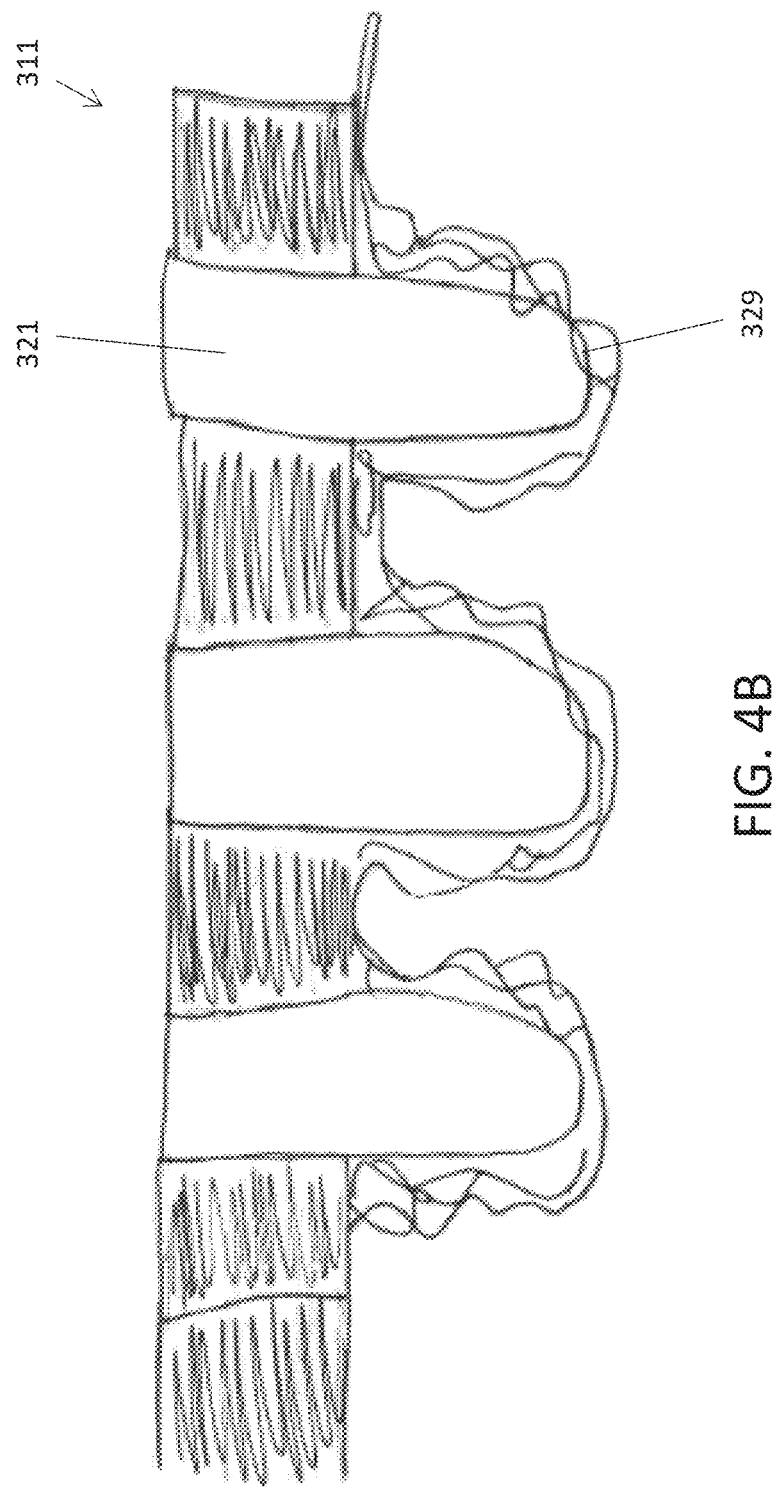
FIG. 4B shows a porous outer layer of a catheter with a biodegradable material filling the pores to increase biocompatability.

In other embodiments, as shown in FIG. 4B, the pores 321 can be filled with compounds 329 that dissolve/biodegrade, such as within 10-30 days, and increases growth of vascular tissue in the meantime. For example, the base of the pores 321 can be filled with FDA approved biodegradable materials such as polyglycolic acid (PGA-polyglactin-Vicryl), Polyglactin 910 (PGLA), Poliglecaprone (Monocryl-PGCL), Polydioxanone (PDS), beef serosa, and/or sheep submucosa. This mechanism can help prevent the base of the pores 321 and the interconnecting pores 321 from becoming filled with cells and connective tissue for 15 to 45 days following implantation, thus preventing the interconnecting porous structure 321 from getting blocked over time as the body heals (i.e., prevent biofouling).

The outer layer 311, when the implant is used subcutaneously, can advantageously serve to allow a healthy vascular connective tissue to grow therein, thereby increasing the length of time that the implant can remain in the interstitial space.

Moreover, in some embodiments, the porous catheter may be implanted long-term within a blood vessel lumen with high flow and high shear forces, such as the superior vena cava. In such cases, the outer layer 311 can be designed to minimize the adhesion of platelets, plasma proteins, fibrin, and endothelial cells. A combination of high flexibility, small diameter, hemo-compatible materials (silicone, polyurethane, polypropylene, Teflon), hemo-compatible and very smooth surface coatings, small pore size, degree of porosity, and/or surface electric charge can be optimized to minimize the adhesion of cells, platelet, and plasma proteins, fibrin, and thrombus.

The outer layer 311, when used in the bloodstream, may have a very smooth surface with a pore size 0.1 to 2.0 micrometers and 500 to 5,000 pores per micrometer squared surface area. Some embodiments for the intravascular catheter may have a small pore size (0.1 to 2 µm³) to minimize mechanical obstruction by platelets (3 µm³ to 15 µm³) and red blood cells (6 µm³ to 8 µm³) during formation of the ultra-filtrate. For example, the outer layer 311 can be constructed with hydrophobic biomaterials or surface coatings that dissolve or slough when exposed to the high shear forces of flowing blood. In some embodiments, the sensor's power source (battery) and electronics can produce a negative, positive, or alternating electrical charge on the surface of the outer layer 311 and within the pore structure. The electric charge can inhibit the adhesion of plasma proteins, platelets, WBC, RBC, fibrin and thrombus on the outer membrane surface and keep the pores patent for years. In other embodiments, as shown in FIG. 4A, the outer layer of the vascular porous catheter can be surface coated with nitric oxide, heparin, fractionated heparin, prostacyclin antagonists ($PGI_2$, P2Y12 antagonists, cyclooxygenase-1 inhibitors (COX1), NSAID, Aspirin), CD39, endothelial-ADPase, and other inhibitors of platelet adhesion and degranulation such as GPIb/IX/X; GPVI; GPIIb/IIIa CD62, CD63 inhibitors (abciximab, eptifibatide, tirofiban, oprelvekin, romiplostim, eltrombopag) and synthetic endothelial cell glycocalyx (negatively charged proteoglycans, glycoproteins, and glycolipids).

When used in the bloodstream, the flexible catheter's outer layer 311 can also be coated with BAM (alloy of aluminum, magnesium, and boride: AlMgB14-TiB2), diamond-like-carbon, graphene, or PTFE because they have a very low coefficient of friction, are self-lubricating, and are highly hydrophobic. A membrane coated with 2-3 micrometers of BAM, diamond-like carbon, graphene, or PTFE may significantly inhibit the adhesion of platelets, red blood cells, white blood cells, and plasma proteins such as albumen and fibrin. Platelets, cells and proteins that do adhere to the catheter surface may break loose (loss of adhesion) due to the rapid blood flow and shear forces within a large blood vessel lumen such as the vena cava.

Referring back to FIG. 3B, the middle layer 313 can include a plurality of pores 323 designed to produce an ultra-filtrate of tissue fluid (ISF) or blood (plasma), such as through a hydrostatic pressure differential. The pores can be, for example, between 5 and 100 nanometers and have a density, for example, of between 2,000 and 10,000 pores/mm². The pores 323 of the middle layer may be significantly smaller than the pores 321 of the outer layer 311. The pores 321 of the outer layer 311 may be highly inter-connected with the pores 323 of the middle layer 313 such that water, sodium, chloride, and glucose can easily pass through the entire micro-fluidic system with minimal resistance.

Water (MW 18 grams/mole, 18 Daltons, 2.75 angstrom diameter) and glucose (MW 180 grams/mole, 180 Daltons, and 8.4 angstrom diameter) easily pass through pores with a diameter of 5 to 10 nanometers due to their very small size and neutral electric charge. Larger molecules like albumen (MW 66,400 Daltons and 7.5 nm×6.5 nm×4 nm diameter) and insulin (MW 5,600 Daltons and 35 angstroms×50 angstroms diameter) have greater difficulty moving through a small pore membrane (for example 5 to 10 nanometers) due to additional mechanical and electrical interferences. Cells and platelets will not pass through small pores with a 5 to 10 nm diameter.

Middle membrane layers 313 with larger pore sizes, larger pore density, and greater pore connectivity facilitate more rapid formation of ultra-filtrate from blood or tissue fluid. These high-flux membranes (manufactured of polysulfone, polyacrylonitrile, poly methyl-methacrylate, poly ether-sulfone, polyamide and cellulose) can facilitate a rapid rate of water flow/flux and the passage of larger molecules (20,000 to <50,000 MW or Daltons). Commercial PAN fibers (AN-69) have a 30,000 Dalton average pore size (cut off).

One embodiment of the middle layer 313 may be manufactured with a thin polyamide small pore membrane (5 to 500 nm pore diameter and 200 to 500 nanometers thick) laminated to a thicker membrane of polyethersulfone or polysulfone (100 to 1000 nm pore size and 50 to 200 micrometers thick). An alternate embodiment of the middle layer 313 may have larger pore sizes (>500 nm diameter) to facilitate more rapid formation of ultra-filtrate from blood plasma or tissue fluid. Membranes with a larger pore size are called high-flux membranes (manufactured of polysulfone, polyacrylonitrile, PAN fibers (AN-69), poly methyl-methacrylate, poly ether-sulfone, polyamide and cellulose) because they facilitate a more rapid rate of water flow/flux and the passage of small and larger molecules (20,000 to 50,000 MW cut off).

Exemplary embodiments of the middle layer 313 can be manufactured with a micro- or nano-electromechanical system (MEMS/NEMS) structure with precise pore size, shape, density, thickness, pore connectivity, surface chemistry, texture, biomaterials, and electric charge. Photolithography (similar to computer chip manufacturing) can be used to produce a precise pore or channel size (such as 5 to 10 nm or range 5 to 500 nm), shape (round, oval, square, rectangle, or slit) density (low, medium, and high) and thickness (5 to 100 micrometers). In some embodiments, a small wavelength laser can be used to produce small holes or micropores (for example 5 to 500 nanometer diameter) within the middle layer 313.

Water, glucose, and electrolytes will readily pass through a MEMS/NEMS membrane with a pore diameter of 5 to 10 nanometers. Water, glucose and other small molecules easily move in and out of capillary endothelial cells of continuous and fenestrated capillaries. Continuous capillaries typically have small pores or channels (mean diameter 6 nm and 1 to 12 nanometer range) and larger pores or channels (24 to 60 nanometer diameter). Glucose and water will move more slowly through smaller diameter porous membranes (0.1 to 0.25 nanometers) due to molecular size and the surface tension of water (high resistance to flux).

Referring to FIGS. 5A and 5B, in some embodiments, the middle layer 313 can include a plurality of hollow micro-needles 333 (also called posts, extensions, or villi) with an open interconnecting micro-fluidic structure extending from a base membrane 335. The micro-needles 333 can have a rounded, flat, or sharp tip. In some embodiments, photolithography can be used to produce micro-needles 333 that include single or branching formation, as discussed further below. The micro-needles 333 can rise at a right angle or obtuse angle relative to the base membrane 335 and can significantly increase the total surface area of the middle layer 313 that is in contact with the surrounding vascular tissue. The micro-needles 333 can extend at a variety of different heights up into the outer layer 311, as shown in FIG. 5A, thereby increasing the amount of contact with the surrounding vascular tissue. Thus, the orifices of the middle layer's micro-fluidic system can be broadly distributed throughout the three-dimensional (3D) volume of the surrounding vascular tissue.

A negative hydrostatic pressure applied to the middle or lumen of the flexible porous catheter (most proximal portion of the micro-fluidic system) can be broadly distributed throughout the 3D volume of the vascular tissue within the outer layer 311. Therefore, tissue fluid (ISF) can be actively transported from a large 3D volume of surrounding vascular tissue rather than limited to only one 2D plane of the vascular tissue. The increased contact area with the vascular tissue can advantageously ensure that more body fluid (i.e., interstitial fluid) is filtered through the pores/channels of the branching micro-fluidic system into the lumen of the flexible catheter, thereby helping to ensure effective real-time monitoring of analyte levels in the fluid. Moreover, the biomaterial of the outer porous layer 311 can adhere to the micro-needles 333 to enhance mechanical adhesion/attachment and prevent membrane delamination.

Figure 6:
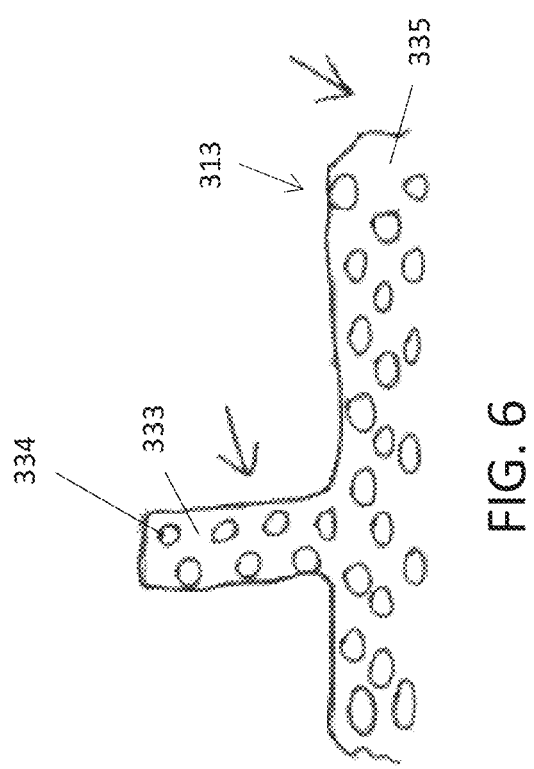
FIG. 6 shows a portion of a middle layer of a porous catheter with a porous microneedle extending therefrom.

As shown in FIG. 6, the micro-needle 333 of the micro-fluidic system can be constructed with one or numerous micro-pores/channels/orifices 334 that significantly increase the number of pores/channels/orifices per area in direct contact with adjacent vascular tissue. A membrane that includes pores/channels/orifices 334 on the micro-needles 333 and/or between the micro-needles 333 greatly increases the number of pores and the distribution of pores throughout the vascular tissue within the outer layer 311 (similar to villi and micro-villi on the wall of the intestines). The micro-needles 333 can be textured and shaped like a cylinder, mushroom, or branched shape to enhance the 3D distribution surface area for the mechanical adhesion of the outer membrane to this membrane.

Referring to FIG. 7, in some embodiments, there can be groups of micro-needles 333a, b, c, and d, where each group has micro-needles of different lengths. Each of the different length micro-needles 333a-d can then form a pattern on the base membrane 335. For example, there can be a pattern that runs (where 333d is 1, 333c is 2, 333b is 3, and 333a is 4): 1-2-3-4-3-2-1-2-3-4-3-2-1 and continues in horizontal and vertical directions. The pattern can be chosen to provide the optimal distribution of the micro-needle's orifices/pores/channels 333 within the 3-D volume of the vascular tissue.

Figure 9:
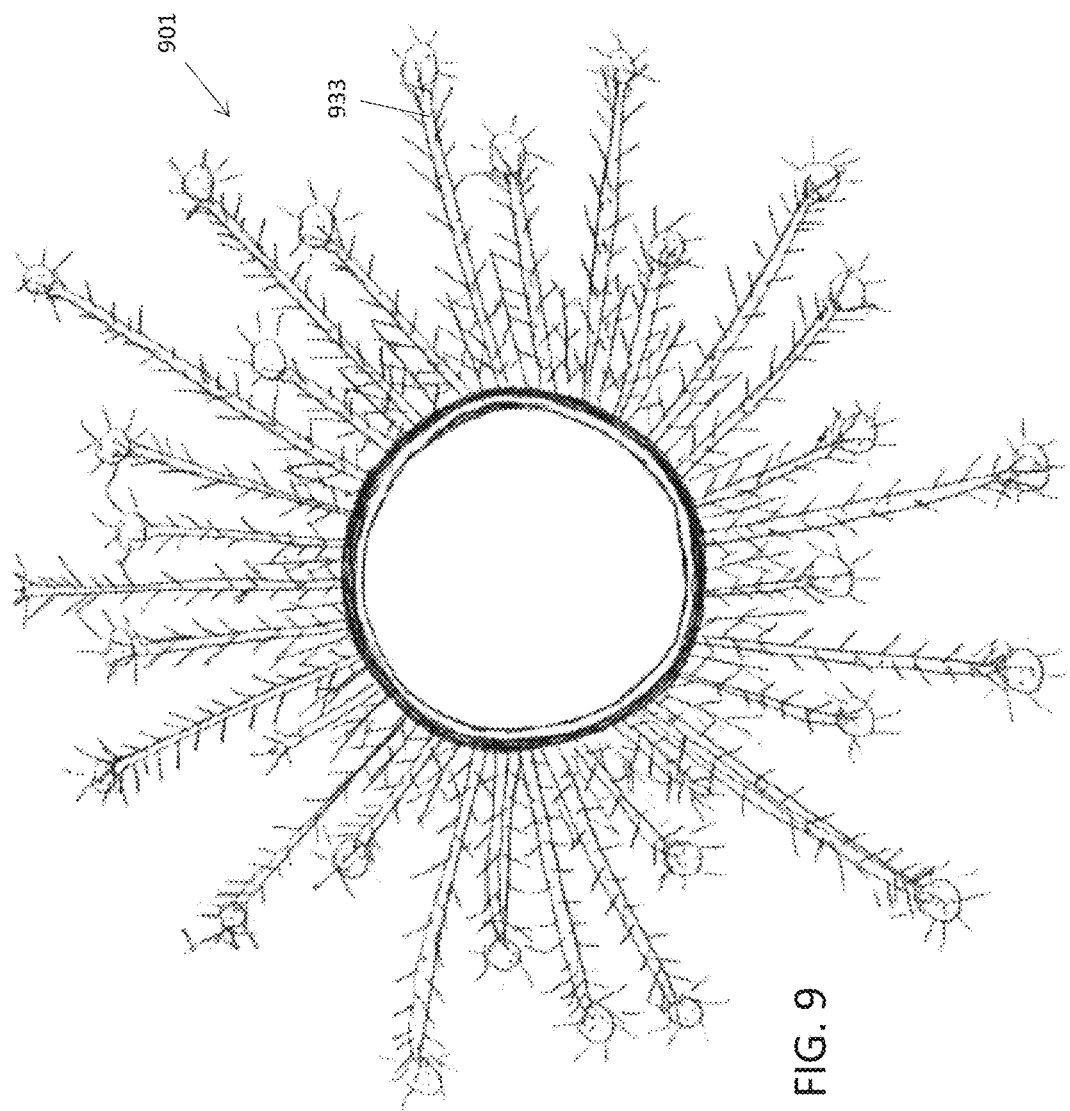
FIG. 9 shows a cross-section of a porous catheter including branching microneedles extending from the middle layer.

Further, referring to FIGS. 8A and 8B, in some embodiments, the micro-needles 333 can include a branching formation, i.e., similar to the branching pattern of an evergreen tree or a snow flake. The branching micro-fluidic system with interconnected lumens can advantageously increase the number and location of the ultra-filtrate forming orifices/pores/channels with the surrounding vascular tissue, thereby increasing the reliability of ultra-filtrate formation and the speed through which body fluid (ISF) is transformed into ultra-filtrate and transferred to the flow-through sensor. For example, the system can be configured to produce 2-10 microliters of ultra-filtrate per minute with a time lag between the entrance of the fluid into the porous catheter to obtaining a sensor reading in less than 10 minutes, such as less than 5 minutes, less than 4 minutes, or less than 3 minutes. In one embodiment, the entire lumen of the micro-fluidic system leading up to the flow-through sensor is only 10 to 20 microliters of dead space. Referring to FIG. 9, one embodiment of a porous catheter 901 includes a plurality of micro-needles 933, each of the micro-needles having a branching formation with interconnected lumens to form a micro-fluidic system.

Figure 10A:
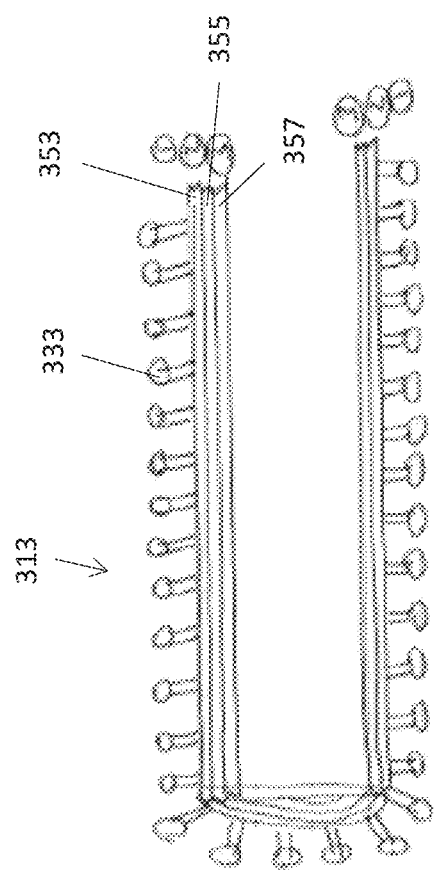

Referring to FIGS. 10A and 10B, in some embodiments, the middle layer 313 can include a plurality of sublayers 353, 355, 357. The outer sublayer 353 can include the MEMS/NEMS porous membrane and micro-needles 333 discussed previously. The middle sublayer 355 can be an additional membrane that has smaller pores (such as 5 to 100 nanometers) than the outer sublayer 353. For example, the middle sublayer 355 can be a spun fiber or nanotube with a structure similar to a silk cocoon. Finally, the inner sublayer 355 can be another layer with pores. Thus, the middle sublayer 355 can be sandwiched between two similar sublayers 353, 357. This sandwich design can closely mimic the three layers of the glomerulus of the kidney. The porous structure of the outer sublayer 353 membrane can mimic the pores of the endothelial cells, the middle sublayer 355 can be constructed to mimic the structure and function of the glomerulus basement membrane, and the porous structure of the inner sublayer 357 can mimic the pores/slits of the podocyte cells.

Figure 11:
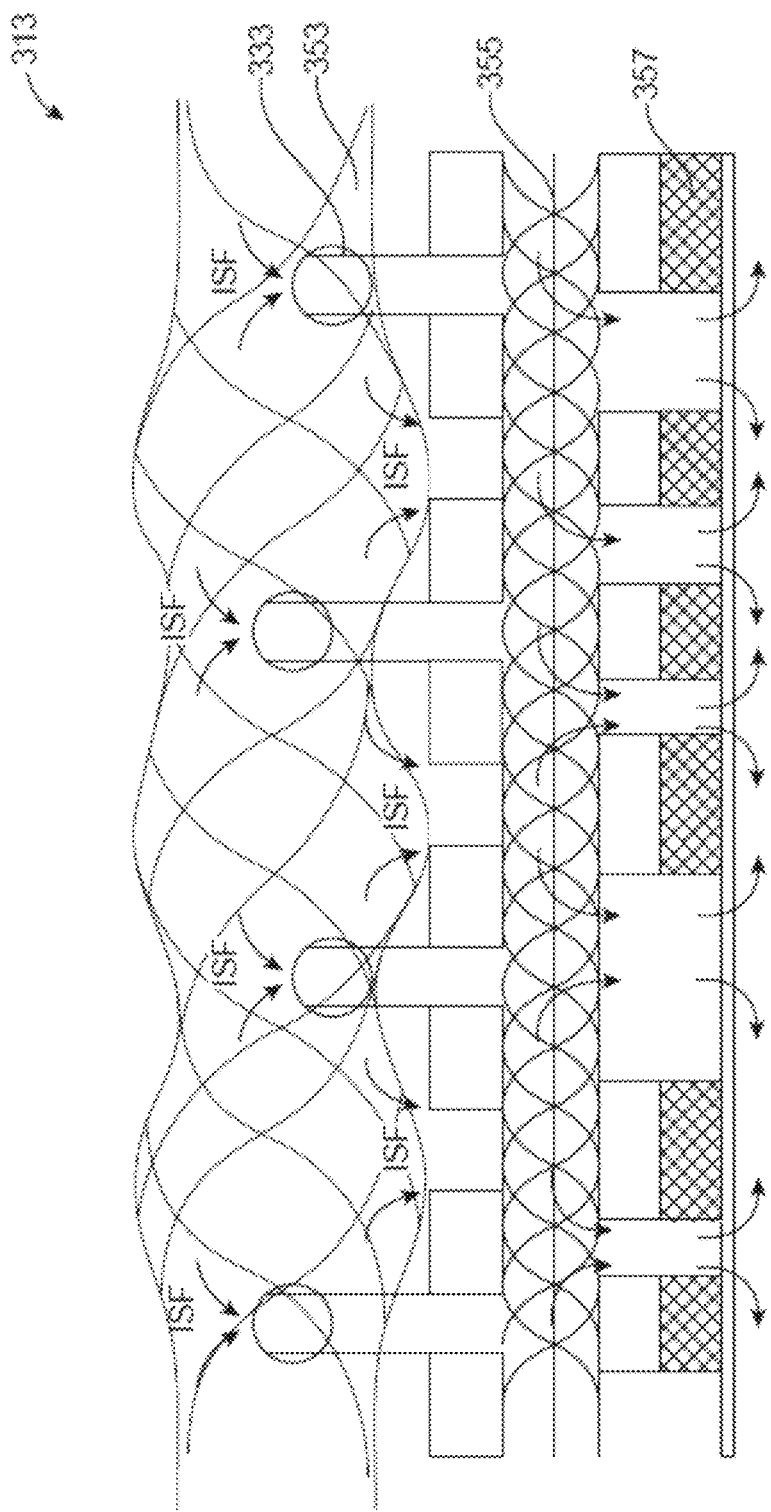
FIG. 11 shows a middle sublayer of a porous catheter with an enzyme therein.

Referring to FIG. 11, in some embodiments, the middle sublayer 355 can include an enzyme, such as glucose oxidase (GOx) enzyme, therein. When the pump (e.g., battery powered pump) is activated, water, sodium, chloride, glucose, and other small molecules can be actively moved from the tissue fluid (ISF) through the middle sublayer 355. Glucose, oxygen, water, and salt molecules within the ultra-filtrate are actively transported (via the hydrostatic pressure differential) through the pores/channels of the outer sublayer, to interact with the GOx enzyme within the middle sublayer (as shown by the arrows in FIG. 11). The glucose/glucose oxidase redox reactions produce hydrogen peroxide and additional electrons in direct proportion to the ultra-filtrate glucose concentration. The electrochemical glucose sensor's working electrode, counter electrode, and reference electrode can be integrated into the porous structure of the inner sublayer or within an adjacent flow-through sensor. In contrast to current commercial glucose oxidase electrochemical glucose sensors that depend upon passive diffusion of glucose and oxygen to interact with the GOx and working electrode, this embodiment uses a battery powered pump to actively transport the ultra-filtrate containing glucose and oxygen to interact with the GOx enzyme and working electrode at a rate much faster than simple diffusion.

Further, in one embodiment, the middle sublayer 355 can be manufactured of nanometer sized carbon nanotubes, graphene, polymer fibers, or basement membrane connective tissue fibers that are spun or weaved into an interconnecting mat-like structure. The nano-fibers can be spun into a tight structure with small spaces between the fibers. This mesh-like structure can prevent the ingrowth of cells and connective tissue while permitting the rapid movement of water, glucose, and electrolytes from once side to the other side, with minimal resistance to flow, similar to the basement membrane of the glomerulus and capillary endothelial cells.

The middle layer 313 and sublayers can be coated with BAM, diamond-like-carbon, graphene, or PTFE because they have a very low coefficient of friction, are self-lubricating, and are highly hydrophobic. BAM has a coefficient of friction of 0.02, diamond-like carbon 0.05, and PTFE 0.05 to 0.1 (compared with polished stainless steel of 1.0). A membrane coated with 2-3 micrometers of BAM, diamond-like carbon, graphene, or PTFE will significantly enhance the flow/flux of water, glucose, and electrolytes through the pores and prevent the adhesion of cells and protein within the porous structure. The ceramic alloy of Aluminum, Magnesium, and Boride (BAM) is highly resistive to wear and has the lowest coefficient of sliding friction of any material (0.02AlMgB14-TiB2).

Figure 12:
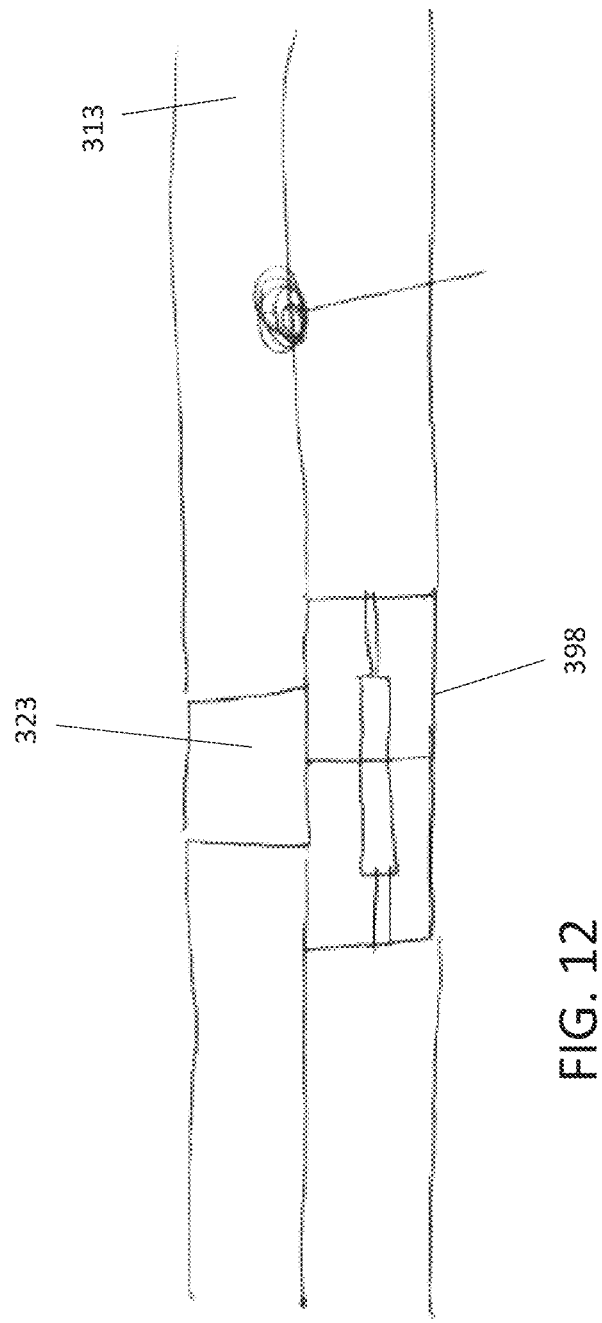
FIG. 12 shows a middle layer of a porous membrane with a valve or gate in a pore to control the flow of fluid therethrough.

The pores 323 of the middle layer 313 can be wide open, have a taper, have a reverse taper, be shaped as an hourglass, and/or form a tortuous path or a slit. Further, in some embodiments, referring to FIG. 12, the pores 323 can include one or more MEMS/NEMS valves or gates 398, which can be one-way valves or two-way valves. The valve or gate 398 can, for example, be electronically controlled to allow fluid in and out of the pores 323. A negative, positive, or alternating electric charge can be applied to the valve or gate surface to enhance or inhibit the flow of charged molecules to the opposite side of the porous membrane.

The rate of ultra-filtrate formation can depend upon the characteristics of the middle layer 313. In some embodiments, the ultrafiltration formation can be slow (0.5 to 1 ul/minute), medium (1 to 2 ul/min or 1 to 5 ul/minute) or fast (>5 ul/minute). The rate will depend, for example, upon the total area of micro-porous membrane surrounded by vascular tissue, pore size, pore density, membrane thickness, material, charge (sieve coefficient of the porous membrane), local capillary blood flow, sieve coefficient of the capillaries, and Starling Forces of the local capillary vessels.

The Starling equation defines the forces across a semi-permeable membrane and allows calculation of the net flux:

$$J_v = K_f ([P_c - P_i] - \sigma[\pi_c - \pi_i])$$

where $([P_c-P_i]-\sigma[\pi_c-\pi_i])$ is the net driving force, $K_f$ is the proportionality constant, and $J_v$ is the net fluid movement between compartments.

By convention, outward force is defined as positive, and inward force is defined as negative. The solution to the equation is known as the net filtration or net fluid movement (Jv). If positive, fluid will tend to leave the capillary (filtration). If negative, fluid will tend to enter the capillary (absorption).

In some embodiments, the sensor's power source (battery) and electronics can produce a negative, positive, or alternating electrical charge on the surface of the outer layer 311 and within the pore structure. The electric charge can be used to enhance or inhibit the flow of water, glucose, and electrolytes through the membrane pores. The electric charge can also be used to inhibit the adhesion of plasma proteins, platelets, WBC, RBC, fibrin and thrombus on the biomaterial surface and keep the pores patent for years.

Figure 13:
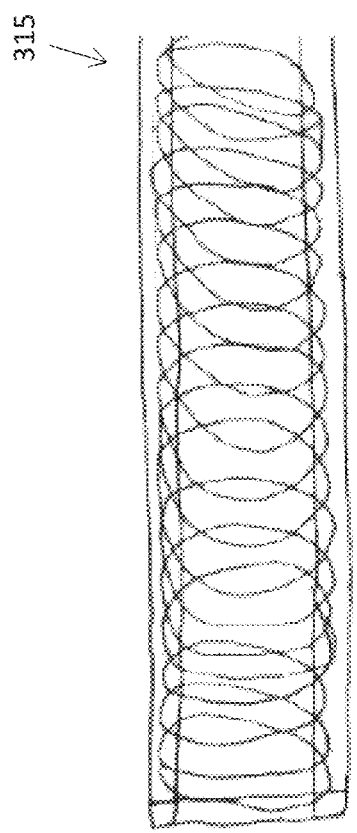
FIG. 13 shows an inner layer of a porous catheter.

Referring to FIG. 13, the inner layer 315 can be configured to provide structural support to the middle and outer layers 313, 311 of the porous catheter to avoid compression due to applied negative pressure by the MEMS/NEMS pumps and/or external compression. The inner layer 315 can be manufactured from metal, ceramic, plastic, or composite materials with a mechanical structure that resembles a stent, spring, catheter, disc, ball, or cylinder with multiple holes. The inner layer 315 should be strong enough to support the middle and outer layers 311, 313 and avoid compression due to external forces or negative pressure (vacuum) produced by the MEMS/NEMS pumps.

In one embodiment, referring to FIGS. 14A-14B, the inner layer 315 can include a spring 1401 that is configured to change shape with a change in temperature or electric current. This control mechanism can make the inner layer's spring to tighten (as shown in the change from FIG. 14A to 14B) or loosen (as shown in the change from FIG. 14B to 14A), leading to an increase or decrease in the rate of ultra-filtrate flow.

In one alternate embodiment, the middle membrane has sufficient enough mechanical strength to avoid compression due to external forces or negative pressure (vacuum) caused by the MEMS/NEMS pumps, such that an inner layer 315 is not necessary.

Referring to FIGS. 15 and 15A, the micro-fluidic system can include bulbs 1522 on the distal end (i.e., the end furthest away from the central module 103) of one or more of the flexible catheters 1501. Bulbs can be located on the end of a large flexible catheter and/or located on distal branches of the micro-fluidic system. The bulbs 1522 can include a plurality of pores 1534 therein. The bulbs 1522 with pores 1534 can advantageously increase the number and surface area of pores exposed to the vascular tissue's interstitial fluid (ISF).

Each implant can include one or more mechanical fluid pumps, such as a battery powered fluid pump, that is configured to produce the desired pressure differential. Referring to FIGS. 16A and 16B, a pump 107 for use in any of the implants described herein can be, for example, a MEMS/NEMS fluid pump. Photolithography methods can be used to produce a miniature, reliable, low power MEMS/NEMS fluid pump using materials that do not degrade or fail when exposed to an ultra-filtrate of body fluids long-term.

As shown in FIGS. 16A-16B, the MEMS/NEMS pump 107 can include a fluidic system with a diaphragm 177 that moves inward/outward a fixed stroke volume (for example 0.1 ul/stroke). The number of strokes or vibrations per minute can determine the volume of fluid pumped per minute (for example, 0.1 ul/stroke×100 strokes/minute=10 ul/minute flow). MEMS/NEMS valves 188a and 188b can maintain a steady fluid flow in one direction or both directions.

The pump 107 can produce a lower hydrostatic pressure on the inlet side and a higher hydrostatic pressure on the outlet side. The amount of hydrostatic pressure can be calculated as Pressure=Flow×Resistance. Thus, the greater the number of strokes per minute by the MEMS/NEMS pump, the greater the flow of fluid, and the greater the hydrostatic pressure differential.

Thus, for example, the pump 107 can be used to produce a lower hydrostatic and oncotic pressure (negative pressure) on the inside of the micro-porous catheter(s) relative to the higher hydrostatic and oncotic pressure external to the catheter (e.g., through Starling Forces). Referring back to FIG. 1, the pump 107 can thus create a pressure differential such that the hydrostatic pressure outside of the porous catheter 101a is higher than the hydrostatic pressure inside of the porous catheter 101a, which is higher than the hydrostatic pressure inside of the sensor 105, which is higher than the hydrostatic pressure inside of the porous catheter 101b, which is higher than the hydrostatic pressure outside of the porous catheter 101b.

The pump 107 can be configured to maintain a constant flow of ultra-filtrate through the porous membranes and sensor despite dynamic changes in the hydrostatic pressure and oncotic pressure of the vascular tissue located within the porous membrane's outer layer. The vascular tissue environment may change dynamically due to changes in the tissue composition, hydration status, nutrition status, body position, external compression, capillary blood flow, capillary filtration coefficient, temperature, and atmospheric pressure.

Figure 17:
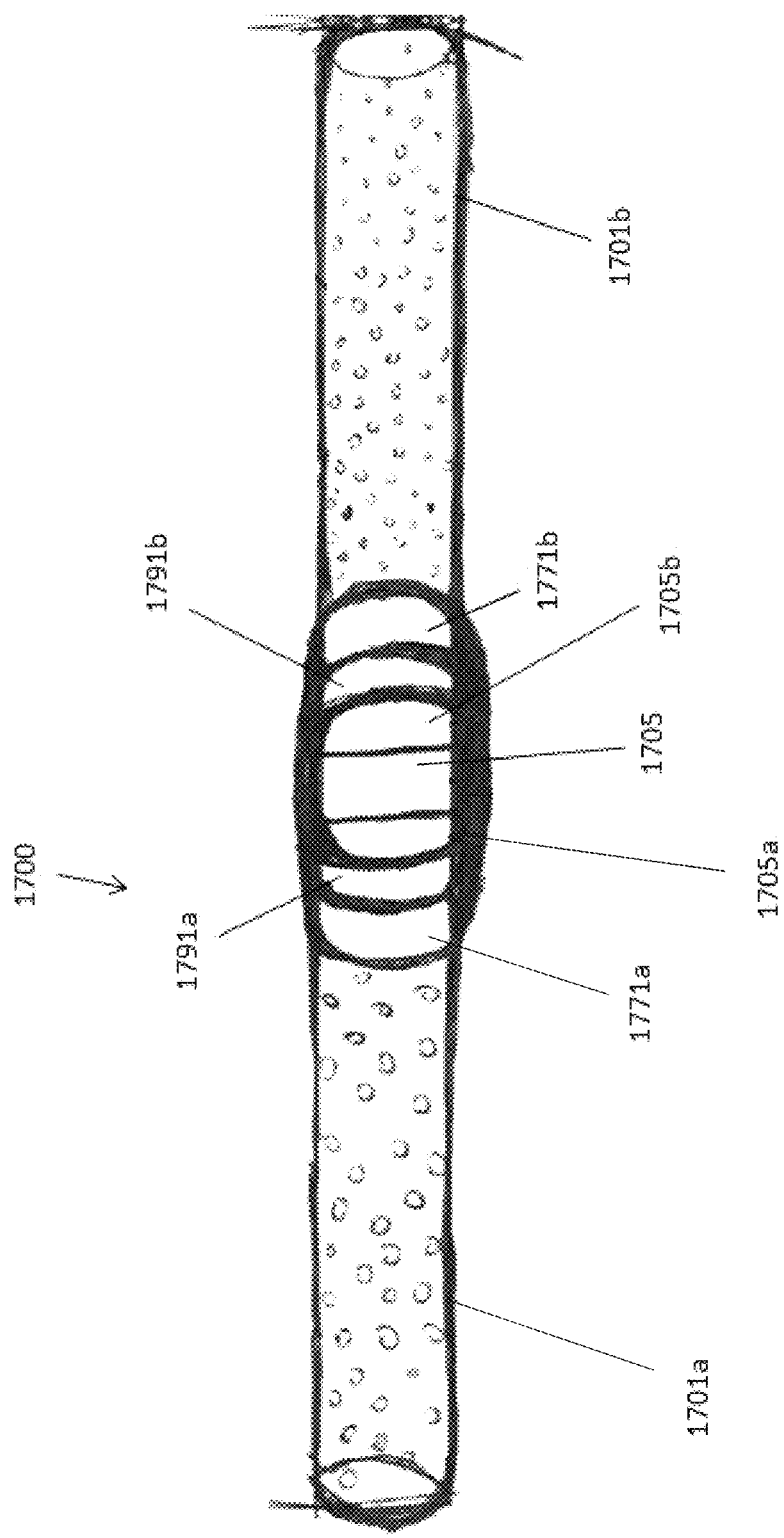
FIG. 17 shows an implantable glucose monitoring system with pressure sensors therein.

In some embodiments, referring to FIG. 17, the implant 1700 can be configured to measure and maintain the hydrostatic pressure differential at a constant level. For example, the implant 1700 can include pressure sensors 1771a and 1771b configured to measure the pressure before and after the analyte sensor. The pumps 1705a and 1705b can thus be used to pull fluid in through porous catheter 1701a, through the sensor 1771a, through the sensor 1705, through sensor 1771b, and out through catheter 1701b. Valves 1791a and 1791b can be used to ensure the proper direction of flow through the implant 1700. A controller connected to the pressure sensors 1771a and 1771b can control the pumps 1705a and 1705b so as to maintain a constant pressure differential despite dynamic changes in the hydrostatic pressure, oncotic pressure, and external pressure or blood pressure that surrounds the implant.

The pump system and controller can be designed to maintain a steady flow of ultra-filtrate (for example 1-4 µl/minute) through the sensor using the lowest hydrostatic pressure differential required to produce the desired flow rate (to conserve battery power). For example, a small pressure differential may be required to produce a continuous 2 µl/minute flow of ultra-filtrate in an ambulatory patient that is well hydrated, while a larger pressure differential may be required if the patient is dehydrated or the porous membrane develops an increased resistance to fluid flow.

The long-term functioning of the implantable ultra-filtrate monitoring system may be based on the ability of the pump to maintain a steady flow or flux of water, glucose, electrolytes and other small molecules from the interstitial fluid or plasma into the inner lumen of the micro-porous membrane. The ultra-filtrate is formed due to net hydrostatic and oncotic pressures within the plasma/tissue fluid relative to the inside of the micro-porous membrane. The level of negative hydrostatic pressure (vacuum pressure) can control the flow or flux of water and glucose through the micro-porous membrane, according to the Starling equation.

In some embodiments, in order to reduce clogging of the pores of the porous catheters (e.g., caused by large molecules and cells), the pump system can be configured to intermittently reverse the pressure differential such that fluid flows in the opposite direction. Thus, for example, if a hydrostatic pressure differential is first created from the first tissue's ISF (P1) to the inside of the first porous membrane (P2) to the inside of the flow-through sensor (P3) to the inside of the second porous membrane (P4) to the second tissue's ISF located outside of the second porous membrane (P1>P2>P3>P4>P5), then the pressure differential can be reversed such that (P5>P4>P3>P2>P1) such that ultra-filtrate can flow from the second tissue's ISF, through the flow-through sensor, into the first tissue's ISF.

In some embodiments, the flow can be reversed by reversing the motor within the pump. In other embodiments, a rotary valve can be used to automatically reverse flow after a set amount of time. For example, referring to FIG. 15, the flexible porous catheters 1501 can be connected to a rotary valve 1525, such that the ultra-filtrate from some of the catheters can be flowing into the sensor (inlet catheters) and ultra-filtrate from other catheters can be flowing out of the sensor (outlet catheters) into the adjacent vascular tissue. The valve 1525 can rotate at set intervals so that an inlet catheter becomes an outlet catheter one or times every day. This method can decrease mechanical obstruction of the porous membrane (biofouling) similar to backwashing the filter of a swimming pool.

The pump can be any type of pumping mechanism, including peristaltic, piston, gear, lobe, screw, progressive cavity, impeller, centrifugal, diaphragm, or pressurized reservoir and power mechanisms including an electromagnetic coil, piezoelectric device, electrolysis or osmotic pressure.

Referring back to FIG. 1, the sensor 105 can be used to determine an amount of analyte, such as glucose, in the ultra-filtrate. One or more sensors can be used in a single implant. The micro-fluidic system of the implanted sensor can be configured to have low dead space to minimize lag time between a change in analyte concentration in the blood/interstitial fluid and a change in the ultra-filtrate analyte concentration measured at the sensor. In one embodiment, the implant produces a large amount of ultra-filtrate per minute and transports the ultra-filtrate rapidly through the micro-fluidic system to the flow-through sensor.

To minimize time-lag, the internal volume of the flexible porous catheter's that delivery ultra-filtrate to the sensor (inlet catheters) can have a volume of less than 20 microliters. Thus, the internal diameter of the inlet porous catheter(s) of the micro-fluidic system can be very small to minimize the dead space volume and the time-lag from a change in blood level to a change in sensor level.

The sensor 105 can be a flow-through sensor that monitors the chemical concentration and/or physical composition of the solution (i.e., glucose, insulin, c-peptide, lactate, pyruvate, glycerol, beta-hydroxy butyrate, aceto-acetic acid, acetone, fatty acids, triglycerides, cholesterol, electrolytes, BUN, creatinine, liver enzymes (LDH, SGOT), pH, oxygen, carbon dioxide, bicarbonate, osmolarity, markers of tissue ischemia/infarction (CPK, troponin), tumor markers (dysplasia and neoplasia), hormones, markers of inflammation, growth factors, cytokines, drug levels, vitamin levels, etc.). The porous catheter's membranes may be optimized for analytes that are small, hydrophilic, with a neutral charge. Analytes that are larger, hydrophobic, and/or charged may need a porous membrane with alternate characteristics.

The ultra-filtrate analyte sensor 105 can be, for example, an optical sensor, a differential oxygen sensor, an enzyme/electrochemical sensor, a fluorescence sensor, or a physical change sensor.

In one preferred embodiment, an optical sensor can use near-infrared spectroscopy, mid-infrared spectrometry, and/or Raman spectroscopy to measure the concentration of analyte (glucose) in the ultra-filtrate fluid. The optical sensor can be used to measure the concentration of glucose with satisfactory accuracy and specificity because the ultra-filtrate fluid sample is clear and very simple, consisting of water, sodium, chloride, glucose, and a few other small molecules. For example, referring to FIGS. 18A and 18B, a flow-through optical sensor 180 can have light sources 1881a and 1881b and light detector 1883a and 1883b opposite each other with a short and fixed path length. Ultra-filtrate can flow through the small gap between the light source and detector (approximately 100 μm wide) to produce spectra with a high signal to noise ratio. Hundreds of spectra can be measured and averaged in less than a few seconds. The patient's spectra can be compared to a universal calibration algorithm to measure the concentration of ultra-filtrate glucose with satisfactory accuracy and specificity. The flow-through optical sensor 1800 may also contain a thermistor that continuously measures ultra-filtrate temperature to compensate for the effects of temperature on the optical spectra measurement.

Advantageously, optical sensing methods do not produce byproducts that are toxic or otherwise harm the body or the implant.

In some embodiments, the implanted sensor can be intermittently calibrated using an external reference analyte sensor (for example a glucose meter and test strips). The measurement resulting from the external reference sensor and time-stamp can be transmitted to the implanted sensor using RF telemetry. The implanted sensor can have calibration algorithm that notifies the patient when an external calibration is required to ensure sensor accuracy.

The implant can include a controller or processor configured to control the sensor, the pump, and/or other features of the implant. In some embodiments, the controller and power source can be completely within the central module.

Figure 19:
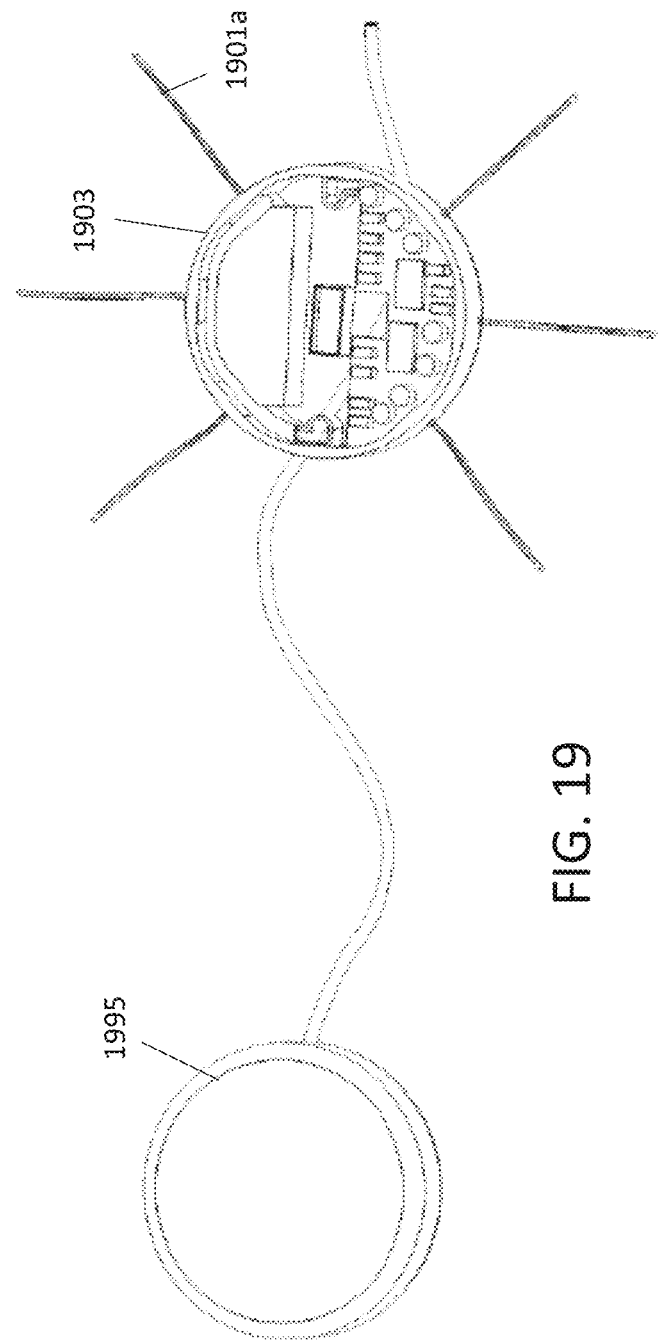
FIG. 19 shows a glucose monitoring implant having a central module and an external module.

Referring to FIG. 19, in some embodiments, the central module 1903 can include the sensor, pumps, some electronics, and micro-fluidic system while an external module 1995 can include the power source, electronics, antennae, and telemetry. The mass of the implanted central module is minimized to produce minimal tension on the soft, flexible microporous catheters and surrounding tissue. Thus, the central module can include only (the sensor and the pump) while another external module can include the battery, electronics, and telemetry.

In contrast, referring to FIG. 20, a smaller central module 2003 can include only the sensor, pump, and micro-fluidics system while the external module 2095 can include all of the electronics and power source.

Figure 21:
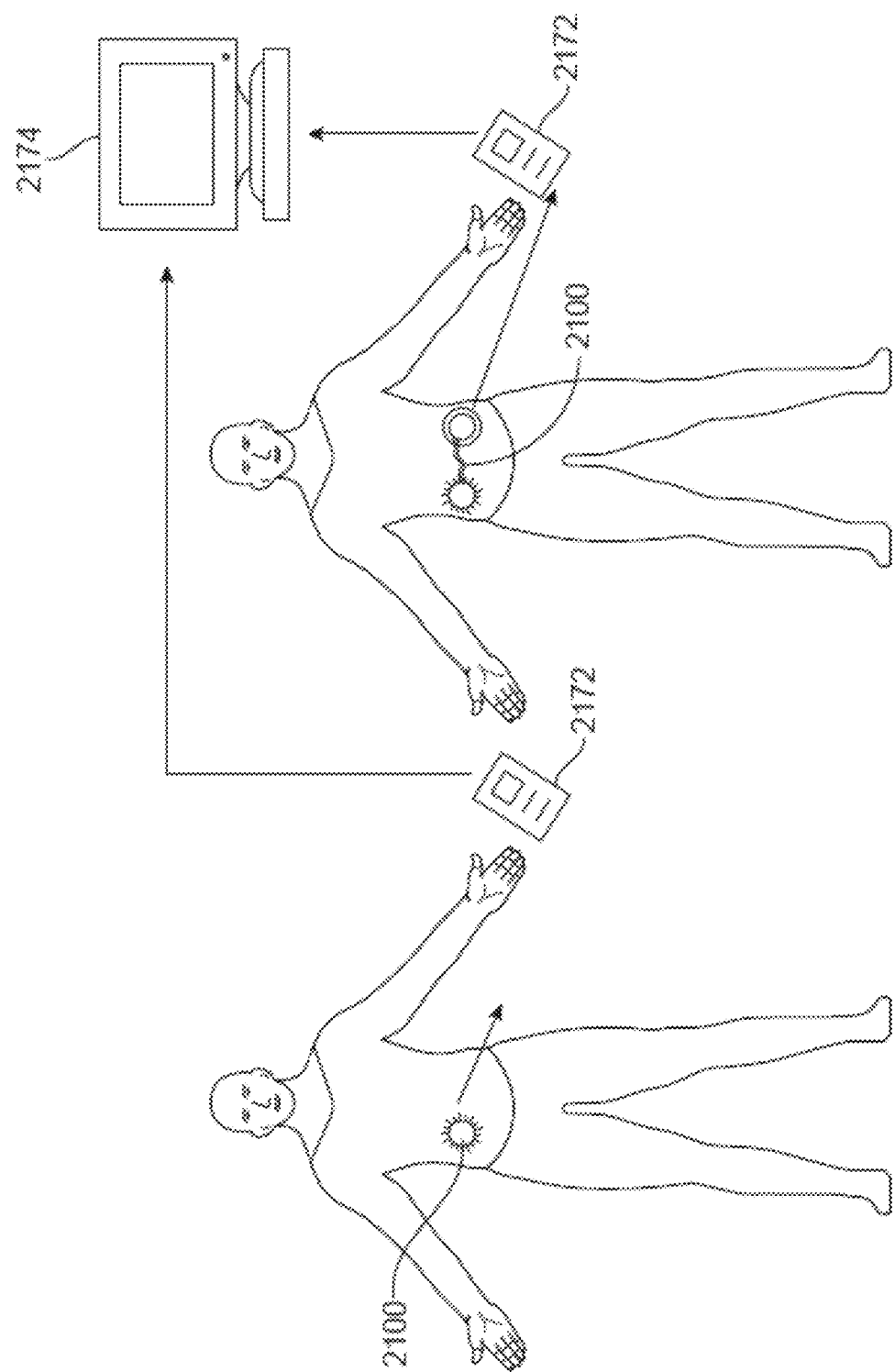
FIG. 21 shows the connection of a glucose monitoring implant to an external module and/or a remote monitoring system.

Further, referring to FIG. 21, in some embodiments, the implant 2100 can connect to a remote module 2172, such as through telemetry. The remote module 2172 can include a display configured to show, for example, the amount of analyte detected. Further, the remote module 2172 can be connected to a central or second remote module or monitoring station 2174. In some embodiments, the implant can be connected to a phone or other personal or professional device to display information related to the analyte levels.

The external module 2172 can include a display, programmable alarms, and/or an accurate blood glucose meter with test strips to produce a timely blood glucose measurement for calibration of the implantable glucose sensor.

The power source for the implant can be a long-term battery. In some embodiments, the battery can be rechargeable by a transcutaneous battery charger (for example, by induction coupling across the skin).

The implant controller can include closed-loop and/or semi-closed loop software algorithms. In some embodiments, the controller can include predictive algorithms with high sensitivity and specificity that alert and alarm for hyperglycemia, hypoglycemia, and rapid rate of change in the measured ultra-filtrate of interstitial fluid based upon readings from the sensor. In some embodiments, the controller can determine the optimal infusion dose of insulin/glucagon in an ambulatory patient with diabetes. The implantable sensor's algorithms can control a mechanical pump that delivers insulin and/or glucagon into the tissues or bloodstream of a diabetic patient.

The glucose monitoring systems described herein may monitor the glucose concentration during fasting, meals, exercise, and illness to determine the optimal infusion dose of insulin and/or glucagon. The diagnostic algorithms may consider the glucose concentration, current rate of glucose increase/decrease, recent past rate of glucose increase/decrease, models of insulin PK/PD, models of food absorption, and models of changing insulin sensitivity due to activity/exercise, illness, age, body temperature, meal size and meal composition.

The initial control algorithm parameters/constants can be adapted in real-time based upon the patient's glucose response to meals, exercise, rest, and insulin delivery. For example, the system may automatically calculate the body's insulin sensitivity (insulin pharmacodynamics) prior to the morning meal by infusing 1 unit of insulin; then monitor the change in the glucose concentration over the next 60 minutes. The absolute change in the glucose concentration, the rate of change, the time to peak effect, and the time to return to baseline will be modeled to determine the current insulin sensitivity.

The control algorithms may combine Proportional Integral Derivative (PID), Proportional Derivative (PD), and Model Predictive Control methods. The System control algorithms can automatically maintain the blood glucose concentration in the target range, despite dynamic changes in patient physiology, external environmental factors (meals, exercise, and illness) and system performance. The system controller software and control algorithms can be within the implanted monitoring system or within the External Electronics Module.

The diagnostic algorithms can provide predictive and threshold alarms for hyperglycemia and hypoglycemia with high sensitivity and specificity. A system with the above characteristics may be able to eliminate or reduce moderate/severe hyperglycemia, moderate/severe hypoglycemia, and minimize glycemic variability.

The implanted monitoring system can communicate with an external electronics module via telemetry. The external module can be a smart cell phone with a large color display and an integrated glucose meter to facilitate re-calibration. The external module can have programmable alerts and alarms for hyperglycemia, hypoglycemia, and rapid rate of glucose change.

Figure 22A:
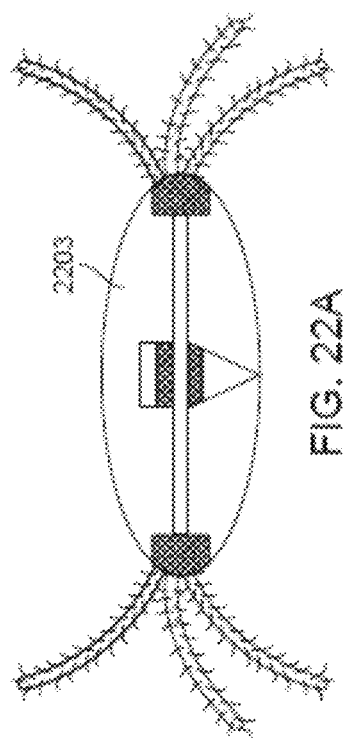
FIGS. 22A-D show different shapes of a central module of a glucose monitoring system.
Figure 22C:
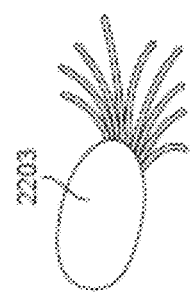
Figure 22B:
Figure 22D:
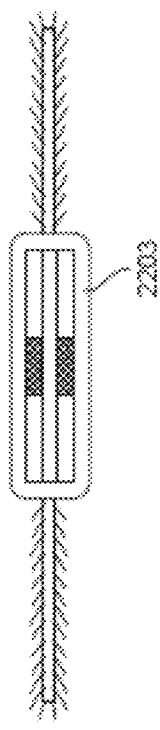

In some embodiments, referring to FIGS. 22A-D, the long-term implantable interstitial monitoring system is shaped like a flat disk (FIG. 22D), rounded disc (FIG. 22A), golf ball, football (FIG. 22A), or pear (FIG. 22D). Further, referring to FIGS. 23A-B, the central module 2303 can be shaped like a star.

Figure 24A:
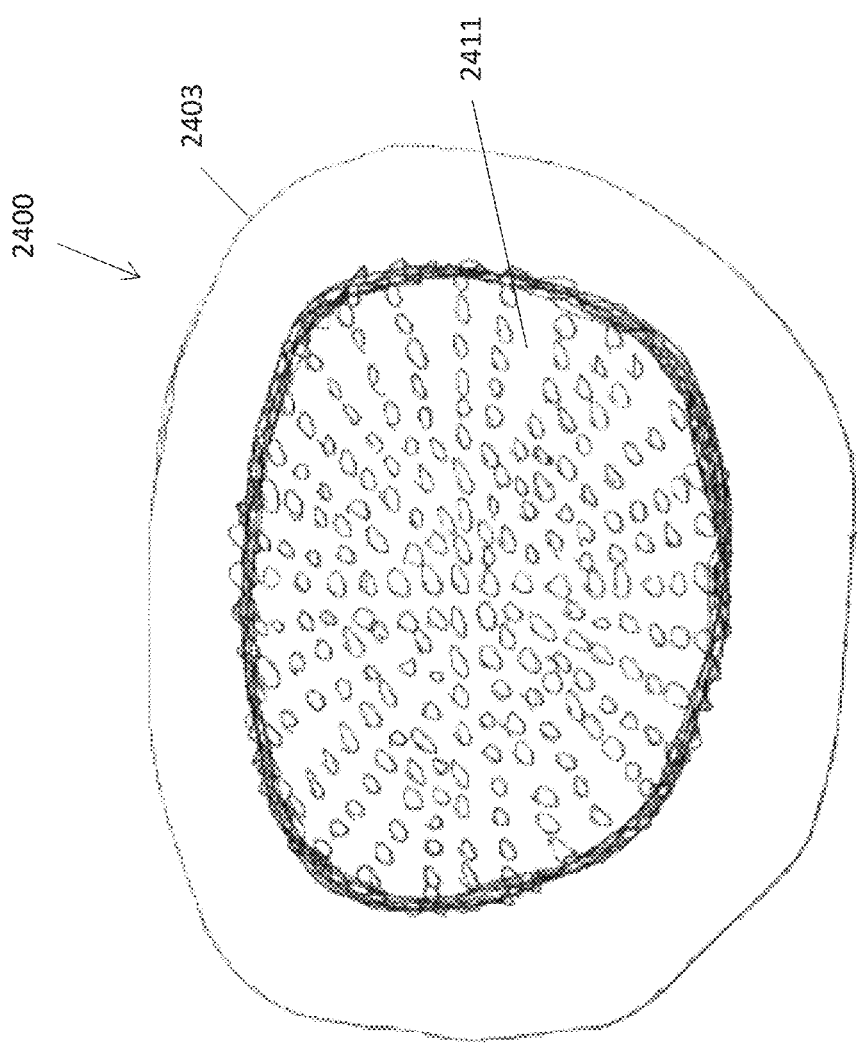
FIGS. 24A-B show another embodiment of a glucose monitoring system without catheters.
Figure 24B:
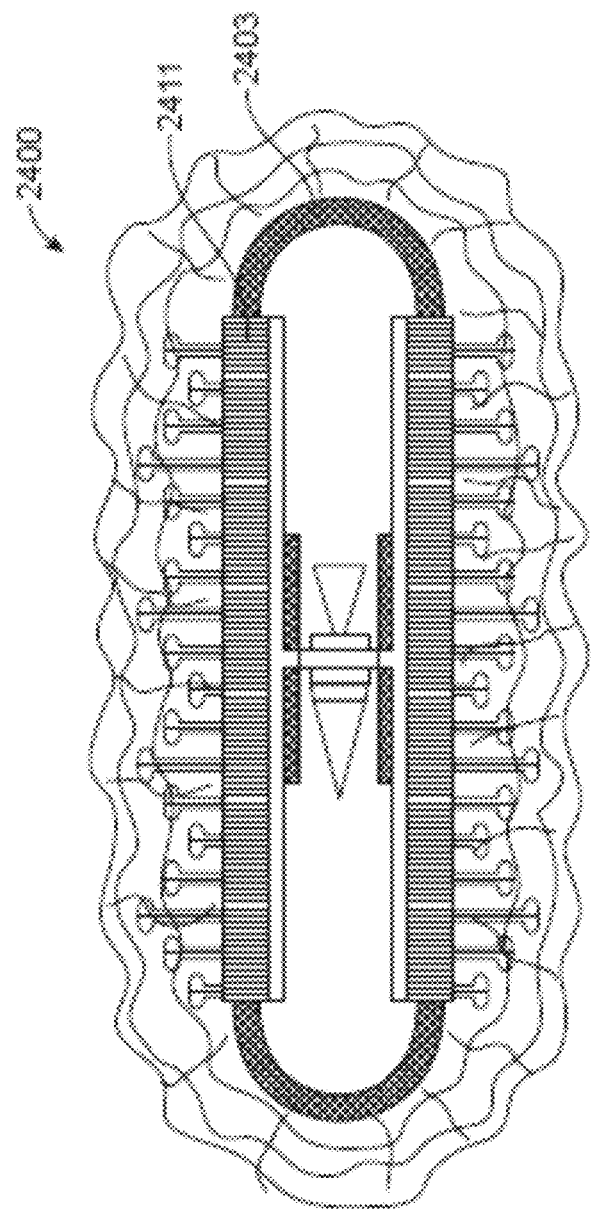

Referring to FIGS. 24A and 24B, in some embodiments, the implant 2400 can be configured without catheters and can instead include one or more membranes 2411 on the central module 2403 to move fluid in and out. The membrane 2411 can include similar layers to those described above with respect to the porous catheters.

In some embodiments, referring to FIGS. 25 and 26A-B, in some embodiments, the implant 2500, 2600 can include only a single catheter 2501, 2601 that is configured to take fluid in and out, either through reversing direction of the pumping, or, as shown in FIG. 25, by designing the catheter 2601 to have characteristics that allow some parts to bring fluid in and other parts to push fluid out.

Figure 27:
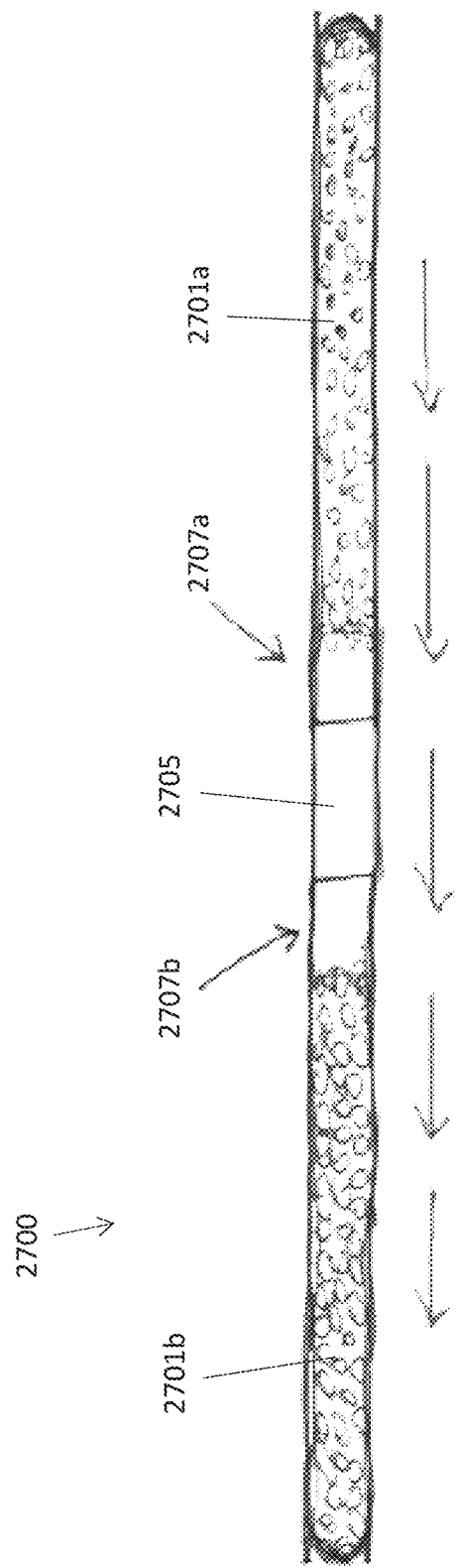
FIG. 27 shows the flow of body fluid through an exemplary glucose monitoring system.
Figure 28A:
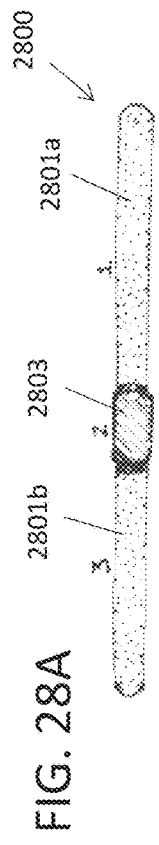
FIGS. 28A-E show an exemplary interstitial fluid glucose monitor.
Figure 28B:
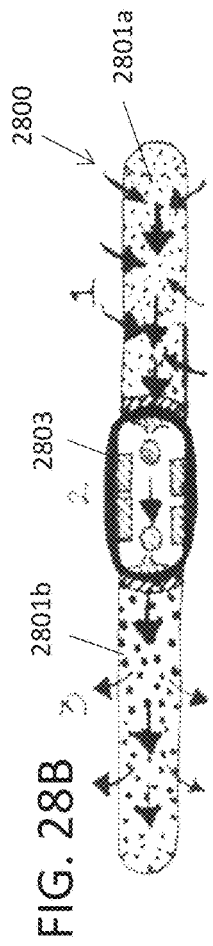
Figure 28C:
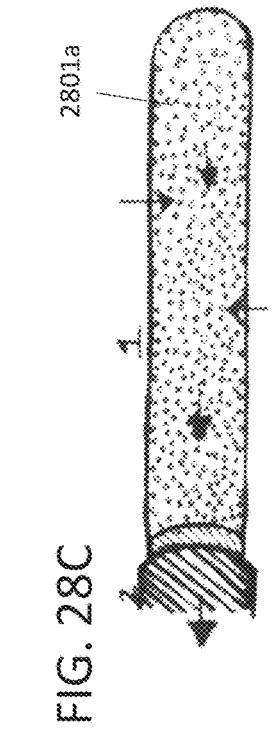
Figure 28D:
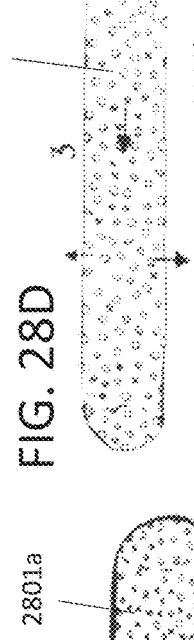
Figure 28E:
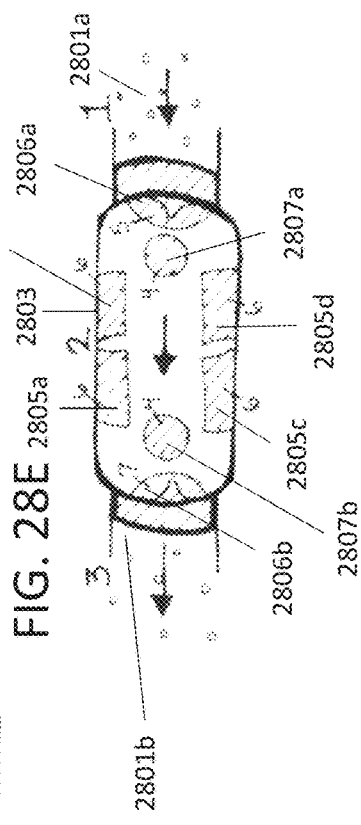

The implants described herein can be used as a long-term ultra-filtrate monitoring system, such as to monitor glucose. Referring to FIG. 27, the implant 2700 (which can have features similar to any of the implants described herein) can be placed in the blood stream or in the subcutaneous tissue. As shown by the arrows, solutes and water from the interstitial fluid or blood plasma move through the pores of a first porous catheter 2701a, into the lumen of the sensor 2705, and back out into the interstitial fluid through a second porous catheter 2701b by convective forces. Mechanical fluid pumps 2707a and 2707b can be used to produce a negative pressure on the inside of the micro-porous membrane relative to the hydrostatic and oncotic pressure external to the membrane. Long-term function of the implantable ultra-filtrate monitoring system requires the porous structure to remain patent (open) long-term, so that ultra-filtrate fluid can flow through the micro-fluidic system with low resistance, similar to the glomerulus of a kidney or a capillary blood vessel.

Using the glomerulus of the kidney as an example, the capillaries of the glomerulus are lined by endothelial cells that contain numerous pores called fenestrae that are 70-100 nm in diameter. These pores allow for the production of an ultra-filtrate of plasma by excluding all cells, platelets, and very large molecules. Similar to the glomerulus' endothelial cells, the outer layer of the implantable porous catheter may help to produce an ultra-filtrate of interstitial tissue fluid or plasma by excluding cells, platelets, and large molecules. The glomerulus has a basement membrane consisting of laminins, type IV collagen, agrin and nidogen, which are synthesized and secreted by endothelial cells and podocytes, and form a membrane 250-400 nm thick. This basement membrane excludes larger and charged molecules such as antibodies, coagulation proteins, and albumin—but has a low resistance to the passage of water, salt, glucose, and other small molecules. The concentration of glucose in the ultra-filtrate fluid traveling through the basement membrane into Bowman's Capsule is identical to the plasma glucose concentration. Podocyte cells that line the far side of the basement membrane facing Bowman's Capsule have numerous foot processes or pedicles that intermittently attach to the basement membrane. The space between adjacent foot processes is spanned by a slit diaphragm that contains a negatively charged surface coating (glycocalyx) and the proteins podocin and nephrin. The slit diaphragm pores exclude medium sized and negatively charged molecules such as albumin.

The Starling Forces dictate the continuous formation of ultra-filtrate from plasma for more than 75 years in most humans, without significant mechanical obstruction of the glomerulus' porous structure. Cells, platelets, and large molecules do not commonly obstruct the fenestrae of the endothelial cells, the basement membrane, or the slit diaphragms of the podocyte cells due to size and electric charge exclusion.

The mean arterial blood pressure (BP) within glomerulus capillary lumen has a hydrostatic pressure of approximately 90 mm Hg. A net hydrostatic pressure gradient (90 mm Hg minus 5 mm Hg) causes water, salt, and other molecules within the plasma to easily pass through the glomerulus membrane into the Bowman's Capsule. The glomerular filtration rate is the volume of ultra-filtrate that flows through the two kidneys each minute (more than 90 ml/min./1.73 $m^2$ in health). The oncotic pressure within the glomerulus capillaries is higher than the oncotic pressure within Bowman's Capsule, slightly decreasing the rate of ultra-filtrate formation. The large net positive outward force from the plasma into the Bowman's capsule leads to the rapid production of an ultra-filtrate that contains water, glucose and numerous small molecules, but not large proteins and cells from the blood. The two million glomeruli produce approximately 130 liters of ultra-filtrate every day, while the kidney's tubules re-absorb 129 liters of the processed ultra-filtrate back into the bloodstream, leaving 1 liter of ultra-filtrate to be excreted as urine.

The middle layer of the implantable porous catheter may be designed to use the Starling Forces and mimic the kidney structure, negative electrical charge, and filtration function of the glomerulus' three layer porous membrane (endothelial cells, basement membrane, and podocyte cells) to form an ultra-filtrate of tissue fluid or plasma for many years.

Using a continuous capillary blood vessel and basement membrane as an example, plasma can be transformed into an ultra-filtrate according the Starling Forces. The capillary pores and basement membrane produce several thousand liters of ultra-filtrate per day for more than 75 years without becoming obstructed by cells, platelets, or large molecules. Ultra-filtrate will rapidly leave the arteriolar side of the capillary due to the large hydrostatic pressure (+30 mm Hg) relative to the small tissue oncotic pressure (0 mm Hg), the small tissue hydrostatic pressure (−2 mm Hg) and small blood oncotic pressure (−10 mm Hg). Water, salt, glucose, and other small hydrophilic molecules ready and rapidly move through the capillary's endothelial cells and basement membrane with little resistance to flux. Interstitial fluid (ISF) around the venuole side of the capillary will rapidly re-enter the plasma due to a lower blood hydrostatic pressure (+10 mm Hg) and a higher plasma oncotic pressure (+30 mm Hg) relative to the tissue oncotic pressure (0 mm Hg) and tissue hydrostatic pressure (0 to +3 mm Hg). There is a net positive outward force from the plasma into the interstitial fluid. Approximately 1 liter of excess interstitial fluid is produced per day (42 ml/minute). This excess fluid is reabsorbed by the lymphatic system into the venous circulation, thus preventing the formation of tissue edema.

The middle layer of the implantable porous catheter may be designed to use the Starling Forces and mimic the structure, negative electric charge, and filtration function of the capillary's two layer porous membrane (endothelial cells and basement membrane).

In one embodiment of the long-term implantable ultra-filtrate monitoring system, the flow-through sensor can accurately and continuously monitor the concentration of glucose in an ultra-filtrate solution produced by the porous membranes of flexible catheter(s).

The long-term implantable glucose monitoring system can include three exemplary embodiments: (1) the interstitial fluid glucose monitoring system (ISF glucose sensor); (2) blood glucose monitoring system (blood glucose sensor); and (3) vascular shunt blood glucose monitoring system (vascular shunt blood glucose sensor), as described below.

Referring to FIGS. 28A-E, in one embodiment, an implant 2800 can be an ISF fluid glucose monitoring system. The implant 2800 can include two porous catheters 2801a and 2801b connected to a central module 2803. The central module can include fluid pumps 2807a and 2807b, glucose sensors 2805a, b, c, d, and one-way valves 2806a and 2806b.

As shown in FIG. 28, when the pumps 2807a and 2807b are activated, ISF fluid will move through the pores of the catheter 2801a into the catheter lumen, leading to a decreased hydrostatic pressure and slightly increased oncotic pressure within the adjacent subcutaneous tissue. The decreased hydrostatic pressure will cause water, salt, glucose, and other small molecules to rapidly move from the capillary's plasma into the interstitial space between the cells, leading to an increased ISF hydrostatic pressure. The negative hydrostatic and oncotic pressure within the porous catheter 2801a will cause water, salt, and glucose to constantly move from the plasma to the ISF (through the capillary membrane) and from the ISF into the central module 2703 (through the porous catheter 2801a) for measurement. The fluid can then be returned to the tissue through catheter 2101b. One-way valves 2806a and 2806b can ensure that fluid flows only in the desired direction.

The ISF glucose monitoring system 2800 can be implanted long-term in the subcutaneous tissue of ambulatory patients with type 1 diabetes and patients with type 2 diabetes that require insulin. The subcutaneous tissue of the abdomen, chest wall, and thigh are exemplary locations for implantation. Alternate locations for implantation include the mesentery of the bowel and between the visceral and parietal peritoneal membranes. The system can be implanted as an outpatient procedure in 20 to 30 minutes by a surgeon using local anesthesia.

The ISF glucose monitoring system can include the implant 2800 and an external electronics module. The implantable sensor 2800 can communicate with the external electronics module via telemetry. The external module can record and display the glucose measurement data, alerts and alarms for hyperglycemia and hypoglycemia, and can include a built-in blood glucose meter to facilitate sensor calibration.

The long-term implantable sensor 2800 may be implanted long term because of the multi-layered porous membrane catheters 2801a and 2801b that continuously and reliably produces an ultra-filtrate of interstitial fluid for many years following implantation in the tissue. The porous catheter composition, surface chemistry, thickness, surface area, electric charge, pore size, and pore density can be precisely controlled to produce about 1 to >10 microliters of ultra-filtrate per minute. The ultra-filtrate can flow through the porous membrane and glucose sensor continuously due to Starling forces and a pressure differential.

The concentration of glucose (and other analytes) with the sensor(s) 2805a-d with a high degree of accuracy, precision, sensitivity, specificity, reliability and stability. A variety of glucose sensing technologies can be used, including: (1) absorption spectroscopy (near-infrared-NIR), (2) absorption spectroscopy (mid-infrared-MIR), (3) Raman Spectroscopy, (4) enzyme-electrochemistry, (5) differential oxygen sensing, (6) fluorescence sensing, and (7) a sensor that changes physical form in response to a change in glucose.

The ISF sensor 2800 can include a MEMS/NEMS pump 2807a to produce a slight vacuum (negative pressure) that moves interstitial fluid through the catheter pores into the catheter lumen at about 1 to >10 microliters per minute. The ultra-filtrate can flow through the one-way valve 2806a and through the glucose sensor(s) 2805a-d. The concentration of glucose in the ultra-filtrate can be continuously measured using the flow-through sensor(s) 1805a-d once every 1 to 5 minutes. A second MEMS/NEMS pump 2807b and one-way valve 2806b can move the ultra-filtrate from the sensor(s) 2805a-d and into the lumen of the second porous catheter 2801b, out of the pores and into the subcutaneous tissue. The ultra-filtrate can be absorbed by the adjacent capillary and lymphatic vessels. The second MEMS/NEMS pump 2807b and valve 2806b may not be required for safe and effective performance, but redundancy may increase the reliability and longevity of the long-term implantable sensor system 2800.

The flow of ultra-filtrate can be monitored and controlled by one or two MEMS/NEMS pressure transducers and an algorithm that regulates the MEMS/NEMS pumps. The controlled pressure differential can maintain a continuous and steady flow of ultra-filtrate through the sensor despite dynamic changes in the hydrostatic pressure, oncotic pressure, and surface tissue pressure that surrounds the sensor's porous catheter(s) that can occur due to body position, level of hydration, muscle movement, and protein level within the plasma and subcutaneous tissue.

The ultra-filtrate leaving the second porous catheter 2801b can be rapidly absorbed into the adjacent capillary and lymphatic vessels (about 1 to >10 μl/min) of the subcutaneous tissue.

The ISF glucose sensor 2800 can be easily implanted within the subcutaneous adipose tissue by a physician using local anesthesia. Sensor insertion will damage epithelial cells, adipose cells, connective tissue fibers, nerves, capillaries and lymphatic vessels. The initial environment around the sensor will be a wound and will thus contain damaged cells, dead cells, activated platelets, coagulation factors, red blood cells, macrophages, neutrophils, lymphocytes, eosinophils, basophils, fibroblasts, and damaged fibers of hyaluronic acid, collagen, and elastin. Over time, thrombus will undergo fibrinolysis and the acute inflammatory process will transition into a granulation tissue with connective tissue, extracellular matrix (ECM), and new capillary-lymphatic vessels. The granulation tissue around the implanted sensor can transition into a stable vascular tissue with near-normal anatomy and physiology or transition into a more fibrous tissue with few blood vessels.

The long-term implantable ISF glucose sensor 2800 is designed with a size, shape, biomaterials, and anchoring methods that facilitate the transition of granulation tissue to near-normal loose connective tissue with numerous capillary and lymphatic vessels. The near-normal tissue will consist of adipose cells and macrophages surrounded by a thin layer of extracellular matrix containing hyaluronic acid, collagen, fibronectin, elastin fibers and interstitial fluid (1-2 micrometers of ECM between cells). Some of the ISF will be unbound within the ECM, while the majority of ISF will be bound to hyaluronic acid fibers to form a hydrated gel. An acute change in the concentration of blood glucose will result in a parallel change in the concentration of ISF glucose following a short time-lag.

The net ISF pressure within the loose connective tissue surrounding the porous catheters 1801*a* and 1801*b* (−1 to −2 mm Hg) will be produced by a hydrostatic pressure and an oncotic pressure. The loose connective tissue that grows within the interconnecting porous structure of the outer membrane of the catheters 2801*a* and 2801*b* will contain arterioles, capillaries, venuoles, lymphatics, and interstitial fluid.

The MEMS/NEMS pump 2807*a* and one-way valve 2806*a* will produce a negative pressure within the inside lumen of the glucose sensor's porous catheter 2801*a* (−4 to −6 mm Hg) relative to the surrounding tissue's ISF pressure. Interstitial fluid will thus move through the membrane pores into the lumen of the central module 2803 (1 to >10 microliters/minute) to form an ultra-filtrate that contains water, glucose, electrolytes, and other small molecules.

The second MEMS/NEMS pump 2805*b* and one-way valve 2806*b* will produce a pressure differential that moves the ultra-filtrate continuously through the micro-fluidics channel of the glucose sensor at 1 to >10 microliters/minute. The two MEMS/NEMS pumps 2807*a* and 2807*b* and one-way valves 2806*a* and 2806*b* will cause a pressure differential between the proximal and distal sides of the flow-through glucose sensor(s) 2805*a-d*.

An acute change in the blood and ISF glucose concentration surrounding the membrane will cause a rapid and parallel change in the ultra-filtrate glucose concentration traveling through the flow-through glucose sensor(s) 2805*a-d*. The glucose sensor(s) 2805*a-d* will measure the ultra-filtrate glucose concentration about every 1 to 5 minutes.

The distal MEMS/NEMS pump 2807*b* will increase the pressure within the lumen of the second flexible catheter (+1 to +2 mm Hg) relative to the surrounding tissue fluid pressure. The ultra-filtrate will move through the membrane pores into the surrounding loose connective tissue. The fluid will be rapidly absorbed into the capillary and lymphatic vessels that surround the porous membrane.

In an exemplary embodiment, the clinical performance of the long-term implantable ISF Glucose Monitoring System requires the porous membrane to remain stable and patent for years. The porous catheters 2801*a* and 2801*b* can thus be made up of a plurality of membrane layers, including an outer layer, a middle layer, and an inner layer. The outer portion of the membrane will interface with adjacent vascular connective tissue. The middle portion of the porous membrane will produce an ultra-filtrate of ISF. The inner portion of the porous membrane will provide structural support.

The outer most layer of the multi-layer membrane making up the porous catheters 2801*a* and 2801*b* will have a large inter-connecting pore structure (about 10 to 200 micrometer diameter), a thickness of about 20 to 200 micrometers, and a Bulk's modulus and Young's modulus similar to adjacent soft tissue. The outer membrane can be constructed of soft and hydrophilic biomaterials such as the hydrogels HEMA (hydroxyl-methyl-methacrylate), PMMA (poly-methyl-methacrylate), PHEMA (poly-hydroxy-methyl-methacrylate), and MM (methyl-methacrylate), polymers (ePTFE, Dacron, poly-glycolic acid) and the natural materials collagen (types I, III, IV, or V), elastin, fibronectin, laminin, hyuronic acid, fibrin, thrombin, and the synthetic basement membrane material Matrigel.

The outer membrane layer can also be constructed of nanometer sized carbon nanotubes and polymer fibers that are spun or weaved into an interconnecting mat-like structure. The nano-fibers can be spun into a structure with large open spaces that produce a large surface area for the ingrowth and adhesion of cells, connective tissue and ECM; leading to a vascular tissue with arterioles, capillaries, venuoles, and lymphatics.

The biomaterials can be functionalized with peptides (RGD, YISGR, PDSGR, REDV), receptors, growth factors, and immune modulators that enhance the adhesion and ingrowth of vascular tissue and extracellular matrix (arterioles, capillaries, venuoles, lymphatics, adipose cells, collagen, elastin, and hyuronic acid); and minimize the ingrowth of macrophages, fibroblasts, and dense fibrous tissue.

The middle layer of the multi-layer membrane can be manufactured with a MEMS/NEMS structure with precise pore size, shape, density (10,000 pores/mm$^2$), thickness, surface chemistry, texture, and electric charge. Photolithography (similar to computer chip manufacturing) can be used to produce a precise pore size (about 10 to >40 nanometers), shape (round, oval, square, rectangle, or slit) density (low, medium, and high) and thickness (about 5 to 100 micrometers). Water, glucose, and electrolytes will readily pass through a membrane with a pore size of 50 nanometers. Water, glucose, and electrolyte molecules easily and rapidly move in and out of capillary endothelial cells because a typical capillary has a pore size of 50,000 Daltons.

Water, glucose and other small molecules will easily pass through a porous membrane with an average pore size of 30,000 MW (Daltons).

Glucose will diffuse slowly through a small pore membrane (<13 nm) due to its molecular size (180 MW-Daltons; 0.37 Stokes radius). Glucose and water will move even slower through a very small diameter porous membrane (0.1 to 0.25 nanometer) due to molecular size and surface tension pf water (high resistance to flux). Insulin will pass through a membrane with a pore size of 3 to 6 nanometers (−30 to 60 Ångstroms), but at a much slower rate than water and glucose.

As described above, photolithography can also produce MEMS/NEMS posts that significantly increase the total surface area of the membrane in contact with surrounding vascular tissue. The biomaterial of the outer porous membrane will adhere to the post's large surface area to enhance mechanical attachment and prevent membrane delamination. In one embodiment, the posts can be constructed with numerous micro-pores that significantly increased the number of pores per area in direct contact with adjacent vascular tissue. The posts can be manufactures of a short, medium, and long length to localize the pores throughout the outer membrane's 3D porous structure; and throughout the surrounding vascular tissue to greatly increase the surface area for the formation of ultra-filtrate. A membrane with pores on the posts and between the posts will greatly increase the number of pores and the distribution of pores throughout the vascular tissue (similar to villi and microvilli on the intestines). The posts can be textured and shaped like a cylinder, mushroom, or ↑, ⊤, Ż, Γ, ‡, or other suitable shape and texture to enhance the surface area for the mechanical adhesion of the outer membrane to this membrane.

Photolithography can produce a pore structure with a wide open path, a taper, a reverse taper, an hourglass shape, a torturous path, a slit, a one-way valve and a bi-directional valve.

In one embodiment, the middle layer of the multi-layer membrane can be manufactured of nanometer sized carbon nanotubes, polymer fibers, or basement membrane connective tissue fibers from that are spun or weaved into an interconnecting mat-like structure. The nano-fibers can be spun into a very tight structure with very small space between the fibers. This tight mesh structure will prevent the ingrowth of cells and connective tissue while permitting the rapid movement of water, glucose, and electrolytes from once side to the other side, with minimal resistance to flow, similar to the basement membrane of the glomerulus or capillary endothelial cells.

The middle layer of the MEMS/NEMS membrane can be coated with BAM, diamond-like-carbon, or PTFE because they have the lowest coefficient of friction of any synthetic material, are self-lubricating, and are highly hydrophobic. BAM has a coefficient of friction of 0.02, diamond-like carbon 0.05, and PTFE 0.05 to 0.1 (compared with polished stainless steel of 1.0). A membrane coated with 2-3 micrometers of BAM, diamond-like carbon, or PTFE will significantly enhance the flow/flux of water, glucose, and electrolytes through the pores and prevent the adhesion of cells and protein within the porous structure.

The ceramic alloy of Aluminum, Magnesium, and Boride (BAM) is highly resistive to wear and has a lowest coefficient of sliding friction of any material (0.02 in AlMgB14-TiB2 composite). Diamond-like-carbon can be surface coated on a variety of materials and is strong, tough, inert, and self-lubricating. PTFE is an inert hydrophobic thermoplastic polymer that is strong, tough, flexible, and inert. PTFE has excellent dielectric properties making it suitable for use as an insulator in electronics.

The inner portion of the membrane can be designed for structural support. It can be manufactured like a stent, spring, catheter, disc or cylinder with multiple holes. The inner portion should be strong enough to support the middle and outer layer and avoid compression due to external forces or negative pressure (vacuum) caused by the MEMS/NEMS pumps.

The rate of ultra-filtrate formation can depend upon the overall characteristics of the interconnecting pore structure of the upper, middle, and inner layers prior to implantation in the body. Once implanted in the body, vascular tissue will grow into the porous structure of the outer layer toward the middle layer. The adhesion of protein and the ingrowth of cells and connective tissue may partially obstruct the interconnected pores of the outer, middle, and inner layers, leading to a change in the flow or flux of water, sodium, chloride, glucose, and other small molecules. The flow or flux of water through the porous catheter's three layer membrane at a specific hydrostatic pressure differential and oncotic pressure differential can be described as the sieve coefficient, Once implanted in the body, the rate of ultra-filtrate formation may depend upon the sieve coefficient of the three-layer porous membrane, the total area of the micro-porous membrane surrounded by vascular tissue, pore size, pore density, membrane thickness, pore connectivity, type of biomaterial, surface charge, local capillary blood flow, sieve coefficient of the local capillaries, local tissue hydrostatic pressure, and local tissue oncotic pressure.

The Starling Forces define the volume of fluid that leaves and enters the capillaries of the human body due to filtration. The entire five liters of blood in the circulation moves through the heart, lungs, and capillaries once per minute. Capillary filtration moves about 28.8 liters/day from the plasma into the interstitial tissue per day (total net transcapillary fluid movement). About 25.8 liters of this interstitial fluid are reabsorbed back into the capillaries per day. The three liters per day of interstitial fluid that are not reabsorbed are transported back into the venous circulation via the lymphatic system. Approximately 80,000 liters of water exit and enter the capillaries per day as the result of simple diffusion (total diffusional water flux of all of the capillary membranes).

Thus, the vascular tissue within the outer layer may have a large capacity for replacing the interstitial fluid removed from the vascular tissue during the formation of ultrafiltrate. The interstitial fluid removed from the vascular tissue by the process of ultra-filtration can be rapidly replaced by fluid entering the interstitial space from the adjacent capillary vessels.

The Starling equation defines the forces across the middle layer's semi-permeable membrane and allows calculation of the net fluid flux:

$$J_v = K_f([P_c - P_i] - \sigma[\pi_c - \pi_i])$$

$$([P_c - P_i] - \sigma[\pi_c - \pi_i])$$

is the net driving force where (Jv) is the solution to the equation known as the net filtration or net fluid movement across the porous membrane's middle layer;

Pc is the hydrostatic pressure within the lumen of the flexible catheter's micro-fluidic system produced and regulated by the MEMS/NEMS pumps, valves, pressure transducers, and software control algorithm;

Pi is the hydrostatic pressure within the vascular tissue located within the porous structure of the outer layer/membrane;

[Pc–Pi] is the hydrostatic pressure differential from the inside of the porous catheter's middle layer (Pc) relative to the outside of the porous catheter's middle layer (Pi);

πc is the oncotic pressure within the lumen of the flexible catheter's micro-fluidic system;

πi is the oncotic pressure within the vascular tissue located within the porous structure of the outer layer/membrane;

[πc–πi] is the oncotic pressure differential from the inside of the porous catheter's middle layer (πc) relative to the outside of the porous catheter's middle layer (πi);

Kf is the constant of proportionality called the filtration coefficient of the porous membrane. A high filtration coefficient value indicates the outer, middle, and inner layers of the porous membrane are highly permeable to the flow or flux of water, salt, glucose, and other small molecules. The filtration coefficient is the product of porous membrane surface area x porous membrane hydraulic conductance; and σ is called the reflection coefficient, a factor that corrects the oncotic pressure differential if any large molecules are able to pass through the outer, middle, and inner layers to reach the lumen of the porous catheter's micro-fluidic system.

A MEMS/NEMS pump can produce a negative hydrostatic pressure within the lumen of the micro-fluidic system relative to the outside of the porous membrane. A hydrostatic pressure differential will cause water, salt, glucose, and other small molecules to move from the vascular tissue's interstitial fluid through the membrane layers, to enter the lumen of the micro-fluidics system (for example: Pi−Pc=−2 mm Hg minus −35 mm Hg=−37 mm Hg hydrostatic pressure causing water, salt, glucose, and other small molecules to move through the porous membrane layers into the lumen of the micro-fluidics system. The oncotic pressure differential may not influence the flow/flux of ultra-filtrate.

In summary, the long-term implantable ISF glucose sensor 2800 will move tissue fluid through a porous membrane into a micro-fluidic system that contains a glucose sensor and a second porous membrane that causes the fluid to be absorbed by adjacent vascular tissue. The MEMS/NEMS pressure sensors, MEMS/NEMS pumps and a control algorithm will regulate the continuous formation and flow of ultra-filtrate through the glucose sensor's micro-fluidics channel.

Referring to FIGS. 29A-D, in one embodiment, an implant 2900 can be a blood glucose monitoring system. The implant 2900 can include two porous catheters 2901*a* and 2901*b* connected to a central module 2903. The central module can include fluid pumps 2907*a* and 2907*b*, glucose sensors 2905*a, b, c,* and *d,* and one-way valves 2906*a* and 2906*b*. Further, the implant 2900 can be configured to communicate with an external electronics module via telemetry. The external module records and displays the glucose measurement data, alerts and alarms for hyperglycemia and hypoglycemia, and has a built-in blood glucose meter to facilitate sensor calibration.

Referring to FIGS. 30A-B, the porous catheter 2901*a* can be is implanted within the venous bloodstream of ambulatory patients with type 1 diabetes and patients with type 2 diabetes that require insulin. In one embodiment, the implant 2900 can be inserted into the subclavian vein and advanced into the superior vena cava (SVC). The rest of the implant 2900 (i.e., the second porous catheter 2901*b* and the central module 2903 including the MEMS/NEMS pump 2907*a*, the one-way valve 2906*a*, the flow-through glucose sensor 2905*a-d*, the second one-way valve 2906*b*, the second MEMS/NEMS pump 2907*b*, as shown in FIGS. 29A-D) can be implanted within the subcutaneous tissue adjacent to the heart).

Referring back to FIGS. 29A-D, the ultra-filtrate will move through the lumen of the catheter 2901*a*, the valve 2906*a*, the pump 2907*a*, the glucose sensor 2905*a-d*, the second pump 2907*b*, the second valve 2906*b*, and the second flexible porous catheter 2901*b*. The pump 2901*a* can produce negative pressure within the SVC porous catheter 2901*a* relative to the hydrostatic and oncotic pressure of the vena cava plasma to produce an ultra-filtrate that contains water, glucose, electrolytes, and other small molecules at 1 to >10 microliters per minute. The second pump 2907*b* and valve 2906*b* will move the ultra-filtrate from the glucose sensor 2905*a-d* into the lumen of the second catheter 2901*b*, out of the pores and into the subcutaneous tissue. The ultra-filtrate will be rapidly absorbed into the capillary and lymphatic vessels surrounding the porous catheter 2901*b*.

The multi-layered SVC porous catheter 2901*a* will produces an ultra-filtrate from the whole blood plasma. The SVC catheter membrane composition, thickness, area, electric charge, pore size, and pore density can be precisely controlled to produce 1 to >10 microliters of ultra-filtrate per minute. The outer porous membrane layer will inhibit the adhesion of plasma proteins, platelets, coagulation factors, fibrin, and thrombus. The ultra-filtrate will continuously flow through the SVC micro-porous membrane of the catheter 2901*a* due to a pressure differential (P1−P2); through the glucose sensor due to a pressure differential (P2−P3); and through the subcutaneous tissue micro-porous membrane due to a pressure differential (P3−P4).

The concentration of glucose in the ultra-filtrate can be continuously measured once every 1 to 5 minutes. The concentration of glucose (and other analytes) will be measured with a high degree of accuracy, precision, sensitivity, specificity, reliability and long-term stability using near-infrared absorption spectroscopy (NIR), mid-infrared absorption spectroscopy (MIR), an enzyme-based electrochemical sensor, a differential oxygen sensor, a fluorescence sensor, and/or a sensor that changes physical shape in response to a change in glucose.

The flow of ultra-filtrate can be monitored and controlled by MEMS/NEMS pressure transducers (sensors), an algorithm, and the MEMS/NEMS pumps 2907*a* and 2907*b*. The controlled pressure differential will maintain a steady flow of ultra-filtrate through the sensor despite dynamic changes in the hydrostatic and osmotic pressures of the blood surrounding the intravascular porous catheter and the hydrostatic and osmotic pressures of the interstitial tissue fluid surrounding the subcutaneous tissue porous catheter.

In an exemplary embodiment, the clinical performance of the long-term implantable blood glucose monitoring system 2900 improves when the multi-layered porous membrane of the catheter 2901*a* remains stable and patent for years. The outer portion of the intra-vascular catheter will interface with the flowing blood in a large central vein. The middle portion of the porous membrane will produce an ultra-filtrate of whole blood plasma. The inner portion of the porous membrane will provide structural support.

The outer most layer of the membrane of the venous catheter 2901*a* can have a highly flexible surface that minimizes the adhesion of platelets, clotting factors, plasma proteins, fibrin, and thrombus. The outer membrane will have an inter-connecting pore structure (50 nanometers to 6 micrometers diameter), a thickness of 20 to 100 micrometers and a Bulk's modulus and Young's modulus similar to soft tissue.

The outer layer of the catheter can be coated with BAM, diamond-like-carbon, or PTFE because they have the lowest coefficient of friction of any synthetic material, are self-lubricating, and are highly hydrophobic. BAM has a coefficient of friction of 0.02, diamond-like carbon 0.05, and PTFE 0.05 to 0.1. The high degree of blood flow and shear forces within the vena cava lumen will dislodge adhered proteins, platelets, and thrombus to maintain an open pore structure. The outer layer can be made of hemo-compatible biomaterials such as the hydrogels HEMA (hydroxyl-methyl-methacrylate), PHEMA (poly-hydroxy-methyl-methacrylate), MM (methyl-methacrylate); polymers (Dacron, PE-polyethylene, HDPE-high density polyethylene, PEG-polyethylene glycol, Sulfobetaine-polySB, polycarbonate, silicone, polyvinyl alcohol, polypropylene, cellulose acetate, mixed-ester cellulose, polytetrafluoroethylene (PTFE-Teflon), and acrylic copolymer); and nanometer sized carbon nanotubes and polymer fibers that are spun or weaved into an interconnecting mat-like structure. The biomaterials can be functionalized with peptides, lipids, glycolipids, glycoproteins, synthetic polymers (PEG-polyethylene glycol, Sulfobetaine-polySB), immune modulators, and anticoagulants that minimize the adhesion of platelets, plasma proteins, coagulation factors, white blood cells, red blood cells, fibrin, thrombus, fibroblasts, macrophages, and bacteria.

The middle layer of the multi-layer membrane can be manufactured with a MEMS/NEMS membrane with a precise pore size, shape, density, thickness, surface chemistry, texture, and electric charge. Photolithography (similar to computer chip manufacturing) can be used to produce a precise pore size (5 nanometers to 5 micrometers) shape (round, oval, square, rectangle, or slit) density (1,000 to 10,000 pores/mm$^2$) and thickness (10 to 100 micrometers). The middle layer of the MEMS/NEMS membrane can be coated with BAM, diamond-like-carbon, or PTFE because they have the lowest coefficient of friction of any synthetic material, are self-lubricating, and are highly hydrophobic. A membrane coated with 2-3 micrometers of BAM, diamond-like carbon, or PTFE will significantly enhance the flow/flux of water, glucose, and electrolytes through the pores and prevent the adhesion of cells and protein within the porous structure.

Photolithography can produce a pore structure with a wide open path, a one-way valve, a bi-directional valve, a taper, a reverse taper, an hourglass shape, or a torturous path. Water, glucose and other small molecules will easily pass through a membrane with a 30,000 Dalton pore size because water, glucose, and electrolyte molecules easily and rapidly move in and out of capillary endothelial cells with a pore size of 50,000 Daltons.

Photolithography can be used to produce a MEMS/NEMS membrane with posts that significantly increase the total surface area of the membrane in direct contact with the outer membrane and flowing blood. The posts can be manufactured of a short, medium, and long length to localize the pores throughout the outer membrane's 3D structure. The posts can have pores or micro-pores that significantly increase the area of membrane available for the flux of water, glucose, and other small analytes.

The sensor's power source (battery) and electronics can be used to produce an electrical charge on the surface of the MEMS/NEMS membrane and within the pore structure (negative, positive, or alternating charge). The electric charge can be used to enhance or inhibit the flow of water, glucose, and electrolytes through the membrane pores. The electric charge can also be used to inhibit the adhesion of plasma proteins, platelets, WBC, RBC, fibrin and thrombus on the biomaterial surface and keep the pores patent for years.

In one embodiment, the middle layer can be manufactured of nanometer sized carbon nanotubes, polymer fibers, or basement membrane fibers (Matrigel) that can be spun or weaved into an interconnecting mat-like structure. The nano-fibers can be spun into a very tight structure with small spaces between the fibers. This tight mesh structure will permit the rapid movement of water, glucose, and electrolytes from one side or the membrane to the other side, with minimal resistance to flow, similar to the basement membrane of the glomerulus or capillary endothelial cells. Cells, platelets, and fibrous proteins will be excluded from the pores and space between the fibers.

The inner portion of the membrane of the catheter 2901a can be designed for structural support. It can be manufactured like a stent, spring, catheter, disc or cylinder with multiple holes. The inner portion should be strong enough to support the middle and outer layer and avoid compression due to external forces or negative pressure caused by the MEMS/NEMS pumps.

The flow-through glucose sensor 2903 and the flexible porous catheter 2901b can be implanted long-term within the subcutaneous tissue. This catheter 2901b can have the same structure and function as the porous catheter described above for the ISF Glucose Monitoring System. Ultra-filtrate will flow out of the flexible porous catheter into the subcutaneous tissue to be absorbed by adjacent capillary and lymphatic vessels. Thus, ultra-filtrate will continuously flow from the vena cava plasma to the subcutaneous adipose tissue of the chest wall at 1 to >10 ul/minute.

Referring to FIGS. 31A-E, in one embodiment, an implant 3100 can be a vascular shunt blood glucose monitoring system. The implant 3000 can include two vascular graft portions 3131a and 3131b connected to a central module 3003. The central module 3003 can include one or more porous membrane windows 3110a and 3110b fluid pumps 3007a and 3007b, glucose sensors 3005a, b, c, and d, and one-way valves 3006a and 3006b. Further, the implant 3100 can be configured to communicate with an external electronics module via telemetry. The external module records and displays the glucose measurement data, alerts and alarms for hyperglycemia and hypoglycemia, and has a built-in blood glucose meter to facilitate sensor calibration.

The vascular shunt blood glucose monitoring system may consist of a synthetic vascular graft connected to an artery and a vein, or an artery to an artery, as shown in FIGS. 31A and 32A-B. A surgeon can attach one end of the shunt to a peripheral artery and the other end to a peripheral vein with suture, vascular staples or tissue glue. The shunt 3100 can be constructed of commercial vascular graft material (ePTFE, polyurethane, or Dacron) (for the graft portions 3131a and 3131b) and one or more embedded micro-porous membrane "windows" in the central portion 3101. Ultra-filtrate will be formed as blood flows through the vascular graft portions 3131a and 3131b and past the porous windows 3110a and 3110b with a hydrostatic pressure of +60 to +80 mm Hg and a plasma oncotic pressure of −30 mm Hg. The net positive pressure of +30 to +60 mm Hg will cause ultra-filtrate to flow through the micro-porous membrane "window" into the attached flow-through glucose sensor.

Referring to FIGS. 32A-B, in some embodiments, ultra-filtrate will be formed as blood flows through the vascular graft and past a porous window(s) 3010a and 3010b. In one embodiment, the hydrostatic pressure can be +60 to +90 mm Hg and a plasma oncotic pressure can be −30 mm Hg. The net positive pressure of +30 to +60 mm Hg will cause ultra-filtrate to flow through the micro-porous membrane "window" into the attached flow-through glucose sensor. The large hydrostatic pressure within the lumen of the vascular graft relative to the small hydrostatic pressure within the adjacent subcutaneous vascular tissue causes water, salt, glucose, and other small analytes to move from the plasma into the adjacent vascular tissue and ISF. The long-term implantable blood analyte monitoring system may not require a fluid pump because the large hydrostatic pressure differential is produced by the patient's systemic blood pressure (MAP=90 mm Hg). The vascular graft implant therefore may not need an active pumping mechanism.

The concentration of ultra-filtrate glucose can be measured every 1 to 5 minutes using the same analytical methods as above. Ultra-filtrate will travel through the sensor and through a second porous membrane into the vein.

Ultra-filtrate will form and move through the porous membrane window and glucose sensor due to the positive net pressure. The concentration of ultra-filtrate glucose will be measured using a NIR/MIR optical, differential oxygen, enzyme-electrochemical, fluorescence or mechanical sensor every 1 to 5 minutes. The controlled pressure differential will maintain a steady flow of ultra-filtrate through the flow-through sensor despite dynamic changes in the hydrostatic and osmotic pressures on both sides of the microporous membrane "window".

The A-V shunt's porous membrane window(s) 3110a and 3110b can be manufactured using microchip photolithography methods, nano-3D printer methods, laser degradation, or traditional synthetic polymerization methods. The pore size, depth, density, chemistry, and electric charge can be dynamically adjusted to control the flow or flux of ultra-filtrate.

Figure 33:
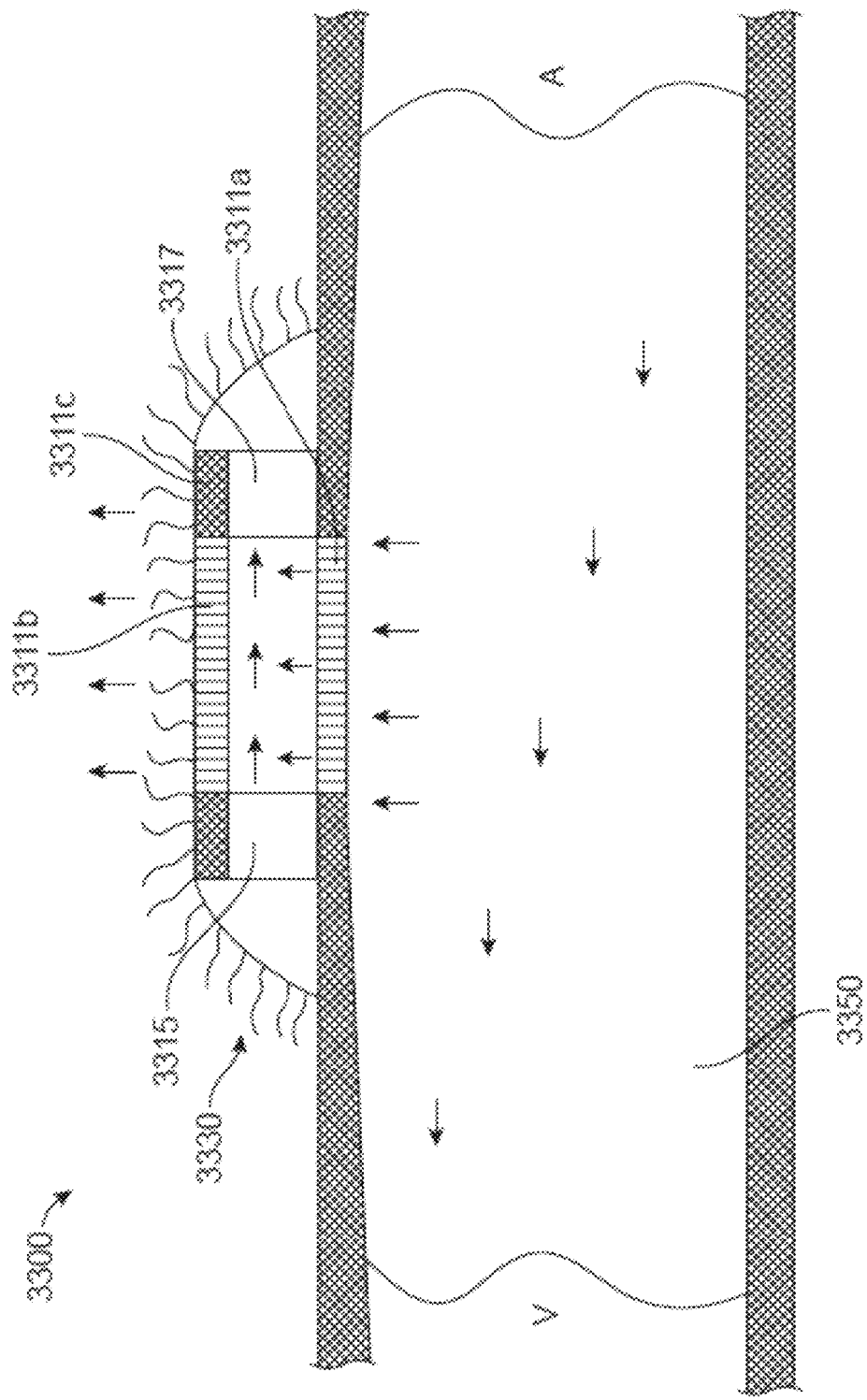
FIG. 33 shows another embodiment of a vascular shunt glucose monitor.

In some embodiments, referring to FIG. 33, the vascular shunt 3300 can include a main body 3350 connecting between an artery (A) and vein (V) and a surface sensor 3330. The surface sensor 330 can include a plurality of different membranes 3311a, b, and c configured similar to the layers of the porous catheter described above. Further, fluid can flow through the sensor from the light source 3315 to the detector 3317 to measure the amount of analyte therein.

One embodiment of the invention combines the long-term implantable glucose monitoring system with a computer controller and an insulin delivery system to produce an Artificial Pancreas System. The invention can be separated into three components: 1) a stand-alone implantable glucose monitoring system (glucose sensor), 2) a stand-alone insulin delivery system, and 3) a computer software program that controls the Artificial Pancreas System (AP System).

The insulin delivery system (insulin pump and catheter) and AP System controller can be implantable or external to the body (non-invasive) while the glucose monitoring system is implanted long-term in the body (invasive). A closed-loop AP System will maintain the blood glucose concentration in the target range (fasting 80 to 120 mg/dl and post-prandial 130 to 160 mg/dl) by adjusting the infusion dose of insulin every 1 to 5 minutes. The insulin pump can deliver insulin into a subcutaneous tissue catheter (CSII—continuous subcutaneous insulin infusion catheter), a central vein catheter (CIVII—continuous intravenous insulin infusion catheter), or a portal vein catheter (CPVII—continuous portal vein insulin infusion catheter).

The insulin pump can be combined with a long-term implantable insulin delivery catheter modified to enhance the PK/PD of insulin absorption into the circulation. For example, the insulin delivery catheter described in U.S. Pat. No. 9,639,612, the entirety of which is incorporated by reference herein, can be attached to an external insulin pump or a long-term implantable insulin pump.

The glucose monitoring system can be combined with an insulin/glucagon pump and a closed-loop control algorithm to produce an Artificial Pancreas System.

Figure 34:
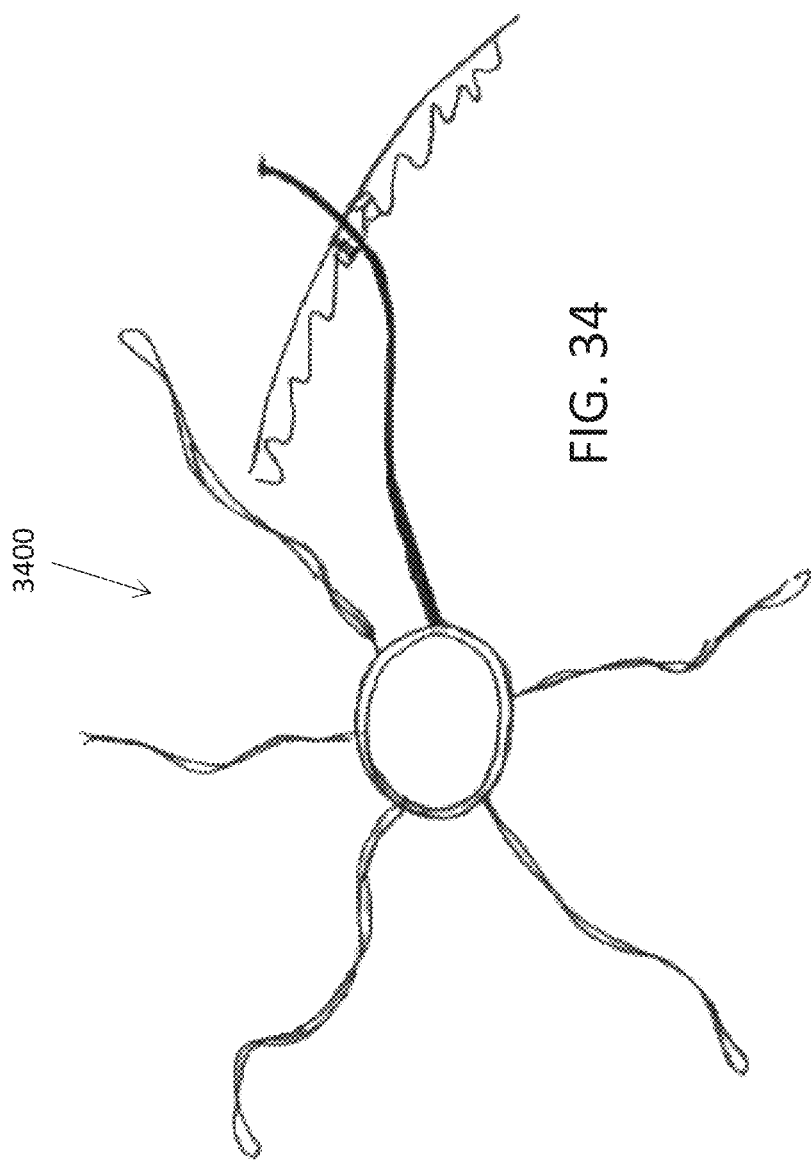
FIG. 34 shows an exemplary implantation method for a glucose monitor.

Referring to FIG. 34, in an alternative embodiment, the implant 3400 is implanted primarily under the skin, but an external module 3233 (including a batter, sensor, pumps, etc.) sits outside of the skin. In this embodiment, the ultra-filtrate is moved outside of the body.

Referring to FIG. 34, the implant can be implanted into the skin by making a small incision in the skin. The central module of the implant can then be placed under the skin. Each flexible porous catheter can include a needle and suture attached thereto. The needle can then be pushed from the pocket, through the tissue, and out to the outside of the skin, and the needle can be removed, leaving the catheter spread out from the rest of the body. This method can advantageously minimize tissue trauma.

Figure 35:
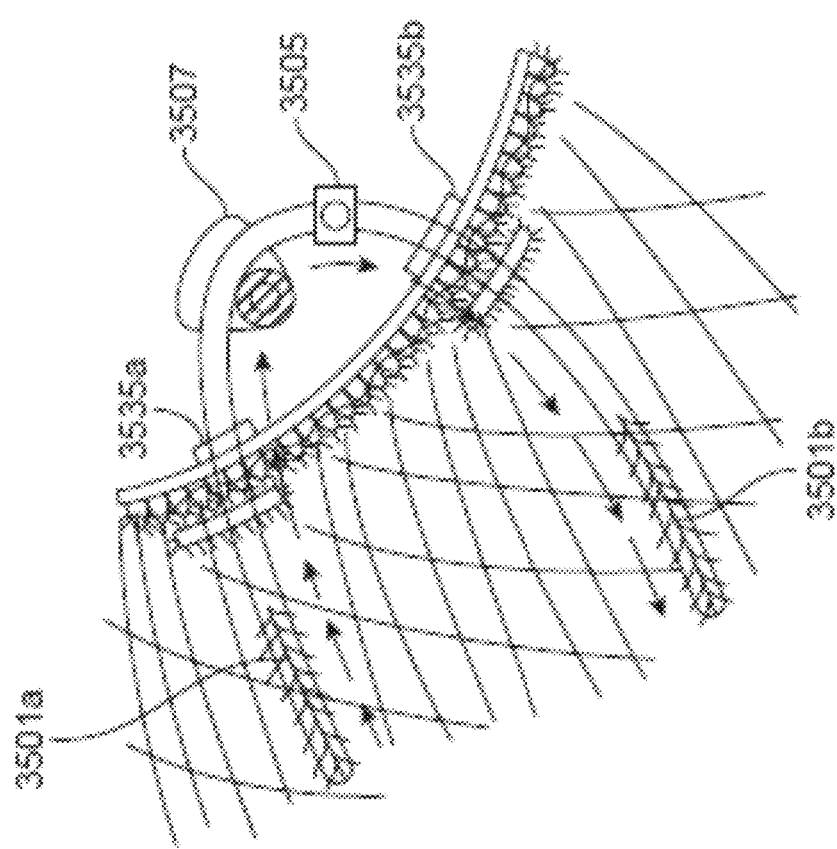
FIG. 35 shows another embodiment of an implanted glucose monitor.

In some embodiments, referring to FIG. 35, only the porous catheters 3501a and 3501b are implanted under the skin while the pump 3507 and sensor 3505 are external to the skin. Collars 3535a and 3535b can be act as barriers to prevent bacteria from entering the body at the catheter site.

Further, in some embodiments, the central module can be sutured to the fascia while the flexible catheters can move freely within the system.

Figure 36:
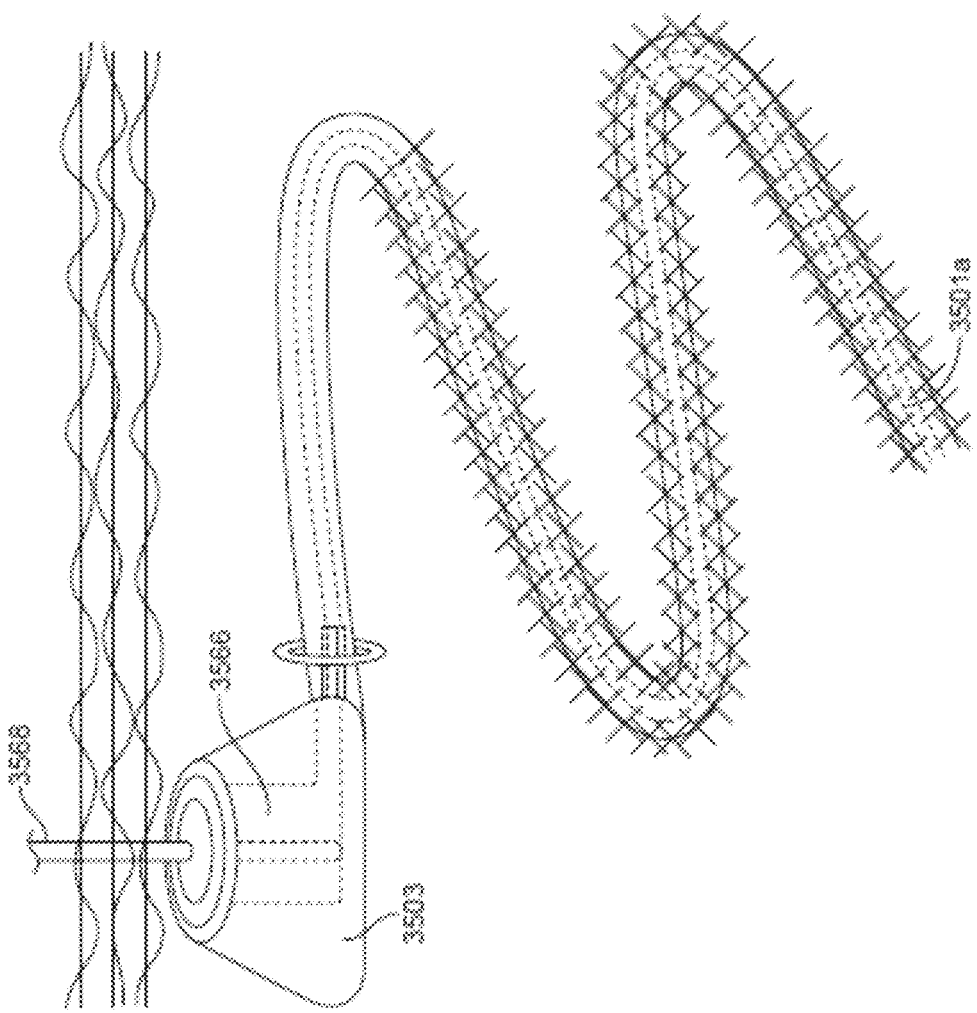
FIG. 36 shows another embodiment of a glucose monitor.

Further, referring to FIG. 36, in some embodiments, a device 3500 can include a porous catheter 3501a to produce an ultra-filtrate, as described above, and a central module 3503 directly under the skin. The central module 3503 can be designed to collect ultra-filtrate and can have an access point 3566 for a needle or syringe. To obtain a sample, a needle 3568 can be pushed through the skin into the central module 3503 to collect the ultra-filtrate, and a measurement of the analyte (e.g., glucose) levels can be taken.

Although embodiments of this invention have been described with reference to the accompanying drawings, it is to be noted that various changes and modifications will become apparent to those skilled in the art. Such changes and modifications are to be understood as being included within the scope of embodiments of this invention as defined by the appended claims. For example, exemplary embodiments are provided in the appendix, attached hereto. Moreover, any exemplary embodiment, system, and/or method may be used in any combination, sub-combination, or recombination, such that any feature or step may be duplicated, added, removed, or otherwise included in any described system, method, or embodiment.

What is claimed is:

1. A method of measuring a level of analyte in body fluid, comprising:
    implanting a monitoring system into a body of a patient, the implanted monitoring system having a first multi-layer porous membrane, a second multi-layer porous membrane, and a sensor, the monitoring system further comprising a catheter, the first multi-layer porous membrane forming a wall of the catheter;
    creating an ultra-filtrate from a body fluid by imparting a pressure differential to filter a portion of the body fluid through the first multi-layer porous membrane of the implanted monitoring system, the first multi-layer porous membrane having an outer layer and an inner layer, the outer layer having larger pores than the inner layer;
    measuring an amount of analyte in the ultra-filtrate with the sensor of the implanted monitoring system; and
    returning the ultra-filtrate to the body fluid through the second multi-layer porous membrane.

2. The method of claim 1, further comprising calibrating the monitoring system based upon an external measurement of the analyte.

3. The method of claim 1, wherein the implanting step comprises implanting the catheter into subcutaneous vascular tissue, the method further comprising promoting ingrowth of the subcutaneous vascular tissue into the pores of the outer layer.

4. The method of claim 1, wherein the implanting step comprises implanting at least a portion of the catheter into a blood vessel.

5. The method of claim 1, wherein the implanting step comprises implanting the catheter into a blood vessel and implanting a central module connected to the porous catheter into subcutaneous tissue.

6. The method of claim 1, wherein the implanting step comprises implanting the monitoring system between a vein and an artery as a vascular shunt.

7. The method of claim 1, wherein the sensor is an optical sensor.

8. The method of claim 1, wherein the pressure differential pulls the ultra-filtrate into the sensor and returns the ultra-filtrate to the body.

9. The method of claim 8, further comprising maintaining a constant pressure differential despite dynamic changes in hydrostatic pressure or oncotic pressure.

10. The method of claim 1, wherein a rate of creating the ultra-filtrate is between 0.5 µL/min and 20 µL/min.

11. The method of claim 1, further comprising displaying the measured amount of analyte.

12. The method of claim 1, wherein the analyte is glucose and wherein the body fluid is interstitial fluid or blood.

13. The method of claim 12, further comprising activating an alarm for hyperglycemia based upon the amount of analyte, hypoglycemia based upon the amount of analyte, or a rapid rate of change in the amount of analyte.

14. The method of claim 5, wherein the first multi-layer porous membrane includes a third layer configured to provide structural support to the membrane.

15. The method of claim 1, wherein the inner layer of the first multi-layer porous membrane comprises a plurality of extensions configured to extend into the outer layer of the first multi-layer porous membrane.

16. The method of claim 3, wherein creating the ultra-filtrate from a body fluid using a first multi-porous membrane comprises creating the ultra-filtrate using the inner layer of the first multi-porous membrane.

17. The method of claim 1, further comprising reversing a direction of flow through the first and second multi-layer porous membranes such that the body fluid flows through the second multi-layer porous membrane and the ultra-filtrate returns to the body through the first multi-layer porous membrane.

18. The method of claim 1, wherein the second multi-layer porous membrane includes an outer layer and an inner layer, the outer layer having larger pores than pores of the inner layer.

* * * * *